US012257236B2

(12) United States Patent
Guarino, Jr. et al.

(10) Patent No.: US 12,257,236 B2
(45) Date of Patent: *Mar. 25, 2025

(54) ORAL FORMULATIONS OF METRONIDAZOLE AND METHODS OF TREATING AN INFECTION USING SAME

(71) Applicant: Appili Therapeutics Inc., Halifax (CA)

(72) Inventors: Bernard J. Guarino, Jr., Lodi, NJ (US); Jamie L. Doran, Guelph (CA); Zorana Radovic, Laval (CA); Kevin Sullivan, Halifax (CA); Armand Louis Balboni, Waterford, VA (US)

(73) Assignee: Appili Therapeutics Inc., Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/072,154

(22) Filed: Nov. 30, 2022

(65) Prior Publication Data

US 2023/0086660 A1 Mar. 23, 2023

Related U.S. Application Data

(63) Continuation of application No. 16/959,536, filed as application No. PCT/CA2019/050053 on Jan. 16, 2019, now Pat. No. 11,541,035.

(60) Provisional application No. 62/617,703, filed on Jan. 16, 2018.

(51) Int. Cl.
| | |
|---|---|
| *A61K 31/4164* | (2006.01) |
| *A61K 9/00* | (2006.01) |
| *A61K 47/02* | (2006.01) |
| *A61K 47/14* | (2017.01) |
| *A61K 47/26* | (2006.01) |
| *A61K 47/38* | (2006.01) |
| *A61K 47/46* | (2006.01) |
| *A61P 31/04* | (2006.01) |

(52) U.S. Cl.
CPC ........ *A61K 31/4164* (2013.01); *A61K 9/0053* (2013.01); *A61K 47/02* (2013.01); *A61K 47/14* (2013.01); *A61K 47/26* (2013.01); *A61K 47/38* (2013.01); *A61K 47/46* (2013.01); *A61P 31/04* (2018.01)

(58) Field of Classification Search
CPC .. A61K 31/4164; A61K 9/0053; A61K 47/02; A61K 47/14; A61K 47/26; A61K 47/38; A61K 47/46; A61P 31/04
USPC ........................................................ 514/398
See application file for complete search history.

(56) References Cited

U.S. PATENT DOCUMENTS 11,541,035 B2 * 1/2023 Guarino, Jr. ....... A61K 31/4164

FOREIGN PATENT DOCUMENTS

| CN | 103393596 A | 11/2013 |
|---|---|---|
| WO | 2013058496 A1 | 4/2013 |

OTHER PUBLICATIONS

International Search Report and Written Opinion of the International Searching Authority for International Application No. PCT/CA2019/050053, dated Apr. 3, 2019.
Aguzzi et al., 2007, "Use of clays as drug delivery systems: possibilities and limitations" Appl Clay Sci. 36:22-36.
Bai et al., 2017, "Palatability of a novel oral formulation of prednisone in healthy young adults" J Pharm Pharmacol. 69(4): 489-496.
Bastiaans et al., 2005, "In vivo and in vitro palatability testing of a new paediatric formulation of valaciclovir" Br J Clin Pharmacol. 83 (12): 2789-2797.
Bempong et al., 2005 "A stability-indicating HPLC assay for metronidazole benzoate." Journal of Pharmaceutical and Biomedical Analysis 38, 776-780.
Bhattacharjee et al., 2016 "Approaches taken for masking of bitter taste in pharmaceutical products" World Journal of Pharmacy and Pharmaceutical Sciences. 5(8): 1752-64.
Ciullo Pa. 1981 "Rheological properties of magnesium aluminum silicate/xantham gum dispersions." J Soc Cosmet Chem. 32:275-278.
Metronidazole (metronidazole) tablet. US National Library of Medicine. https://dailymed.nlm.nih.gov/dailymed/drugInfo.cfm?setid=a66abf44-9ae9-4342-b69a-ebaa1f9b7d78. Accessed Jul. 25, 2017.
D'Hondt et al., 2014 "Investigation of active pharmaceutical ingredient loss in pharmaceutical compounding of capsules" J Pharm Biomed Anal. 96:68-76.
Da Silva et al., 2016 "Discriminative Dissolution Method for Benzoyl Metronidazole Oral Suspension" AAPS PharmSciTech, vol. 17, No. 3.
Duro et al., 1999 "Interfacial adsorption of polymers and surfactants: implications for the properties of disperse systems of pharmaceutical interest" Drug Dev Ind Pharm, 25(7): 817-829.
Elder and Crowley. Antimicrobial preservatives part two: choosing a preservative. American Pharmaceutical Review [Internet]. Jan. 2012 [cited Jan. 12, 2017]. CompareNetworks Inc. Available from: http://www.americanpharmaceuticalreview.com/Featured-Articles/38885-Antimicrobial-Preservatives-Part-Two-Choosing-a-Preservative/.
Flagyl Metronidazole tablet label 2015.
Gee et al., 2007 "Palatability of liquid anti-infectives: clinician and student perceptions and practice outcomes" J Pediatr Pharmacol Ther. 12:216-223.
Healy et al., 1997 "Reduced tetracycline bioavailability caused by magnesium aluminum silicate in liquid formulations of bismuth subsalicyclate" Ann Pharmacother, 31:1460-1464.

(Continued)

*Primary Examiner* — Kristin A Vajda
(74) *Attorney, Agent, or Firm* — Woodard, Emhardt, Henry, Reeves & Wagner, LLP

(57) ABSTRACT

The present disclosure provides oral pharmaceutical compositions comprising: 1) metronidazole or a pharmaceutically acceptable salt thereof; and magnesium aluminum silicate; or 2) metronidazole or a pharmaceutically acceptable salt thereof; magnesium aluminum silicate; and a flavoring agent. Methods of treating infection utilizing the oral pharmaceutical compositions are also provided.

21 Claims, 10 Drawing Sheets

(56) References Cited

OTHER PUBLICATIONS

Houghton et al., 1982 "A comparison of the pharmacokinetics of metronidazole in man after oral administration of single doses of benzoylmetronidazole and metronidazole" Br J Clin Pharmacol, 14:201-206.
Ishizaka et al., 2007 "The suppression of enhanced bitterness intensity of macrolide dry syrup mixed with an acidic powder" Chem Pharm Bull, 55:1452-1457.
Kalaskar et al., 2014 "Taste masking: a novel technique for oral drug delivery system" Asian Journal of Pharmaceutical Research and Development, 2(3): 1-14.
Kaushik et al., 2014 "Recent patents and patented technology platforms for pharmaceutical taste masking" Recent Pat Drug Deliv Formul. 8:37-45.
Lawless et al., 2010 "Sensory Evaluation of Food: Principles and Practice" Springer Science & Business Media, DOI: 10.1007/978-1-4419-6488-5.
Lim J, 2011 "A review of methods and theory" Food Quality and Preference, 22(8): 733-747.
Matthew et al., "Stability of metronidazole benzoate in suspensions" J Clin Pharm Ther. 19:31-34, 1994.
Pfizer, 2015. FLAGYL® (metronidazole) tablets—Prescribing Information. LAB-0162-6.2. Revised Jun. 2015.
Ramasamy et al., 2011 "Formulation and evaluation of xantham gum based aceclofenac tablets for colon targeted drug delivery" Brazilian Journal of Pharmaceutical Sciences, 47:299-311.
Rowe et al., 2009, Handbook of Pharmaceutical Excipients, Sixth Edition, The Pharmaceutical Press, 888 p.
Sana et al., 2012 "Formulation and evaluation of taste masked oral suspension of dextromethorphan hydrobromide" Int J Drug Dev Res. 4:159-172.
Sanofi-Aventis, 2016. FLAGYL® (metronidazole) capsules. Product Monograph. Submission Control No. 197442. s-a Version 7.0. Revised Nov. 3, 2016.
Sharma et al., 2010 "Taste masking technologies: a review" Int J Pharm Sci. 2(2):6-13.
Sohi et al., 2004 "Taste masking technologies in oral pharmaceuticals: recent developments and approaches" Drug Dev Ind Pharm, 30(5):429-448.
Tsuji et al., 2006 "Evaluation of bitterness suppression of macrolide dry syrups by jellies" Chem Pharm Bull. 54:310-314.
Zietsman et al., 2005 "An Investigation into the Development of a Stable Aqueous Suspension of Metronidazole Benzoate for Oral Use".
Zietsman et al., 2007 "Formulation Development and Stability Studies of Aqueous Metronidazole Benzoate Suspensions Containing Various Suspending Agents" Drug Development and Industrial Pharmacy, 33:191-197.
Sanofi, 2013, "Flagyl Suspension Information Leaflet" Old Health, Package Insert.
Kumar et al., 2012, "Recent Trends In Taste Masking Of Bitter Drugs," Journal of Drug Delivery Research 1(1):1-9.

* cited by examiner

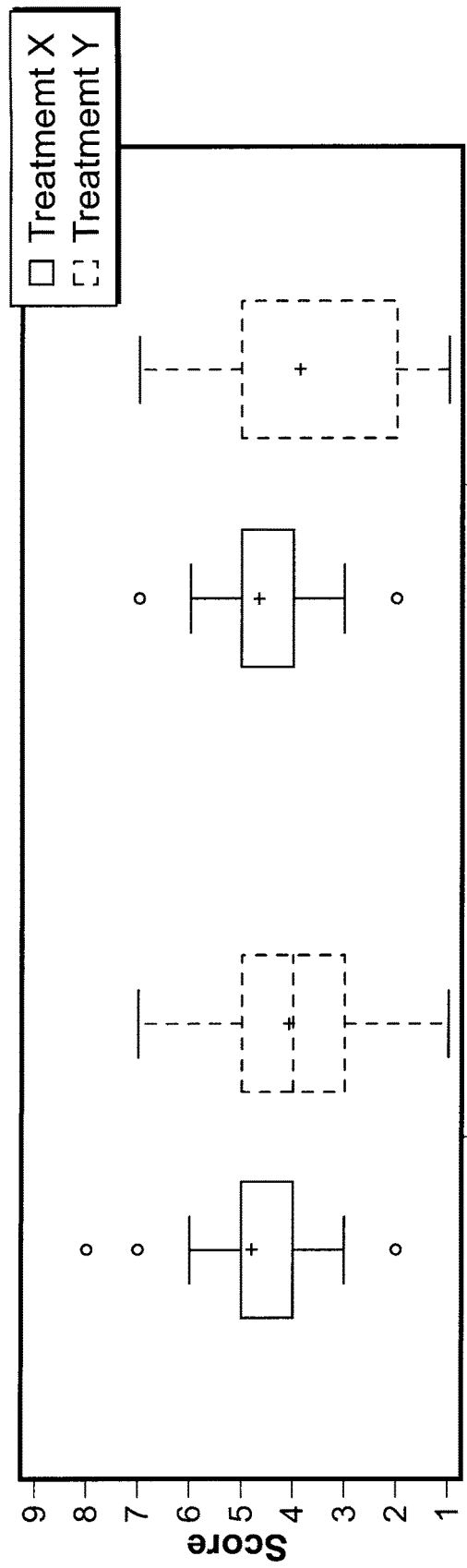
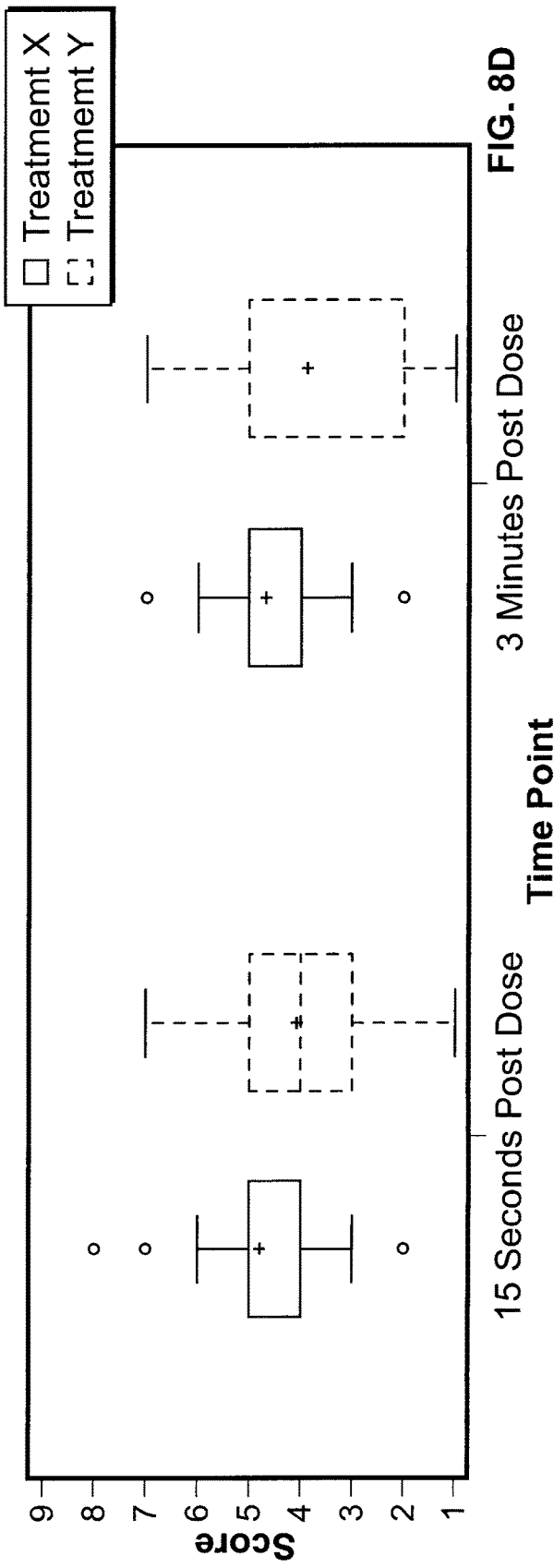

ORAL FORMULATIONS OF METRONIDAZOLE AND METHODS OF TREATING AN INFECTION USING SAME

CROSS REFERENCE TO PRIOR APPLICATIONS

This application is a continuation of U.S. application Ser. No. 16/959,356, which is a § 371 national stage application of international application no. PCT/CA2019/050053, filed Jan. 16, 2019, which claims priority under the Paris Convention to U.S. Provisional Patent Application 62/617,703, filed Jan. 16, 2018, each of which is incorporated herein by reference as if set forth in its entirety.

TECHNICAL FIELD

The present disclosure relates to taste masking of a pharmaceutical compound. More specifically, the present disclosure relates to taste-masked oral compositions comprising metronidazole and methods for treating infection in patients using these compositions.

BACKGROUND

Metronidazole is a synthetic nitroimidazole antimicrobial that is used for treating a variety of infections. For example, metronidazole has been shown to be effective in the treatment of bacterial infections (including Gram-positive and Gram-negative infections), fungal infections, and protozoal infections. Approved indications for metronidazole include bacterial vaginosis, trichomoniasis, and amebiasis (in which oral metronidazole is a first line therapy) as well as anaerobic bacterial infections and bacterial infections of specific organ systems (in which intravenous (IV) metronidazole is a first line therapy with a step-down approach to oral formulations). There are also several off-label uses of metronidazole. Metronidazole is an effective treatment option for *Clostridium difficile* infection (CDI) and is a first-line therapy for treatment of mild-to-moderate CDI in pediatric patients.

An oral formulation of metronidazole tablets is sold under the trade name Flagyl™ An extended release metronidazole tablet is sold under the trade name Flagyl™ ER. A metronidazole capsule is sold under the trade name Flagyl™ Capsule.

For some patients, administration of metronidazole tablets and/or capsules is difficult or impossible for one or more reasons. For example, metronidazole is bitter and may leave a user with an unpleasant metallic aftertaste. The bitterness and/or aftertaste of metronidazole may be sufficient to deter a patient from complying with their dosing regimen. Some patients encounter compliance issues with metronidazole tablets and/or capsules due to dysphagia, which is a difficulty swallowing. Dysphagia is common in pediatric and geriatric patients in particular. One recommendation for administering drugs to dysphagic patients involves crushing solid-form dosages or opening capsules to access the capsule contents and administering same to the patient. Optionally, the crushed tablet or capsule contents may be combined with food or drink to make the drug more palatable. For example, a survey of over 250 pediatricians and primary care physicians indicated that metronidazole is frequently prescribed as a first-line therapy for mild to moderate *C. difficile* infections in children between the ages of 1 and 16 and that most physicians recommended that metronidazole be crushed and resuspended in juice or other liquid. Over half of the physicians surveyed experienced problems with children taking metronidazole in tablet or capsule form, including problems with both unpleasant taste and swallowing the medication. Similarly, a recent survey of family practice physicians, general practitioners, geriatricians, and internal medicine physicians that had prescribed metronidazole in the past year to adults age 65 and over who have trouble swallowing showed that the main recommendation for administering metronidazole to this patient population is to crush and suspend the drug in liquid or to mix the drug with food (recommended 79% of the time).

In general, oral liquid dosage forms may be used to address drug non-compliance due to dysphagia; however, it is difficult to formulate bitter drugs into palatable oral liquid dosage forms. The primary strategies used to improve drug palatability include masking the taste of drugs by adding sweeteners, flavors, and/or effervescent agents, or implementing a mechanism to limit or delay the contact between the bitter drugs and a patient's taste buds (e.g. using coatings, microencapsulation, adsorbant additives, ion exchange resins, or viscous delivery vehicles). These strategies are often used in combination, and the approach to taste masking is tailored to each individual drug. The choice of taste-masking strategy depends on several factors such as the extent of the bitter taste of the Active Pharmaceutical Ingredient (API), dose levels, solubility and ionic characteristics, desired bioavailability, and required dosage form (Kalaskar 2014, Bhattacharjee 2016). Although understanding these characteristics is useful in formulating a taste-masked formulation, finding an appropriate taste-masking approach is not straight-forward.

Efforts have been made to compound metronidazole into a more palatable formulation by using suspending and sweetening agents, but the bitter, pungent aftertaste remains (Gee 2007). One option for administration of bad-tasting drugs is to compound the drug in a vehicle that is palatable or favored by the patient (e.g., chocolate sauce, apple sauce, ice cream, juice). This can be performed at a compounding pharmacy or by a caregiver. The challenge with this option is that pharmacist or caregiver compounding of current formulations may result in loss of API, which may lead to under-dosed finished drug products, thereby annulling any beneficiary therapeutic effects for the patient (D'Hondt 2014).

Another strategy for taste-masking is altering the molecular structure of an API to change its taste. This strategy has been applied to metronidazole and results in metronidazole benzoate (also called benzoyl metronidazole), which is available in some countries in a suspension marketed as Flagyl™ S Suspension or Norzol™ Oral suspension. The molecular difference between metronidazole and metronidazole benzoate is the addition of an ester group in the metronidazole benzoate; the bland taste of the ester is predicted to mask the bitter aftertaste that is commonly associated with metronidazole, thereby making the suspension more palatable and easier to administer to specific populations (i.e., pediatrics) (Matthew 1994, Bempong 2005). Substitution of the metronidazole benzoate suspension for the metronidazole tablet may not be appropriate in many instances, at least because there is evidence to suggest that metronidazole benzoate is absorbed at a slower rate, resulting in delayed peak plasma concentrations, which makes it inappropriate for use in various patients and infections, including, for example, acute infections.

For example, Houghton et al. (1982) compared the pharmacokinetics of metronidazole and its principle oxidative metabolites after administration of benzoyl metronidazole (equivalent to 2 g or 400 mg of metronidazole) or a 400 mg dose of metronidazole and concluded that the absorption of metronidazole into systemic circulation was markedly slower following treatment with benzoyl metronidazole than after dosing with metronidazole. Moreover, given the difference in observed $C_{max}$ between metronidazole and benzoyl metronidazole, and the difference in the time to achieve $C_{max}$ between the two formulations, the use of benzoyl metronidazole would not be sufficient for use in the case of acute microbial infections, and therefore cannot be considered a therapeutically equivalent substitution for the oral tablet form of metronidazole.

Matthew et al. (1994) examined the stability of two suspensions (16.0 mg/ml) of metronidazole benzoate in two commercially available products and found that metronidazole benzoate was not hydrolyzed in the gut through an acidic/hydrolysis reaction and thus suggested that the metronidazole benzoate suspension should not be readily substituted for metronidazole tablets in the treatment of local gastrointestinal infections. This study was substantiated by similar results reported from others (e.g., Bempong 2005).

These caveats have made their way to the label of the Flagyl™ S Suspension marketed under the Therapeutic Goods Administration in Australia. The label (Sanofi Aventis 2016) in this regulatory jurisdiction specifically states that metronidazole benzoate is not systemically available following oral administration. The overview of pharmacokinetics caution that total absorption from metronidazole benzoate suspension is somewhat lower than from tablets, and the time to reach peak serum level is quite variable (3.6 to 5.1 hours), particularly in children. The label also states that because of the slow absorption and delayed peak plasma level, Flagyl S Suspension™ is not recommended for use in the acute situation of anaerobic infection.

It is an object of the present disclosure to mitigate and/or obviate one or more of the above deficiencies.

SUMMARY OF THE DISCLOSURE

The disclosure relates to oral pharmaceutical compositions of metronidazole with one or more improved taste properties. The disclosure also relates to methods of treating an infection in a patient using the oral pharmaceutical compositions disclosed herein.

In certain aspects, the disclosure relates to an oral pharmaceutical composition comprising a) metronidazole or a pharmaceutically acceptable salt thereof; and b) magnesium aluminum silicate.

In certain aspects, the disclosure relates to an oral pharmaceutical composition comprising a) metronidazole or a pharmaceutically acceptable salt thereof; b) magnesium aluminum silicate; c) and at least one flavoring agent.

In some embodiments, the oral pharmaceutical composition is a liquid pharmaceutical composition, a suspension, or a solution.

In some embodiments, metronidazole is present at a concentration of from about 50 milligrams (mg) to about 500 mg per milliliter (ml), from about 100 milligrams (mg) to about 500 mg per 5 ml, from about 200 milligrams (mg) to about 500 mg per 5 ml, from about 250 milligrams (mg) to about 500 mg per 5 ml, from about 250 milligrams (mg) to about 400 mg per 5 ml, or about 250 mg per 5 ml of the oral pharmaceutical composition.

In some embodiments, the concentration of magnesium aluminum silicate is between 1% and 10% (w/v), between 5% and 10% (w/v), between 1% and 5% (w/v), is between 1% and 2% (w/v) or is no more than 6.4% (w/v) of the oral pharmaceutical composition.

In some embodiments, the magnesium aluminum silicate is a natural product. In some embodiments, the magnesium aluminum silicate is synthetic.

In some embodiments, the magnesium aluminum silicate is VEEGUM™ brand, VEEGUM™ HV, VEEGUM™ PRO, VEEGUM™ PURE or VEEGUM™ R.

In some embodiments, the concentration of VEEGUM™ HV is no more than 1.2% (w/v) or is 1.2% (w/v) of the oral pharmaceutical composition.

In some embodiments the magnesium aluminum silicate is magnesium aluminometasilicate.

In some embodiments, the magnesium aluminum silicate is Neusilin.

In some embodiments, the magnesium aluminum silicate is Neusilin UF12.

In some embodiments, the oral pharmaceutical compositions further comprise one or more sweeteners.

In some embodiments, the sweetener is a natural sweetener.

In some embodiments, the natural sweetener is sucrose, glucose, fructose, stevia, or mixtures thereof.

In some embodiments, the natural sweetener is sucrose.

In some embodiments, concentration of sucrose is between 25% and 85% (w/v), is between 40% and 60% (w/v), is no more than 60% (w/v), is no more than 72% (w/v), is no more than 82% (w/v), is no more than 50% (w/v), or is 50% (w/v) of the oral pharmaceutical composition.

In some embodiments, the natural sweetener is glucose.

In some embodiments, the concentration of glucose is between 30% and 70% (w/v), is no more than 40% (w/v), is no more than 50% (w/v), or is no more than 62% (w/v) of the oral pharmaceutical composition.

In some embodiments, the natural sweetener is fructose.

In some embodiments, the concentration of fructose is between 1% and 40% (w/v), is no more than 2% (w/v), or is no more than 35% (w/v) of the oral pharmaceutical composition.

In some embodiments, the natural sweetener is stevia.

In some embodiments, the sweetener is an artificial sweetener.

In some embodiments, the artificial sweetener is sucralose, sorbitol, saccharin, aspartame, acesulfame potassium, neotame, advantame, or mixtures thereof.

In some embodiments, the artificial sweetener is sucralose.

In some embodiments, the concentration of sucralose is between 0.1% and 10% (w/v), is between 0.1% and 2% (w/v), is no more than 5% (w/v), is no more than 1.1% (w/v), is no more than 0.25% (w/v), or is 0.25% (w/v) of the oral pharmaceutical composition.

In some embodiments, the artificial sweetener is sorbitol.

In some embodiments, the concentration of sorbitol is between 50% and 99% (w/v), or is no more than 90% (w/v) of the oral pharmaceutical composition.

In some embodiments, the artificial sweetener is saccharin.

In some embodiments, the concentration of saccharin is between 3.5 mg/5 mL and 10 mg/1 mL of the oral pharmaceutical composition.

In some embodiments, the saccharin is saccharine sodium.

In some embodiments, the concentration of saccharine sodium is between 1% and 10% (w/v), is between 0.1% and 2% (w/v), is no more than 1.4% (w/v), is no more than 0.25% (w/v), is 0.25% (w/v), is no more than 3% (w/v), or is no more than 5% (w/v) of the oral pharmaceutical composition.

In some embodiments, the saccharin is saccharine calcium.

In some embodiments, the concentration of saccharine calcium is no more than 0.01% (w/v), or no more than 17.5 mg/5 mL of the oral pharmaceutical composition.

In some embodiments, the artificial sweetener is aspartame.

In some embodiments, the concentration of aspartame is between 20% and 60% (w/v), or is no more than 40% (w/v) of the oral pharmaceutical composition.

In some embodiments, the artificial sweetener is acesulfame potassium.

In some embodiments, the concentration of acesulfame potassium is between 0.1% and 1% (w/v), is no more than 0.15% (w/v), or is no more than 0.5% (w/v) of the oral pharmaceutical composition.

In some embodiments, the artificial sweetener is neotame.

In some embodiments, the artificial sweetener is advantame.

In some embodiments, the at least one flavoring agents is selected from the group consisting of natural flavors, artificial flavors, mint, and mixtures thereof.

In some embodiments, the natural flavor is a natural fruit flavor.

In some embodiments, the natural fruit flavor is lemon.

In some embodiments, the concentration of lemon is no more than 9% (v/v) of the oral pharmaceutical composition.

In some embodiments, the natural fruit flavor is orange.

In some embodiments, the concentration of orange is no more than 1.5% (v/v) of the oral pharmaceutical composition.

In some embodiments, the natural fruit flavor is lime.

In some embodiments, the concentration of lime is no more than 5% (v/v) of the oral pharmaceutical composition.

In some embodiments, the natural fruit flavor is apricot.

In some embodiments, the concentration of apricot is no more than 0.5% (v/v) of the oral pharmaceutical composition.

In some embodiments, the natural fruit flavor is grapefruit.

In some embodiments, the concentration of grapefruit is no more than 1.5% (v/v) of the oral pharmaceutical composition.

In some embodiments, the natural fruit flavor is banana.

In some embodiments, the concentration of banana is no more than 0.5% (v/v) of the oral pharmaceutical composition.

In some embodiments, the natural fruit flavor is cherry.

In some embodiments, the concentration of cherry is no more than 5% (v/v) of the oral pharmaceutical composition.

In some embodiments, the natural fruit flavor is apple.

In some embodiments, the concentration of apple is no more than 1% (v/v) of the oral pharmaceutical composition.

In some embodiments, the natural fruit flavor is pineapple.

In some embodiments, the concentration of pineapple is no more than 1% (v/v) of the oral pharmaceutical composition.

In some embodiments, the natural fruit flavor is grape.

In some embodiments, the concentration of grape is no more than 1% (v/v) of the oral pharmaceutical composition.

In some embodiments, the natural fruit flavor is strawberry.

In some embodiments, the concentration of strawberry is no more than 4% (v/v), no more than 1.0% (v/v), no more than 0.4% (v/v), no more than 0.2% (v/v), or is 0.1% (v/v) of the oral pharmaceutical composition.

In some embodiments, the natural fruit flavor is raspberry.

In some embodiments, the concentration of raspberry is no more than 7% (v/v), is between 0.2% and 0.8% (v/v), is no more than 0.5% (v/v), or is 0.4% (v/v) of the oral pharmaceutical composition.

In some embodiments, the natural fruit flavor is tutti frutti.

In some embodiments, the concentration of tutti frutti is no more than 0.5% (v/v) of the oral pharmaceutical composition.

In some embodiments, the natural fruit flavor is fruit punch.

In some embodiments, the concentration of fruit punch is no more than 18% (v/v) of the oral pharmaceutical composition.

In some embodiments, the artificial flavor is an artificial fruit flavor.

In some embodiments, the artificial fruit flavor is selected from the group consisting of lemon, orange, lime, apricot, grapefruit, banana, cherry, apple, pineapple, grape, strawberry, raspberry, tutti frutti, and fruit punch.

In some embodiments, the artificial fruit flavor is lemon.

In some embodiments, the concentration of lemon is no more than 9% (v/v) of the oral pharmaceutical composition.

In some embodiments, the artificial fruit flavor is orange.

In some embodiments, the concentration of orange is no more than 1.5% (v/v) of the oral pharmaceutical composition.

In some embodiments, the artificial fruit flavor is lime.

In some embodiments, the concentration of lime is no more than 5% (v/v) of the oral pharmaceutical composition.

In some embodiments, the artificial fruit flavor is apricot.

In some embodiments, the concentration of apricot is no more than 0.5% (v/v) of the oral pharmaceutical composition.

In some embodiments, the artificial fruit flavor is grapefruit.

In some embodiments, the concentration of grapefruit is no more than 1.5% (v/v) of the oral pharmaceutical composition.

In some embodiments, the artificial fruit flavor is banana.

In some embodiments, the concentration of banana is no more than 0.5% (v/v) of the oral pharmaceutical composition.

In some embodiments, the artificial fruit flavor is cherry.

In some embodiments, the concentration of cherry is no more than 5% (v/v) of the oral pharmaceutical composition.

In some embodiments, the artificial fruit flavor is apple.

In some embodiments, the concentration of apple is no more than 1% (v/v) of the oral pharmaceutical composition.

In some embodiments, the artificial fruit flavor is pineapple.

In some embodiments, the concentration of pineapple is no more than 1% (v/v) of the oral pharmaceutical composition.

In some embodiments, the artificial fruit flavor is grape.

In some embodiments, the concentration of grape is no more than 1% (v/v) of the oral pharmaceutical composition.

In some embodiments, the artificial fruit flavor is strawberry.

In some embodiments, the concentration of strawberry is no more than 4% (v/v), no more than 1.0% (v/v), no more than 0.4% (v/v), no more than 0.2% (v/v), or is 0.1% (v/v) of the oral pharmaceutical composition.

In some embodiments, the artificial fruit flavor is raspberry.

In some embodiments, the concentration of raspberry is no more than 7% (v/v), is between 0.2% and 0.8% (v/v), is no more than 0.5% (v/v), or is 0.4% (v/v) of the oral pharmaceutical composition.

In some embodiments, the artificial fruit flavor is tutti frutti.

In some embodiments, the concentration of tutti frutti is no more than 0.5% (v/v) of the oral pharmaceutical composition.

In some embodiments, the artificial fruit flavor is fruit punch.

In some embodiments, the concentration of fruit punch is no more than 18% (v/v) of the oral pharmaceutical composition.

In some embodiments, the flavoring agent is mint.

In some embodiments, the mint is peppermint.

In some embodiments, the concentration of peppermint is between 0.01% and 2.0% (v/v), between 0.1% and 1.0% (v/v), between 0.1% and 0.2%, less than or equal to 0.2% (v/v) or is 0.2% (v/v) of the oral pharmaceutical composition.

In some embodiments, the mint is peppermint oils.

In some embodiments, the concentration of peppermint oils is between 0.01% and 2.0% (v/v), between 0.1% and 1.0% (v/v), between 0.1% and 0.2%, less than or equal to 0.2% (v/v), or is 0.2% (v/v) of the oral pharmaceutical composition.

In some embodiments, the one or more flavoring agents comprise strawberry.

In some embodiments, the concentration of strawberry is no more than 4% (v/v), no more than 1.0% (v/v), no more than 0.4%, or is 0.1% (v/v) of the oral pharmaceutical composition. In some embodiments, the concentration of strawberry is no more than 4% (w/v), no more than 1.0% (w/v), no more than 0.4%, or is 0.1% (w/v) of the oral pharmaceutical composition.

In some embodiments, the one or more flavoring agents comprise raspberry.

In some embodiments, the concentration of raspberry is no more than 7% (v/v) or is 0.4% (v/v) of the oral pharmaceutical composition.

In some embodiments, the one or more flavoring agents comprise strawberry and raspberry.

In some embodiments, the concentration of strawberry is 0.1% (v/v) of the oral pharmaceutical composition and the concentration of raspberry is 0.4% (v/v) of the oral pharmaceutical composition.

In some embodiments, the one or more flavoring agents comprise strawberry and peppermint.

In some embodiments, the concentration of strawberry is 0.1% (v/v) of the oral pharmaceutical composition and the concentration of peppermint is 0.2% (v/v) of the oral pharmaceutical composition.

In some embodiments, the concentration of strawberry is about 0.4% (w/v) of the oral pharmaceutical composition and the concentration of peppermint is about 0.2% (w/v) of the oral pharmaceutical composition.

In some embodiments, the one or more flavoring agents comprise strawberry and peppermint oils.

In some embodiments, the concentration of strawberry is 0.1% (v/v) of the oral pharmaceutical composition and the concentration of peppermint oils is 0.2% (v/v) of the oral pharmaceutical composition.

In some embodiments, the concentration of strawberry is about 0.4% (w/v) of the oral pharmaceutical composition and the concentration of peppermint oils is about 0.2% (w/v) of the oral pharmaceutical composition.

In some embodiments, the one or more flavoring agents comprise raspberry and peppermint.

In some embodiments, the concentration of raspberry is 0.4% (v/v) of the oral pharmaceutical composition and the concentration of peppermint is 0.2% (v/v) of the oral pharmaceutical composition.

In some embodiments, the one or more flavoring agents comprise raspberry and peppermint oils.

In some embodiments, the concentration of raspberry is 0.4% (v/v) of the oral pharmaceutical composition and the concentration of peppermint oils is 0.2% (v/v) of the oral pharmaceutical composition.

In some embodiments, the one or more flavoring agents comprise strawberry, raspberry, and peppermint.

In some embodiments, the concentration of strawberry is 0.1% (v/v) of the oral pharmaceutical composition, the concentration of raspberry is 0.4% (v/v) of the oral pharmaceutical composition, and the concentration of peppermint is 0.2% (v/v) of the oral pharmaceutical composition.

In some embodiments, the one or more flavoring agents comprise strawberry, raspberry, and peppermint oils.

In some embodiments, the concentration of strawberry is 0.1% (v/v) of the oral pharmaceutical composition, the concentration of raspberry is 0.4% (v/v) of the oral pharmaceutical composition, and the concentration of peppermint oils is 0.2% (v/v) of the oral pharmaceutical composition. In some embodiments, the one or more flavoring agents comprise strawberry, raspberry, peppermint, peppermint oils, and mixtures thereof.

In some embodiments, the oral pharmaceutical composition comprises one or more excipients.

In some embodiments, the one or more excipients comprises one or more of a preservative, a buffer, a viscosity agent, and a solvent. In some embodiments, the preservative comprises one or more of amino aryl acid ester, aryl acid, alkyl acid, amino aryl acid ester/organic acid, and combinations thereof.

In some embodiments, the preservative comprises an amino aryl acid ester.

In some embodiments, the amino aryl acid ester is methyl paraben, ethyl paraben, propyl paraben, or combinations thereof.

In some embodiments, the amino aryl acid ester is methyl paraben. In some embodiments, the concentration of methyl paraben is between 0.01% and 20% (w/v), is between 0.1% and 0.2% (w/v), is no more than 0.2% (w/v), is no more than 5% (w/v), is no more than 13% (w/v), is no more than 0.15% (w/v), or is 0.15% (w/v) of the oral pharmaceutical composition.

In some embodiments, the amino aryl acid ester is ethyl paraben.

In some embodiments, the concentration of ethyl paraben is between 0.6 mg/5 mL and 2 mg/5 mL.

In some embodiments, the amino aryl acid ester is propyl paraben.

In some embodiments, the concentration of propyl paraben is between 0.01% and 40% (w/v), is between 0.01% and 0.5% (w/v), is no more than 0.06% (w/v), is no more than 10% (w/v), is no more than 36% (w/v), is no more than 0.2% (w/v), or is 0.2% (w/v) or 0.02% of the oral pharmaceutical composition.

In some embodiments, the preservative comprises an aryl acid.

In some embodiments, the aryl acid is sodium benzoate, benzoic acid, or a combination thereof.

In some embodiments, the aryl acid is sodium benzoate.

In some embodiments, the concentration of sodium benzoate is between 0.01% and 10% (w/v), is no more than 0.2% (w/v), is no more than 1% (w/v), or is no more than 5% (w/v) of the oral pharmaceutical composition.

In some embodiments, the aryl acid is benzoic acid.

In some embodiments, the concentration of benzoic acid is between 0.01% and 10% (w/v), is no more than 0.1% (w/v), is no more than 0.5% (w/v), or is no more than 0.7% (w/v) of the oral pharmaceutical composition.

In some embodiments, the preservative comprises an alkyl acid.

In some embodiments, the alkyl acid is sorbic acid, potassium sorbate, propionic acid, or a combination thereof.

In some embodiments, the alkyl acid is sorbic acid.

In some embodiments, the concentration of sorbic acid is between 0.01% and 1% (w/v), is no more than 0.01% (w/v), is no more than 0.1% (w/v), or is no more than 0.5% (w/v) of the oral pharmaceutical composition.

In some embodiments, the alkyl acid is potassium sorbate.

In some embodiments, the concentration of potassium sorbate is between 0.01% and 1% (w/v), or is no more than 0.65% (w/v) of the oral pharmaceutical composition.

In some embodiments, the alkyl acid is propionic acid.

In some embodiments, the preservative comprises an amino aryl acid ester/organic acid.

In some embodiments, the amino aryl acid ester/organic acid is a methyl paraben/sodium benzoate combination.

In some embodiments, the buffer comprises one or more of an acetate, a citrate, sodium phosphate monobasic, sodium phosphate dibasic, or a combination thereof.

In some embodiments, the buffer comprises an acetate.

In some embodiments, the acetate is acetic acid, sodium acetate, or a combination thereof.

In some embodiments, the acetate is acetic acid.

In some embodiments, the concentration of acetic acid is no more than 0.1% (w/v) of the oral pharmaceutical composition.

In some embodiments, the acetate is sodium acetate.

In some embodiments, the concentration of sodium acetate is no more than 0.1% (w/v) of the oral pharmaceutical composition.

In some embodiments, the buffer comprises a citrate.

In some embodiments, the citrate is citric acid, sodium citrate, sodium hydroxide, hydrochloric acid, or a combination thereof.

In some embodiments, the citrate is citric acid.

In some embodiments, the concentration of citric acid is between 0.1% and 75% (w/v), is no more than 0.18% (w/v), is no more than 0.8% (w/v), or is no more than 72% (w/v) of the oral pharmaceutical composition.

In some embodiments, the citrate is sodium citrate.

In some embodiments, the concentration of sodium citrate is between 0.01% and 40% (w/v), no more than 0.1% (w/v), no more than 1.1% (w/v), or is no more than 32% (w/v) of the oral pharmaceutical composition.

In some embodiments, the citrate is sodium hydroxide.

In some embodiments, the concentration of sodium hydroxide is no more than 40% (w/v) of the oral pharmaceutical composition.

In some embodiments, the citrate is hydrochloric acid.

In some embodiments, the concentration of hydrochloric acid is no more than 10% (w/v) of the oral pharmaceutical composition.

In some embodiments, the buffer comprises sodium phosphate monobasic.

In some embodiments, concentration of sodium phosphate monobasic is between 0.01% and 2% (w/v), is between 0.01% and 0.5% (w/v), is no more than 0.2% (w/v), is 0.2% (w/v), is no more than 0.5% (w/v), or is no more than 1.2% (w/v) of the oral pharmaceutical composition.

In some embodiments, the buffer comprises sodium phosphate dibasic.

In some embodiments, the concentration of sodium phosphate dibasic is between 0.01% and 5% (w/v), is between 0.01% and 0.5% (w/v), is no more than 0.2% (w/v), is 0.2% (w/v), is no more than 1.3% (w/v), or is no more than 2% (w/v) of the oral pharmaceutical composition.

In some embodiments, the viscosity agent comprises one or more of a cellulose derivative, an anionic, or combinations thereof.

In some embodiments, the viscosity agent is a cellulose derivative.

In some embodiments, the cellulose derivative is one or more of microcrystalline cellulose, methylcellulose, hydroxyethylcellulose, hydroxypropylcellulose, or a combination thereof.

In some embodiments, the cellulose derivative is microcrystalline cellulose.

In some embodiments, the concentration of microcrystalline cellulose is between 0.1% and 5% (w/v), is between 0.1% and 1.0% (w/v), is no more than 0.60% (w/v), is 0.60% (w/v), or is no more than 1.4% (w/v) of the oral pharmaceutical composition. In some embodiments, the cellulose derivative is methylcellulose.

In some embodiments, the concentration of methylcellulose is no more than 0.025% (w/v) of the oral pharmaceutical composition.

In some embodiments, the cellulose derivative is hydroxyethylcellulose.

In some embodiments, the concentration of hydroxyethylcellulose is between 0.1% and 10% (w/v), is no more than 0.1% (w/v), is no more than 0.7% (w/v), or is no more than 10% (w/v) of the oral pharmaceutical composition.

In some embodiments, the cellulose derivative is hydroxypropylcellulose.

In some embodiments, the concentration of hydroxypropylcellulose is between 0.1% and 10% (w/v), is no more than 0.5% (w/v), is no more than 2% (w/v), or is no more than 5% (w/v) of the oral pharmaceutical composition.

In some embodiments, the viscosity agent is an anionic.

In some embodiments, the anionic is sodium alginate.

In some embodiments, the concentration of sodium alginate is between 0.1% and 1% (w/v), is no more than 0.1% (w/v), or is no more than 0.3% (w/v) of the oral pharmaceutical composition.

In some embodiments, the solvent comprises one or more of glycerol, alcohol, propylene glycol, or a combination thereof.

In some embodiments, the solvent is glycerol.

In some embodiments, the concentration of glycerol is between 5% and 99% (w/v), is between 5% and 20% (w/v), is no more than 10% (w/v), is 10% (w/v), is no more than 70% (w/v), or is no more than 94% (w/v) of the oral pharmaceutical composition.

In some embodiments, the solvent is alcohol.

In some embodiments, the concentration of alcohol is less than or equal to 0.5% (v/v), between 0.1% (v/v) and 0.5% (v/v), or about 0.1% (v/v), of the oral pharmaceutical composition.

In some embodiments, the solvent is propylene glycol.

In some embodiments, the concentration of propylene glycol is between 1% and 99% (w/v), between 6.5% and 13% (w/v), is no more than 5% (w/v), is no more than 10% (w/v), or is no more than 92% (w/v) of the oral pharmaceutical composition.

In some embodiments, the oral pharmaceutical composition comprises water.

In certain aspects the invention relates to an oral pharmaceutical composition comprising: metronidazole, sucrose, glycerin (glycerol), purified water, magnesium aluminum silicate, microcrystalline cellulose, sucralose, sodium phosphate, one or more preservatives, a strawberry flavoring agent and a peppermint flavoring agent.

In some embodiments, the metronidazole is present at about 250 milligrams (mg)/5 milliliters (mL) (50 mg/mL).

In some embodiments, the sucrose is present at about 50% weight/volume (w/v).

In some embodiments, the glycerin is present at about 10% w/v.

In some embodiments, the magnesium aluminum silicate is Type 1C (e.g., Veegum™ HV). In some embodiments, the magnesium aluminum silicate Type 1C is present at about 1.200% w/v.

In some embodiments, the microcrystalline cellulose is Avicel PH-101. In some embodiments the microcrystalline cellulose is present at about 0.600% w/v.

In some embodiments, the sucralose is present at 0.250% w/v.

In some embodiments the sodium phosphate is sodium phosphate (monobasic/dibasic). In some embodiments each of the sodium phosphate monobasic and the sodium phosphate dibasic is present at about 0.200% w/v.

In some embodiments, the one or more preservatives are methyl paraben and propyl paraben. In some embodiments, the methyl paraben is present at about 0.150% w/v and the propyl paraben is present at about 0.020% w/v.

In some embodiments the strawberry flavoring agent is Kidazzle™ strawberry. In some embodiments the Kidazzle™ strawberry is present at about 0.400% volume/volume (w/v).

In some embodiments, the peppermint flavoring agent is natural peppermint flavor WONF. In some embodiments, the natural peppermint flavor WONF is present at about 0.200% w/v.

In some embodiments the amount of purified water is QS to 1 liter.

In some embodiments, the oral pharmaceutical composition is a liquid pharmaceutical composition, a suspension, or a solution. In some preferred embodiments the oral pharmaceutical composition is a suspension.

In certain aspects the disclosure relates to a method of treating an infection in a patient, the method comprising the step of administering to the patient an effective amount of an oral pharmaceutical composition comprising a) metronidazole or a pharmaceutically acceptable salt thereof; and b) magnesium aluminum silicate.

In certain aspects the disclosure relates to a method of treating an infection in a patient, the method comprising the step of administering to the patient an effective amount of an oral pharmaceutical composition comprising a) metronidazole or a pharmaceutically acceptable salt thereof; b) magnesium aluminum silicate; and c) at least one flavoring agent.

In some embodiments, the oral pharmaceutical compositions are as described herein.

In some embodiments, the infection is a bacterial infection.

In some embodiments, the bacterial infection is caused by a gram-positive bacteria, a gram-negative bacteria, an aerobic bacteria, an anaerobic bacteria, a *Clostridium* species, a *Eubacterium* species, a Peptococcus species, a *Peptostreptococcus* species, a member of *Bacteroides fragilis* group, a *Fusobacterium* species, a *Prevotella* species, or *Clostridium difficile*.

In some embodiments, the infection is a fungal infection.

In some embodiments, the infection is a protozoan infection.

In some embodiments, the protozoan infection is caused by *Entamoeba histolytica*, or *Trichomonas vaginalis*.

In some embodiments, the infection is amebiasis, pelvic inflammatory disease, endocarditis, bacterial vaginosis, dracunculiasis, giardiasis, or trichomoniasis.

In some embodiments, the oral pharmaceutical composition is administered to the patient once per day (QD) (e.g., every 24 hours), twice per day (BID) (e.g., every 12 hours), three times per day (TID) (e.g., every 8 hours), or four times per day (QID) (e.g., every 6 hours). For example, the oral pharmaceutical composition is administered to the patient such that a desired total daily dosage of the composition is achieved.

In some embodiments, the effective amount of the oral pharmaceutical composition is between 250 mg and 4000 mg, between 500 mg and 4000 mg, between 1000 mg and 4000 mg, between 1500 mg and 4000 mg, between 2000 mg and 4000 mg, between 200 mg and 2000 mg, between 250 mg and 2000 mg, between 500 mg and 2000 mg, between 750 mg and 2000 mg, between 1000 mg and 2000 mg, between 1250 mg and 2000 mg, or between 1500 mg and 2000 mg of metronidazole as a single daily dose, or a total daily dose.

In some embodiments, the effective amount of the oral pharmaceutical composition is between 5 mg/kg of metronidazole and 10 mg/kg or is about 5 mg/kg, about 7.5 mg/kg, or about 10 mg/kg of metronidazole administered every 6 or 8 hours to the patient.

In some embodiments, the effective amount of the oral pharmaceutical composition is between 20 mg/kg of metronidazole and 50 mg/kg, is about 20 mg/kg, about 25 mg/kg, about 30 mg/kg, about 35 mg/kg, or about 40 mg/kg of metronidazole administered daily to the patient.

In some embodiments, the patient is a geriatric patient or a pediatric patient.

In some embodiments the patient is a patient who has dysphagia.

In some embodiments, the patient is a patient who has a sensitive palate, taste sensitivity and/or a hyperactive gag reflex, which makes swallowing capsules or pills difficult or impossible.

In some embodiments, the effective amount of the oral pharmaceutical composition is between 15 mg/kg of metronidazole and 50 mg/kg, between 25 mg/kg of metronidazole and 40 mg/kg, or about 30 mg/kg of metronidazole administered to the pediatric patient.

In some embodiments, the effective amount of the oral pharmaceutical composition is no more than 2000 mg administered to the pediatric patient per day.

In some embodiments, the treatment is associated with taste-masking of the metronidazole to the patient.

In some embodiments, the taste-masking results in a more palatable taste of the metronidazole.

In some embodiments, the taste-masking results in a shorter aftertaste of the metronidazole.

In some embodiments, the taste-masking is relative to a composition of metronidazole that does not comprise a flavoring agent.

In some embodiments, the taste-masking is relative to a composition of metronidazole comprising crushed metronidazole tablets.

In some embodiments, the taste-masking is relative to a composition of metronidazole comprising a chocolate flavoring agent.

In some embodiments, the oral pharmaceutical composition is the oral pharmaceutical composition as described herein.

As demonstrated throughout the present disclosure, the inventors have discovered pharmaceutical compositions comprising metronidazole that have an unexpected improvement in one or more taste properties, such as, for example, masking (at least in part) the bitter taste of metronidazole. In some embodiments, the methods may improve patient dosing regimen compliance, improve adherence, and/or minimize side effects relative to methods that involve administration of currently available formulations of metronidazole. In some embodiments, the pharmaceutical composition provided herein is advantageous relative to a metronidazole composition compounded by a pharmacist.

The formulations of the disclosure have a number of advantages. The formulations may provide increased value yield and/or more precise dosing compared to metronidazole tablets that are compound and resuspended, for example, at a pharmacy. In addition, the metronidazole in the formulation may remain viscous throughout its shelf life to increase stability of the metronidazole, but can be remixed by simple shaking.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate some embodiments of the present invention. The invention may be better understood by reference to one or more of these drawings in combination with the detailed description of the specification embodiments presented herein.

FIG. 8C is graph of the mean (±standard deviation) Hedonic scale scores for smell at 15 seconds and 3 minutes post-dose of ATI-1501 (Treatment X; solid lines/left data for each time point) or Flagyl® (Treatment Y; dotted lines/right data for each time point). Treatment X=10 mL of ATI-1501 oral suspension at 250 mg metronidazole/5 mL; Treatment Y=500 mg Flagyl® tablet crushed in up to 30 mL of apple sauce.

FIG. 8D is a graph of the mean (±standard deviation) scores for bitterness at 15 seconds and 3 minutes post-dose of ATI-1501 (Treatment X; solid lines/left data for each time point) or Flagyl® (Treatment Y; dotted lines/right data for each time point). Treatment X=10 mL of ATI-1501 oral suspension at 250 mg metronidazole/5 mL; Treatment Y=500 mg Flagyl® tablet crushed in up to 30 mL of apple sauce.

DETAILED DESCRIPTION

Figure 1:
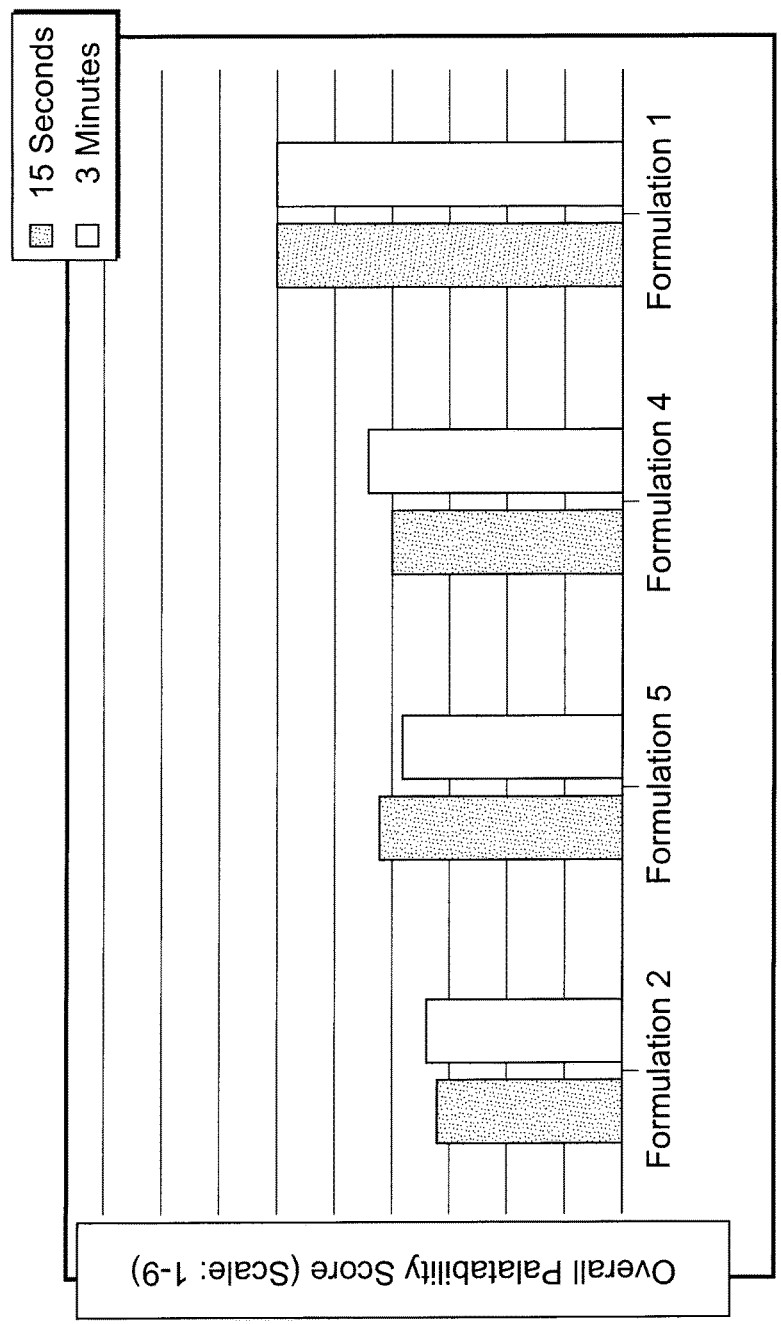
FIG. 1 shows the overall palatability score of the tested formulations (scored on a scale of 1-9; y axis) at 15 seconds (shaded bar/right bar for the time point; x axis) and 3 minutes (black bar/right bar for the time point; x axis) was directly compared between these four formulations (labeled Formula 2, Formula 5, Formula 4, Formula 1; x axis).

Some embodiments of the invention are described herein as follows.

Therapeutics that are unpalatable and have a bitter and/or metallic taste or after taste have a high degree of patient non-compliance, making taste-masking an important area of pharmaceutical research. Several taste-masking approaches and technologies have been used and reviewed (e.g., Sohi 2004, Sharma 2010, Kaushik 2014), such as addition of flavoring agents, addition of sweetening agents, microencapsulation, ion-exchange, inclusion complexation, granulation, adsorption, pro-drug development, addition of bitterness inhibitors, emulsion techniques, pH modification, gelation or enhanced viscosity, liposome entrapment, and addition of effervescent agents. Flavorings and sweeteners are not appropriate for solitary use in preparations of very bitter tasting drugs, such as metronidazole, as addition of a flavor or sweetening agent alone is insufficient at masking the taste of a very bitter drug. Further, the metronidazole benzoate suspension currently available in some countries, which includes an added ester to mask the pungent and unpleasant after taste of metronidazole (free-base), has a delayed time to peak plasma concentration and delayed in dissolution and release of the API, relative to metronidazole tablets and capsules.

The choice of taste-masking strategy depends on several factors, such as, for example, the extent of the bitter taste of the API, dose levels, solubility and ionic characteristics, desired bioavailability, and required dosage form (Kalaskar 2014, Bhattacharjee 2016). Accordingly, the practice of taste masking APIs is highly unpredictable. Typically, determining an effective taste-masking formulation requires extensive experimentation, and a skilled person cannot readily predict which taste masking strategy, or combinations thereof, will be suitable. For example, taste masking vehicles with acidic pH may amplify rather than diminish the bitter taste of macrolide antibiotics (Tsuji 2006, Ishizaka 2007). Ion exchange resins have a varying ability to diminish the bitterness of certain APIs (Sana 2012) and thus multiple resins may need to be tested for this purpose.

The present disclosure is based on the inventors' surprising discovery of a metronidazole formulation that masks, at least in part, the bitter taste of metronidazole. In some preferred embodiments, the formulation provided herein does not require additional functional groups for the purpose of taste masking. As used herein, "taste masking" refers to a perceived reduction of an undesirable taste that would otherwise exist.

Previous reports have indicated that metronidazole has a pungent taste that lingers. In some embodiments, the metronidazole formulation provided herein masks the bitter and/or metallic after taste of metronidazole. As used herein, "after taste" refers to a taste persisting after the substance that caused it is no longer present. To sufficiently mask the unpleasant taste (which some people describe as metallic), the inventors determined that it may be desirable to mask the initial pungent taste as well as the lingering after taste. In some preferred embodiments, the metronidazole formulation masks both the taste and after taste of metronidazole. As described in the Examples, to determine whether one or more formulations were sufficient to mask taste and aftertaste, the inventors asked subjects to rate the taste, smell, texture and overall palatability of the formulation at 15 seconds and 3 minutes post-administration.

In some embodiments, the metronidazole formulation provided herein is more palatable than metronidazole. As used herein, "palatable" and "palatability" refer to a degree or level of agreeability to a subject's palate. For example, a palatable substance has an agreeable taste or relationship with a subject's palate. A substance having a high level of palatability tastes relatively good, whereas a substance having a low level of palatability tastes relatively bad. The perception of "bad taste" may be due to factors other than taste, such as smell and texture. In the Examples provided herein, the inventors had subjects rate one or more formulations based on the following parameters: taste, smell, texture, and degree of bitterness, in addition to the overall palatability of each of the formulations (e.g., how pleasant is it to take this formulation?). In some embodiments the taste, smell, texture or degree of bitterness is assessed using a modified Hedonic scale.

In some embodiments, the formulations of the disclosure have a higher Hedonic scale rating as compared to a suitable reference formulation, such as a formulation containing only metronidazole base, only metronidazole base and magnesium aluminum silicate, only metronidazole and one or more flavorings, or crushed metronidazole (Flagyl®) tablets compounded in a liquid volume of applesauce or other food or drink. For example, the Hedonic scale for assessing taste, smell, or texture can be a 9-point scale. In some embodiments the formulations of the disclosure have a Hedonic scale rating that is at least 1, 2, 3, 4, 5, 6, 7, or 8 points higher as compared to a suitable reference formulation when assessed for taste, smell, or texture. In another example, the Hedonic scale for assessing bitterness can be a 3-point scale. In some embodiments the formulations of the disclosure have a Hedonic scale rating that is at least 1 or 2 points higher as compared to a suitable reference formulation when assessed for bitterness. In some embodiments the assessment of taste, smell texture, or bitterness is assessed within 30 seconds or within 15 seconds of ingesting the formulation to assess immediate taste. In some embodiments the assessment of taste, smell texture, or bitterness is assessed later, for example, more than 30 seconds, one minute, two minutes, three minutes or five minutes after ingesting the formulation to assess aftertaste.

It is contemplated herein that the pharmacokinetic profile of some embodiments of the formulation provided herein achieves or is predicted to achieve a bioavailability that is substantially equivalent to that of the tablet form of metronidazole (e.g., with no or minimal delay in achieving peak plasma concentrations). Accordingly, it is contemplated herein that some embodiments of the formulation provided herein are more efficacious then a metronidazole benzoate suspension. A skilled person will appreciate that this may be advantageous, for example, for use in the treatment of acute anaerobic infections, wherein the time to peak concentration is clinically relevant.

In an aspect of the present disclosure, an oral pharmaceutical composition is provided. The oral pharmaceutical composition comprises: 1) metronidazole or a pharmaceutically acceptable salt thereof, and magnesium aluminum silicate or 2) metronidazole or a pharmaceutically acceptable salt thereof, magnesium aluminum silicate, and at least one flavoring agent. In an aspect of the present disclosure, a method of treating an infection in a patient is provided. The method comprises a step of administering to the patient an effective amount of an oral pharmaceutical composition, as provided herein, such as, for example, an oral pharmaceutical composition comprising: 1) metronidazole or a pharmaceutically acceptable salt thereof, and magnesium aluminum silicate or 2) metronidazole or a pharmaceutically acceptable salt thereof, magnesium aluminum silicate, and at least one flavoring agent.

Pharmaceutical Composition

In an aspect of the disclosure, an oral pharmaceutical composition is provided. In an embodiment, the oral pharmaceutical composition comprises: a) metronidazole or a pharmaceutically acceptable salt thereof, and b) magnesium aluminum silicate. In another embodiment, the oral pharmaceutical composition comprises a) metronidazole or a pharmaceutically acceptable salt thereof, b) magnesium aluminum silicate, and c) at least one flavoring agent. In some embodiments, the oral pharmaceutical composition is a liquid pharmaceutical composition. In some embodiments, the oral pharmaceutical composition is a suspension. In some embodiments, the oral pharmaceutical composition is a solution. In some embodiments, the oral pharmaceutical composition is a syrup.

Pharmaceutical Composition: Metronidazole

The oral pharmaceutical compositions of the present disclosure comprise metronidazole. Metronidazole is a synthetic nitroimidazole antimicrobial compound, described by the chemical name 2-(2-methyl-5-nitro-1H-imidazol-1-yl) ethanol and marketed under the brand name Flagyl™. Metronidazole has the following chemical structure:

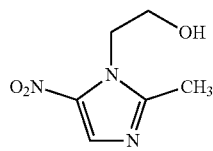

Metronidazole is commercially available. As used herein, the term "metronidazole" refers to a metronidazole base. Various pharmaceutically acceptable salts of metronidazole are also contemplated for use in the disclosed compositions and methods. The term "pharmaceutically acceptable salt" refers to an addition salt that exists in conjunction with the acidic or basic portion of metronidazole. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when metronidazole or any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature may be formed when metronidazole or any of its intermediates containing an acidic functionality are reacted with a pharmaceutically acceptable base. Pharmaceutically acceptable bases commonly employed to form base addition salts include organic and inorganic bases. As used herein, pharmaceutically acceptable salt explicitly excludes metronidazole benzoate. Some particularly preferred pharmaceutically acceptable salts include metronidazole hydrochloride and metronidazole phosphate. In addition to pharmaceutically acceptable salts, other salts may be included in some embodiments of the present invention. For example, they may serve as intermediates in the purification of compounds or in the preparation of other pharmaceutically-acceptable salts, or may be useful for identification, characterization and/or purification.

In some embodiments, metronidazole is present at a concentration of from about 50 milligrams (mg) to about 500 mg per 5 milliliters (ml) of the oral pharmaceutical composition. In some embodiments, metronidazole is present at a concentration of from about 100 mg to about 500 mg per 5 ml of the oral pharmaceutical composition. In some embodiments, metronidazole is present at a concentration of from about 200 mg to about 500 mg per 5 ml of the oral pharmaceutical composition. In some embodiments, metronidazole is present at a concentration of from about 250 mg to about 500 mg per 5 ml of the oral pharmaceutical composition. In some embodiments, metronidazole is present at a concentration of from about 250 mg to about 400 mg per 5 ml of the oral pharmaceutical composition. In some embodiments, metronidazole is present at a concentration of about 250 mg to about 400 mg per 5 ml of the oral pharmaceutical composition. In some embodiments, metronidazole is present at a concentration of about 250 mg/5 ml of the oral pharmaceutical composition.

In some embodiments, the metronidazole is in a pseudo-syrup solution (i.e., in a syrup-like phase) prior to being combined with the magnesium aluminum silicate to form a liquid oral suspension. The pseudo-syrup solution can be, for example: 1) water and 2) sucrose, an artificial sweetener or glycerol or a combination of sucrose, an artificial sweetener and/or glycerol.

Pharmaceutical Composition: Magnesium Aluminum Silicate

In some embodiments, the formulations disclosed herein comprise a suspending agent. Typically, suspending agents are provided in pharmaceutical formulations to help active pharmaceutical ingredients stay suspended in the formulation and to prevent caking at the bottom of the container. For example, one property of a well-formulated suspension is that it can be easily re-suspended by the use of moderate agitation or shaking.

In contrast, the inventors have discovered that use of a particular suspending agent contributes to taste masking and/or masking an aftertaste of metronidazole when used in the formulations provided herein.

In some preferred embodiments, the suspending agent comprises magnesium aluminum silicate (MgAlSi). MgAlSi is a blend of colloidal montmorillonite and saponite. In some embodiments the MgAlSi is United States Pharmacopeia-National Formulary (USP-NF) grade. The magnesium aluminum silicate, may be a natural product such as products sold under the trade name Veegum™ (Vanderbilt Minerals), which is a blend of refined, smectite, colloidal montmorillonite and saponite clays. Briefly, this clay material forms silicate layer structures that have weakly positive edges and negatively charged surfaces. Hydration of the clay delaminates the layer structure into individual platelets, and these individual particles then form a "house of cards"-type lattice where the negatively charged edges are attracted to the positively charged faces. This three-dimensional colloidal structure promotes viscosity of MgAlSi suspensions, and provides adsorptive surfaces. The clay material may stabilize emulsions and prevent separation over time (Ciullo 1980, Aguzzi 2007, Rowe 2009). Without being bound by any theories, the metronidazole in the formulations disclosed herein may be trapped in between the platelets to form a liquid suspension, and the suspension may contribute to the taste-masking of metronidazole.

In some embodiments, the magnesium aluminum silicate is a synthetic product, such as magnesium aluminometasilicate, for example, Neusilin™ or Neusilin™ UF12.

It is contemplated herein that the suspending agent contributes to taste masking of metronidazole. The inventors hypothesize that two characteristics of MgAlSi may contribute to taste-masking and/or reduced aftertaste: i) its adsorbant properties; and ii) its ability to increase viscosity.

Adsorption occurs when molecules of a gas, liquid, or dissolved solid adhere to the surface of the adsorbant agent. When adsorbed onto MgAlSi, bitter compounds are less soluble in saliva and therefore pass through the mouth with less dissolution of the compound (Sohi 2004, Sharma 2010). However, adsorption may adversely affect the bioavailability of certain drugs if they are tightly bound to the adsorbant, or are slowly desorbed. For example, MgAlSi has been found to significantly decrease the bioavailability ($C_{max}$ and AUC) of tetracycline solutions in the presence of bismuth subsalicylate (Healy 1997). Adsorbants such as MgAlSi may also adsorb preservatives, flavorings, and surfactants from liquid suspensions (Duro 1999, Elder 2012). Accordingly, it difficult to predict how MgAlSi will affect a specific API provided in a formulation.

Increasing the viscosity of an oral liquid formulation may limit the diffusion of bitter tasting substances from the saliva to the taste buds. Alternative thickening agents commonly used in pharmaceutical formulations also have taste-masking properties. For example, the bitter taste of acetaminophen in suspension can be reduced by the addition of xanthan gum (0.1-0.2%) and microcrystalline cellulose (0.6-1%) (Sharma 2010). The bitter taste of the antidepressant mirtazapine is reduced due to the presence of the thickening agent maltitol (Sharma 2010). In the same context as reducing the diffusion to the taste buds, pharmaceutical grade clays, as well as the common thickeners guar gum and xantham gum, have been considered as drug-delivery modifiers due to their ability to slow diffusion out of the formulation (Aguzzi 2007, Ramasamy 2011). Accordingly, there are many options to increase viscosity of a pharmaceutical formulation and some may effect rate of API diffusion from the formulation.

In some embodiments, the concentration of magnesium aluminum silicate is between 1% and 10% (w/v) of the oral pharmaceutical composition. In some embodiments, the concentration of magnesium aluminum silicate is between 1% and 5% (w/v) of the oral pharmaceutical composition. In some embodiments, the concentration of magnesium aluminum silicate is between 5% and 10% (w/v) of the oral pharmaceutical composition. In some embodiments, the concentration of magnesium aluminum silicate is no more than 6.4% (w/v) of the oral pharmaceutical composition. In some embodiments, the concentration of magnesium aluminum silicate is no more than 2.0% (w/v) of the oral pharmaceutical composition. In some embodiments, the concentration of magnesium aluminum silicate is about 1.2% (w/v) of the oral pharmaceutical composition.

In some embodiments, the magnesium aluminum silicate is VEEGUM® brand. In one embodiment, the magnesium aluminum silicate is VEEGUM HV (magnesium aluminum silicate NF Type IC, pharmaceutical grade). In some embodiments, the concentration of VEEGUM HV is no more than 1.2% (w/v) of the oral pharmaceutical composition. In some embodiments, herein the concentration of VEEGUM HV™ is about 1.2% (w/v) of the oral pharmaceutical composition.

In one embodiment, the magnesium aluminum silicate is VEEGUM PRO. In another embodiment, the magnesium aluminum silicate is VEEGUM PURE (magnesium aluminum silicate NF Type IA, produced to pharmaceutical grade specifications). In another embodiment, the magnesium aluminum silicate is VEEGUM R (magnesium aluminum silicate NF Type IA, pharmaceutical grade).

The MgAlSi may be type IA, IB, IC or IIA. The viscosity and ratio of aluminum content to magnesium content in the MgAlSi may vary by type of MgAlSi as set out in Table A below:

TABLE A

Viscosity and Ratio of Aluminum Content to Magnesium Content in MgAlSi by Type of MgAlSi

| Type | Viscosity (mPa · s) | | Al Content/ Mg Content | |
|---|---|---|---|---|
| | Min. | Max. | Min. | Max. |
| IA | 225 | 600 | 0.5 | 1.2 |
| IB | 150 | 450 | 0.5 | 1.2 |
| IC | 800 | 2200 | 0.5 | 1.2 |
| IIA | 100 | 300 | 1.4 | 2.8 |

Pharmaceutical Composition: At Least One Flavoring Agent
Flavoring Agents

In some embodiments, the taste masking composition provided herein comprises one or more flavoring agents. In some preferred embodiments the one or more flavoring agents comprises mint, particularly preferably, peppermint. In some embodiments, the one or more flavoring agents is a natural flavor, artificial flavor, or mixture thereof.

Flavoring Agents—Mint

In some embodiments, the one or more flavoring agents comprises mint. By "mint" we mean mint flavor, or one or more components of and/or extracts from mint plant materials, which comprise a mint flavor, or a synthetic compound or composition having a mint flavor. For example, in some embodiments, mint flavor may refer to the essential oil, oleoresin, essence or extractive, protein hydrolysate, distillate, or any product of roasting, heating or enzymolysis, which contains the flavoring constituents derived from mint. Mint also refers to the genus of plants, Mentha, which includes at least the species: *aquatica* (also referred to as water mint, marsh mint), *arvensis* (also referred to as corn mint, wild mint, Japanese peppermint, field mint, banana mint), *asiatica* (also referred to as Asian mint), *australis* (also referred to as Australian mint), *canadensis* (also referred to as American wild mint), *cervina* (also referred to as Hart's pennyroyal), *citrata* (also referred to as bergamot mint, orange mint), *crispata* (also referred to as wrinkled-leaf mint), *dahurica* (also referred to as Dahurian thyme), *diemenica* (also referred to as slender mint), *laxiflora* (also referred to as forest mint), *longifolia* (syn. *sylvestris*) (also referred to as horse mint), *piperita* (also referred to as peppermint), *pulegium* (also referred to as pennyroyal), *requienii* (also referred to as Corsican mint), *sachalinensis* (also referred to as garden mint), *satureioides* (also referred to as native pennyroyal), *spicata* (syn. *viridis, cordifolia*) (also referred to as spearmint, curly mint (a cultivar of spearmint)), *suaveolens* (also referred to as apple mint, pineapple mint (a variegated cultivar of apple mint)), and *vagans* (also referred to as gray mint). Mint hybrids are also contemplated.

In some embodiments the mint is a natural flavor. In some embodiments the mint is an artificial flavor.

In some embodiments, the one or more flavoring agents comprises peppermint. In some embodiments the peppermint is peppermint flavor. In some embodiments, the peppermint is peppermint oil. In some embodiments, the concentration of peppermint is between 0.01% and 2.0% (v/v) of the oral pharmaceutical composition. In some embodiments, the concentration of peppermint is between 0.1% and 1.0% (v/v) of the oral pharmaceutical composition. In some embodiments, the concentration of peppermint is less than or equal to 0.2% (v/v) of the oral pharmaceutical composition. In some embodiments, the concentration of peppermint is about 0.2% (v/v) of the oral pharmaceutical composition.

In some embodiments the peppermint is a natural flavor. In some embodiments the peppermint is an artificial flavor.

Flavoring Agents—Natural Fruit Flavors

In some embodiments, the flavoring agent is a natural flavor that is a natural fruit flavor.

In some embodiments, the natural fruit flavor is lemon. In some embodiments, the concentration of lemon is between 7% and 11% (v/v) of the oral pharmaceutical composition. In some embodiments, the concentration of lemon is no more than 9% (v/v) of the oral pharmaceutical composition.

In some embodiments, the natural fruit flavor is orange. In some embodiments, the concentration of orange is between 1 and 2%. In some embodiments, the concentration of orange is no more than 1.5% (v/v) of the oral pharmaceutical composition.

In some embodiments, the natural fruit flavor is lime. In some embodiments, the concentration of lime is between 4% and 6% (v/v) of the oral pharmaceutical composition. In some embodiments, the concentration of lime is no more than 5% (v/v) of the oral pharmaceutical composition.

In some embodiments, the natural fruit flavor is apricot. In some embodiments, the concentration of apricot is between 0.1% and 1% (v/v) of the oral pharmaceutical composition. In some embodiments, the concentration of apricot is no more than 0.5% (v/v) of the oral pharmaceutical composition.

In some embodiments, the natural fruit flavor is grapefruit. In some embodiments, the concentration of grapefruit is 1% to 2% (v/v) of the oral pharmaceutical composition. In some embodiments, the concentration of grapefruit is no more than 1.5% (v/v) of the oral pharmaceutical composition.

In some embodiments, the natural fruit flavor is banana. In some embodiments, the concentration of banana is between 0.4% and 0.6% (v/v) of the oral pharmaceutical composition. In some embodiments, the concentration of banana is no more than 0.5% (v/v) of the oral pharmaceutical composition.

In some embodiments, the natural fruit flavor is cherry. In some embodiments, the concentration of cherry between 4% and 6%. In some embodiments, the concentration of cherry is no more than 5% (v/v) of the oral pharmaceutical composition.

In some embodiments, the natural fruit flavor is apple. In some embodiments, the concentration of apple is between 0.8% and 1.2% (v/v) of the oral pharmaceutical composition. In some embodiments, the concentration of apple is no more than 1% (v/v) of the oral pharmaceutical composition.

In some embodiments, the natural fruit flavor is pineapple. In some embodiments, the concentration of pineapple is between 0.8% and 1.2% (v/v) of the oral pharmaceutical composition. In some embodiments, the concentration of pineapple is no more than 1% (v/v) of the oral pharmaceutical composition.

In some embodiments, the natural fruit flavor is grape. In some embodiments, the concentration of grape is between 0.8% and 1.2% (v/v) of the oral pharmaceutical composition. In some embodiments, the concentration of grape is no more than 1% (v/v) of the oral pharmaceutical composition.

In some embodiments, the natural fruit flavor is strawberry. In some embodiments, the concentration of strawberry is between 3.2% and 4.8% (v/v) of the oral pharmaceutical composition. In some embodiments, the concentration of strawberry is no more than 4% (v/v) of the oral pharmaceutical composition. In some embodiments, the concentration of strawberry is no more than 1.0% (w/v), no more than 0.4% (w/v) or no more than 0.2% (v/v) of the oral pharmaceutical composition. In some embodiments, the concentration of strawberry is about 0.1% (w/v) of the oral pharmaceutical composition. In some embodiments, the concentration of strawberry is about 0.4% (w/v) of the oral pharmaceutical composition.

In some embodiments, the natural fruit flavor is raspberry. In some embodiments, the concentration of raspberry is between 5.6% and 18.4% (v/v) of the oral pharmaceutical composition. In some embodiments, the concentration of raspberry is no more than 7% (v/v) of the oral pharmaceutical composition. In some embodiments, the concentration of raspberry is between 0.2% and 0.8% (v/v) of the oral pharmaceutical composition. In some embodiments, the concentration of raspberry is no more than 0.5% (v/v) of the oral pharmaceutical composition. In some embodiments, the concentration of raspberry is 0.4% (v/v) of the oral pharmaceutical composition.

In some embodiments, the natural fruit flavor is tutti frutti. In some embodiments, the concentration of tutti frutti is between 0.4% and 0.6% (v/v) of the oral pharmaceutical composition. In some embodiments, the concentration of tutti frutti is no more than 0.5% (v/v) of the oral pharmaceutical composition.

In some embodiments, the natural fruit flavor is fruit punch. In some embodiments, the concentration of fruit punch is between 14% and 22% (v/v) of the oral pharmaceutical composition. In some embodiments, the concentration of fruit punch is no more than 18% (v/v) of the oral pharmaceutical composition.

Flavoring Agents—Artificial Fruit Flavors

In some embodiments, the flavoring agent is an artificial flavor that is an artificial fruit flavor.

In some embodiments, the artificial fruit flavor is lemon. In some embodiments, the concentration of lemon is between 7% and 11% (v/v) of the oral pharmaceutical composition. In some embodiments, the concentration of lemon is no more than 9% (v/v) of the oral pharmaceutical composition.

In some embodiments, the artificial fruit flavor is orange. In some embodiments, the concentration of orange is between 1 and 2%. In some embodiments, the concentration of orange is no more than 1.5% (v/v) of the oral pharmaceutical composition.

In some embodiments, the artificial fruit flavor is lime. In some embodiments, the concentration of lime is between 4% and 6% (v/v) of the oral pharmaceutical composition. In some embodiments, the concentration of lime is no more than 5% (v/v) of the oral pharmaceutical composition.

In some embodiments, the artificial fruit flavor is apricot. In some embodiments, the concentration of apricot is between 0.1% and 1% (v/v) of the oral pharmaceutical composition. In some embodiments, the concentration of apricot is no more than 0.5% (v/v) of the oral pharmaceutical composition.

In some embodiments, the artificial fruit flavor is grapefruit. In some embodiments, the concentration of grapefruit is 1% to 2% (v/v) of the oral pharmaceutical composition. In some embodiments, the concentration of grapefruit is no more than 1.5% (v/v) of the oral pharmaceutical composition.

In some embodiments, the artificial fruit flavor is banana. In some embodiments, the concentration of banana is between 0.4% and 0.6% (v/v) of the oral pharmaceutical composition. In some embodiments, the concentration of banana is no more than 0.5% (v/v) of the oral pharmaceutical composition.

In some embodiments, the artificial fruit flavor is cherry. In some embodiments, the concentration of cherry between 4% and 6%. In some embodiments, the concentration of cherry is no more than 5% (v/v) of the oral pharmaceutical composition.

In some embodiments, the artificial fruit flavor is apple. In some embodiments, the concentration of apple is between 0.8% and 1.2% (v/v) of the oral pharmaceutical composition. In some embodiments, the concentration of apple is no more than 1% (v/v) of the oral pharmaceutical composition.

In some embodiments, the artificial fruit flavor is pineapple. In some embodiments, the concentration of pineapple is between 0.8% and 1.2% (v/v) of the oral pharmaceutical composition. In some embodiments, the concentration of pineapple is no more than 1% (v/v) of the oral pharmaceutical composition.

In some embodiments, the artificial fruit flavor is grape. In some embodiments, the concentration of grape is between 0.8% and 1.2% (v/v) of the oral pharmaceutical composition. In some embodiments, the concentration of grape is no more than 1% (v/v) of the oral pharmaceutical composition.

In some embodiments, the artificial fruit flavor is strawberry. In some embodiments, the concentration of strawberry is between 3.2% and 4.8% (v/v) of the oral pharmaceutical composition. In some embodiments, the concentration of strawberry is no more than 4% (v/v) of the oral pharmaceutical composition. In some embodiments, the concentration of strawberry is no more than 1.0% (w/v), no more than 0.4% (w/v) or no more than 0.2% (v/v) of the oral pharmaceutical composition. In some embodiments, the concentration of strawberry is about 0.1% (v/v) of the oral pharmaceutical composition. In some embodiments, the concentration of strawberry is about 0.4% (w/v) of the oral pharmaceutical composition.

In some embodiments, the artificial fruit flavor is raspberry. In some embodiments, the concentration of raspberry is between 5.6% and 18.4% (v/v) of the oral pharmaceutical composition. In some embodiments, the concentration of raspberry is no more than 7% (v/v) of the oral pharmaceutical composition. In some embodiments, the concentration of raspberry is between 0.2% and 0.8% (v/v) of the oral pharmaceutical composition. In some embodiments, the concentration of raspberry is no more than 0.5% (v/v) of the oral pharmaceutical composition. In some embodiments, the concentration of raspberry is 0.4% (v/v) of the oral pharmaceutical composition.

In some embodiments, the artificial fruit flavor is tutti frutti. In some embodiments, the concentration of tutti frutti is between 0.4% and 0.6% (v/v) of the oral pharmaceutical composition. In some embodiments, the concentration of tutti frutti is no more than 0.5% (v/v) of the oral pharmaceutical composition.

In some embodiments, the artificial fruit flavor is fruit punch. In some embodiments, the concentration of fruit punch is between 14% and 22% (v/v) of the oral pharmaceutical composition. In some embodiments, the concentration of fruit punch is no more than 18% (v/v) of the oral pharmaceutical composition.

Flavoring Agents—Some Preferred Embodiments

In some preferred embodiments, the one or more flavoring agents comprise strawberry and raspberry. In some preferred embodiments, the concentration of strawberry is 0.1% (v/v) of the oral pharmaceutical composition and the concentration of raspberry is 0.4% (v/v) of the oral pharmaceutical composition.

In some preferred embodiments, the one or more flavoring agents comprise strawberry and peppermint. In some preferred embodiments, the concentration of strawberry is 0.1% (v/v) of the oral pharmaceutical composition and the concentration of peppermint is 0.2% (v/v) of the oral pharmaceutical composition. In some preferred embodiments, the concentration of strawberry is about 0.4% (w/v) of the oral pharmaceutical composition and the concentration of peppermint is about 0.2% (w/v) of the oral pharmaceutical composition.

In some preferred embodiments, the one or more flavoring agents comprise raspberry and peppermint. In some preferred embodiments, the concentration of raspberry is 0.4% (v/v) of the oral pharmaceutical composition and the concentration of peppermint is 0.2% (v/v) of the oral pharmaceutical composition. In some preferred embodiments, the concentration of raspberry is 0.8% (v/v) of the oral pharmaceutical composition and the concentration of peppermint is 0.1% (v/v) of the oral pharmaceutical composition.

In some preferred embodiments, the one or more flavoring agents comprise strawberry, raspberry, and peppermint. In some preferred embodiments, the concentration of strawberry is 0.1% (v/v) of the oral pharmaceutical composition, the concentration of raspberry is 0.4% (v/v) of the oral pharmaceutical composition, and the concentration of peppermint is 0.1% (v/v) of the oral pharmaceutical composition. In other preferred embodiments, the concentration of strawberry is 0.1% (v/v) of the oral pharmaceutical composition, the concentration of raspberry is 0.4% (v/v) of the oral pharmaceutical composition, and the concentration of peppermint is 0.2% (v/v) of the oral pharmaceutical composition.

In some preferred embodiments, the one or more flavoring agents comprise strawberry, raspberry and peppermint. As demonstrated in the Examples of the present disclosure, an unexpected improvement in one or more of the taste properties of the compositions described herein was obtained incorporating into the metronidazole composition one or more of these flavoring agents.

Pharmaceutical Composition: Sweeteners

In some embodiments of the present disclosure, the oral pharmaceutical compositions of the present invention comprise one or more sweeteners. In some embodiments, the sweetener is a natural sweetener. A "natural sweetener" is well known to persons of ordinary skill in the art. In some embodiments, the natural sweetener is sucrose, glucose, fructose, stevia, or mixtures thereof.

Sweeteners: Natural Sweeteners

In some embodiments, the natural sweetener is sucrose. In some embodiments, the concentration of sucrose is between 25% and 85% (w/v) of the oral pharmaceutical composition. In some embodiments, the concentration of sucrose is no more than 60% (w/v) of the oral pharmaceutical composition. In some embodiments, the concentration of sucrose is no more than 72% (w/v) of the oral pharmaceutical composition. In some embodiments, the concentration of sucrose is no more than 82% (w/v) of the oral pharmaceutical composition. In some embodiments, the concentration of sucrose is no more than 50% (w/v) of the oral pharmaceutical composition. In some embodiments, the concentration of sucrose is about 50% (w/v) of the oral pharmaceutical composition. In some embodiments, the sucrose is sucrose NF.

In some embodiments, the natural sweetener is glucose. In some embodiments, the concentration of glucose is between 30% and 70% (w/v) of the oral pharmaceutical composition. In some embodiments, the concentration of glucose is no more than 40% (w/v) of the oral pharmaceutical composition. In some embodiments, the concentration of glucose is no more than 50% (w/v) of the oral pharmaceutical composition. In some embodiments, the concentration of glucose is no more than 62% (w/v) of the oral pharmaceutical composition.

In some embodiments, the natural sweetener is fructose. In some embodiments, the concentration of fructose is between 1% and 40% (w/v) of the oral pharmaceutical composition. In some embodiments, the concentration of fructose is no more than 2% (w/v) of the oral pharmaceutical composition. In some embodiments, the concentration of fructose is no more than 35% (w/v) of the oral pharmaceutical composition.

In some embodiments, the natural sweetener is stevia.

Sweeteners: Artificial Sweeteners

In some embodiments, the sweetener is an artificial sweetener. An "artificial sweetener" is well known to persons of ordinary skill in the art. In some embodiments, the artificial sweetener is sucralose, sorbitol, saccharin, aspartame, acesulfame potassium, neotame, advantame, or mixtures thereof.

In some embodiments, the artificial sweetener is sucralose. In some embodiments, the concentration of sucralose is between 0.1% and 10% (w/v) of the oral pharmaceutical composition. In some embodiments, the concentration of sucralose is no more than 5% (w/v) of the oral pharmaceutical composition. In some embodiments, the concentration of sucralose is no more than 1.1% (w/v) of the oral pharmaceutical composition. In some embodiments, the concentration of sucralose is no more than 0.25% (w/v) of the oral pharmaceutical composition. In some embodiments, the concentration of sucralose is 0.25% (w/v) of the oral pharmaceutical composition.

In some embodiments, the artificial sweetener is sorbitol. In some embodiments, the concentration of sorbitol is between 50% and 99% (w/v) of the oral pharmaceutical composition. In some embodiments, the concentration of sorbitol is no more than 90% (w/v) of the oral pharmaceutical composition.

In some embodiments, the artificial sweetener is saccharin, for example "free base" saccharin. In some embodiments, the concentration of free base saccharin is between 3.5 mg/5 mL and 10 mg/1 mL of the oral pharmaceutical composition.

In some embodiments, the saccharin is saccharine sodium. In some embodiments, the concentration of saccharine sodium is between 1% and 10% (w/v) of the oral pharmaceutical composition. In some embodiments, the concentration of saccharine sodium is no more than 1.4% (w/v) of the oral pharmaceutical composition. In some embodiments, the concentration of saccharine sodium is no more than 3% (w/v) of the oral pharmaceutical composition. In some embodiments, the concentration of saccharine sodium is no more than 5% (w/v) of the oral pharmaceutical composition.

In some embodiments, the saccharin is saccharine calcium. In some embodiments, the concentration of saccharine calcium is no more than 0.01% (w/v) of the oral pharmaceutical composition. In some embodiments, the concentration of saccharine calcium is no more than 17.5 mg/5 mL of the oral pharmaceutical composition.

In some embodiments, the artificial sweetener is aspartame. In some embodiments, the concentration of aspartame is between 20% and 60% (w/v) of the oral pharmaceutical composition. In some embodiments, the concentration of aspartame is no more than 40% (w/v) of the oral pharmaceutical composition.

In some embodiments, the artificial sweetener is acesulfame potassium. In some embodiments, the concentration of acesulfame potassium is between 0.1% and 1% (w/v) of the oral pharmaceutical composition. In some embodiments, the concentration of acesulfame potassium is no more than 0.15% (w/v) of the oral pharmaceutical composition. In some embodiments, the concentration of acesulfame potassium is no more than 0.5% (w/v) of the oral pharmaceutical composition.

In some embodiments, the artificial sweetener is neotame.

In some embodiments, the artificial sweetener is advantame.

Pharmaceutical Composition: Excipients

In some embodiments, the oral pharmaceutical compositions disclosed herein further comprise one or more excipients. In some embodiments, the one or more excipients comprises one or more of a viscosity agent, preservative, buffer, and solvent.

Excipients: Viscosity Agent

As indicated above, increasing the viscosity of an oral liquid formulation, by adding a viscosity agent, may limit the diffusion of bitter tasting substances from the saliva to the taste buds.

In some embodiments, the formulation provided herein comprises one or more viscosity agents. In some embodiments, the suspension agent also acts as a viscosity agent (e.g., MgSiAl). In some embodiments, the viscosity agent comprises one or more of a cellulose derivative, an anionic, or combinations thereof. Such cellulose derivative may also act as texture modifiers.

In some embodiments, the viscosity agent is a cellulose derivative. In some embodiments, the cellulose derivative is one or more of microcrystalline cellulose, methylcellulose, hydroxyethylcellulose, hydroxypropylcellulose, or a combination thereof.

In some embodiments, the cellulose derivative is microcrystalline cellulose. In some embodiments, the concentration of microcrystalline cellulose is between 0.1% and 5% (w/v) of the oral pharmaceutical composition. In some embodiments, the concentration of microcrystalline cellulose is no more than 0.60% (w/v) of the oral pharmaceutical composition. In some embodiments, the concentration of microcrystalline cellulose is about 0.60% (w/v) of the oral pharmaceutical composition. In some embodiments, the concentration of microcrystalline cellulose is no more than 1.4% (w/v) of the oral pharmaceutical composition.

In some embodiments, the cellulose derivative is methylcellulose. In some embodiments, the concentration of methylcellulose is no more than 0.025% (w/v) of the oral pharmaceutical composition.

In some embodiments, the cellulose derivative is hydroxyethylcellulose. In some embodiments, the concentration of hydroxyethylcellulose is between 0.1% and 10% (w/v) of the oral pharmaceutical composition. In some embodiments, the concentration of hydroxyethylcellulose is no more than 0.1% (w/v) of the oral pharmaceutical composition. In some embodiments, the concentration of hydroxyethylcellulose is no more than 0.7% (w/v) of the oral pharmaceutical composition. In some embodiments, the concentration of hydroxyethylcellulose is no more than 10% (w/v) of the oral pharmaceutical composition.

In some embodiments, the cellulose derivative is hydroxypropylcellulose. In some embodiments, the concentration of hydroxypropylcellulose is between 0.1% and 10% (w/v) of the oral pharmaceutical composition. In some embodiments, the concentration of hydroxypropylcellulose is no more than 0.5% (w/v) of the oral pharmaceutical composition. In some embodiments, the concentration of hydroxypropylcellulose is no more than 2% (w/v) of the oral pharmaceutical composition. In some embodiments, the concentration of hydroxypropylcellulose is no more than 5% (w/v) of the oral pharmaceutical composition.

In some embodiments, the viscosity agent is an anionic. In some embodiments, the anionic is sodium alginate. In some embodiments, the concentration of sodium alginate is between 0.1% and 1% (w/v) of the oral pharmaceutical composition. In some embodiments, the concentration of sodium alginate is no more than 0.1% (w/v) of the oral pharmaceutical composition. In some embodiments, the concentration of sodium alginate is no more than 0.3% (w/v) of the oral pharmaceutical composition.

Sweeteners, such as sugars, when used in high concentrations also may be viscosity agents. In addition, MgAlSi can also affect the viscosity of the formulations disclosed herein.

Excipients: Preservative

A preservative may be provided to prevent contamination (e.g., growth of microbes) of the composition.

In some embodiments, the preservative comprises one or more of amino aryl acid ester, aryl acid, alkyl acid, amino aryl acid ester/organic acid, and combinations thereof. In some embodiments, propylene glycol may be added as an adjunct to preservation. In some embodiments, sucrose may contribute to preservation, although its primary function is as a sweetener.

In some embodiments, the preservative comprises an amino aryl acid ester. In some embodiments, the amino aryl acid ester is methyl paraben, ethyl paraben, propyl paraben, or combinations thereof. In some embodiments, one or more parabens are preferred as a preservative because the exhibit optimum activity at a pH of about 4-8.

In some embodiments, the amino aryl acid ester is methyl paraben. In some embodiments, the concentration of methyl paraben is between 0.01% and 20% (w/v) of the oral pharmaceutical composition. In some embodiments, the concentration of methyl paraben is no more than 0.2% (w/v) of the oral pharmaceutical composition. In some embodiments, the concentration of methyl paraben is no more than 5% (w/v) of the oral pharmaceutical composition. In some embodiments, the concentration of methyl paraben is no more than 13% (w/v) of the oral pharmaceutical composition. In some embodiments, the concentration of methyl paraben is no more than 0.15% (w/v) of the oral pharmaceutical composition. In some embodiments, the concentration of methyl paraben is about 0.15% (w/v) of the oral pharmaceutical composition.

In some embodiments, the amino aryl acid ester is ethyl paraben.

In some embodiments, the amino aryl acid ester is propyl paraben. In some embodiments, the concentration of propyl paraben is between 0.01% and 40% (w/v) of the oral pharmaceutical composition. In some embodiments, the concentration of propyl paraben is between 0.048% and 0.072% (w/v) of the oral pharmaceutical composition. In some embodiments, the concentration of propyl paraben is no more than 0.06% (w/v) of the oral pharmaceutical composition. In some embodiments, the concentration of propyl paraben is no more than 10% (w/v) of the oral pharmaceutical composition. In some embodiments, the concentration of propyl paraben is no more than 36% (w/v) of the oral pharmaceutical composition. In some embodiments, the concentration of propyl paraben is no more than 0.2% (w/v) of the oral pharmaceutical composition. In some embodiments, the concentration of propyl paraben is about 0.2% (w/v) of the oral pharmaceutical composition.

In some embodiments, the preservative is a combination of methyl paraben and propyl paraben. It is contemplated that this combination may provide a synergistic effect, meaning that lower quantities of each paraben may be used to preserve the composition, relative to the quantities that would be required for each paraben to preserve the composition on its own.

In some embodiments, the preservative comprises an aryl acid. In some embodiments, the aryl acid is sodium benzoate, benzoic acid, or a combination thereof.

In some embodiments, the aryl acid is sodium benzoate. In some embodiments, the concentration of sodium benzoate is between 0.01% and 10% (w/v) of the oral pharmaceutical composition. In some embodiments, the concentration of sodium benzoate is no more than 0.2% (w/v) of the oral pharmaceutical composition. In some embodiments, the concentration of sodium benzoate is no more than 1% (w/v) of the oral pharmaceutical composition. In some embodiments, the concentration of sodium benzoate is no more than 5% (w/v) of the oral pharmaceutical composition.

In some embodiments, the aryl acid is benzoic acid. In some embodiments, the concentration of benzoic acid is between 0.01% and 10% (w/v) of the oral pharmaceutical composition. In some embodiments, the concentration of benzoic acid is no more than 0.1% (w/v) of the oral pharmaceutical composition. In some embodiments, the concentration of benzoic acid is no more than 0.5% (w/v) of the oral pharmaceutical composition. In some embodiments, the concentration of benzoic acid is no more than 0.7% (w/v) of the oral pharmaceutical composition.

In some embodiments, the preservative comprises an alkyl acid. In some embodiments, the alkyl acid is sorbic acid, potassium sorbate, propionic acid, or a combination thereof.

In some embodiments, the alkyl acid is sorbic acid. In some embodiments, the concentration of sorbic acid is between 0.01% and 1% (w/v) of the oral pharmaceutical composition. In some embodiments, the concentration of sorbic acid is no more than 0.01% (w/v) of the oral pharmaceutical composition. In some embodiments, the concentration of sorbic acid is no more than 0.1% (w/v) of the oral pharmaceutical composition. In some embodiments, the concentration of sorbic acid is no more than 0.5% (w/v) of the oral pharmaceutical composition.

In some embodiments, the alkyl acid is potassium sorbate. In some embodiments, the concentration of potassium sorbate is between 0.01% and 1% (w/v) of the oral pharmaceutical composition. In some embodiments, the concentration of potassium sorbate is no more than 0.65% (w/v) of the oral pharmaceutical composition.

In some embodiments, the alkyl acid is propionic acid.

In some embodiments, the preservative comprises an amino aryl acid ester/organic acid. In some embodiments, the amino aryl acid ester/organic acid is a methyl paraben/sodium benzoate combination.

Excipients: Buffer

In some embodiments, a buffer may be provided in the composition to maintain a desired pH. In some preferred embodiments, the buffer does not affect taste masking.

In some embodiments, the buffer comprises one or more of an acetate, a citrate, sodium phosphate monobasic, sodium phosphate dibasic, or a combination thereof.

In some embodiments, the buffer comprises an acetate. In one embodiment, the acetate is acetic acid, sodium acetate, or a combination thereof.

In some embodiments, the acetate is acetic acid. In some embodiments, the concentration of acetic acid is about 0.08% to 1.2% (w/v) of the oral pharmaceutical composition. In some embodiments, the concentration of acetic acid is no more than 0.1% (w/v) of the oral pharmaceutical composition. In some embodiments, the acetate is sodium acetate. In some embodiments, the concentration of sodium acetate is about 0.08% to 1.2% (w/v) of the oral pharmaceutical composition. In some embodiments, the concentration of sodium acetate is no more than 0.1% (w/v) of the oral pharmaceutical composition.

In some embodiments, the buffer comprises a citrate. In some embodiments, the citrate is citric acid, sodium citrate, sodium hydroxide, hydrochloric acid, or a combination thereof.

In some embodiments, the citrate is citric acid. In some embodiments, the concentration of citric acid is between 0.1% and 75% (w/v) of the oral pharmaceutical composition. In some embodiments, the concentration of citric acid is no more than 0.18% (w/v) of the oral pharmaceutical composition. In some embodiments, the concentration of citric acid is no more than 0.8% (w/v) of the oral pharmaceutical composition. In some embodiments, the concentration of citric acid is no more than 72% (w/v) of the oral pharmaceutical composition.

In some embodiments, the citrate is sodium citrate. In some embodiments, the concentration of sodium citrate is between 0.01% and 40% (w/v) of the oral pharmaceutical composition. In some embodiments, the concentration of sodium citrate is no more than 0.1% (w/v) of the oral pharmaceutical composition. In some embodiments, the concentration of sodium citrate is no more than 1.1% (w/v) of the oral pharmaceutical composition. In some embodiments, the concentration of sodium citrate is no more than 32% (w/v) of the oral pharmaceutical composition.

In some embodiments, the citrate is sodium hydroxide. In some embodiments, the concentration of sodium hydroxide between about 32% and about 48% (w/v) of the oral pharmaceutical composition. In some embodiments, the concentration of sodium hydroxide is no more than 40% (w/v) of the oral pharmaceutical composition. In some embodiments, the citrate is hydrochloric acid. In some embodiments, the concentration of hydrochloric acid between about 8% and about 11% (w/v) of the oral pharmaceutical composition. In some embodiments, the concentration of hydrochloric acid is no more than 10% (w/v) of the oral pharmaceutical composition.

In some embodiments, the buffer comprises sodium phosphate monobasic. In some embodiments, the concentration of sodium phosphate monobasic is between 0.01% and 2% (w/v) of the oral pharmaceutical composition. In some embodiments, the concentration of sodium phosphate monobasic is no more than 0.2% (w/v) of the oral pharmaceutical composition. In some embodiments, the concentration of sodium phosphate monobasic is about 0.2% (w/v) of the oral pharmaceutical composition. In some embodiments, the concentration of sodium phosphate monobasic is no more than 0.5% (w/v) of the oral pharmaceutical composition. In some embodiments, the concentration of sodium phosphate monobasic is no more than 1.2% (w/v) of the oral pharmaceutical composition.

In some embodiments, the buffer comprises sodium phosphate dibasic. In some embodiments, the concentration of sodium phosphate dibasic is between 0.01% and 5% (w/v) of the oral pharmaceutical composition. In some embodiments, the concentration of sodium phosphate dibasic is no more than 0.2% (w/v) of the oral pharmaceutical composition. In some embodiments, the concentration of sodium phosphate dibasic is about 0.2% (w/v) of the oral pharmaceutical composition. In some embodiments, the concentration of sodium phosphate dibasic is no more than 1.3% (w/v) of the oral pharmaceutical composition. In some embodiments, the concentration of sodium phosphate dibasic is no more than 2% (w/v) of the oral pharmaceutical composition.

Excipients: Solvent

In some embodiments, the solvent comprises one or more of glycerol, alcohol, propylene glycol, water, or a combination thereof.

In some embodiments, the solvent is glycerol. In some embodiments, the concentration of glycerol is between 5% and 99% (w/v) of the oral pharmaceutical composition. In some embodiments, the concentration of glycerol is between 8% and 12% (w/v) of the oral pharmaceutical composition. In some embodiments, the concentration of glycerol is no more than 10% (w/v) of the oral pharmaceutical composition. In some embodiments, the concentration of glycerol is about 10% (w/v) of the oral pharmaceutical composition. In some embodiments, the concentration of glycerol is no more than 70% (w/v) of the oral pharmaceutical composition. In some embodiments, the concentration of glycerol is no more than 94% (w/v) of the oral pharmaceutical composition.

In some embodiments, the solvent is alcohol. In some embodiments, the concentration of alcohol is between 0.1% and 0.5% (v/v) of the oral pharmaceutical composition. In some embodiments, the concentration of alcohol is less than 0.5% (v/v) of the oral pharmaceutical composition. In some embodiments, the concentration of alcohol is no more than 0.5% (v/v) of the oral pharmaceutical composition. In some embodiments, the concentration of alcohol is about 0.10% (v/v) of the oral pharmaceutical composition. In some embodiments, the alcohol is 95% USP.

In some embodiments, the solvent is propylene glycol. In some embodiments, the concentration of propylene glycol is between 1% and 99% (w/v) of the oral pharmaceutical composition. In some embodiments, the concentration of propylene glycol is between 6.5% and 13% (w/v) of the oral pharmaceutical composition. In some embodiments, the concentration of propylene glycol is no more than 5% (w/v) of the oral pharmaceutical composition. In some embodiments, the concentration of propylene glycol is no more than 10% (w/v) of the oral pharmaceutical composition. In some embodiments, the concentration of propylene glycol is no more than 92% (w/v) of the oral pharmaceutical composition.

In some embodiments, the oral pharmaceutical composition comprises water. In some embodiments, the solvent is water. In some embodiments the concentration of water is less than or equal to 99% v/w of the oral pharmaceutical composition.

In some embodiments the pharmaceutical composition is a composition of any one of Formulations 1-7 as set out in Table 1 or the formulation as set out in Table 4.

The pharmaceutical compositions described herein can be made using methods known in the art and commercially available reagents.

Method of Treating Infection in a Patient Using the Disclosed Pharmaceutical Composition In an aspect of the present disclosure, a method of treating an infection in a patient is provided. The method comprises a step of administering to the patient an effective amount of an oral pharmaceutical composition provided herein, such as, for example an oral pharmaceutical composition comprising 1) metronidazole or a pharmaceutically acceptable salt thereof, and magnesium aluminum silicate; or 2) metronidazole or a pharmaceutically acceptable salt thereof, magnesium aluminum silicate, and at least one flavoring agent.

In some embodiments, the patient is a mammalian patient, such as, but not limited to, a human, non-human primate, cat, dog, rabbit, horse, cow, pig, sheep or goat.

Several anaerobic organism are susceptible to metronidazole, including gram-positive anaerobes such as *Clostridium* species, *Eubacterium* species, Peptococcus species, *Peptostreptococcus* species; Gram-negative anaerobes, including *Bacteroides fragilis* group and *Fusobacterium* species and, certain protozoal parasites. Metronidazole is bactericidal in that its action results in death of the organism.

As used herein, "treatment" with metronidazole is refers to one or more of the following: (1) clearance of the infection, in which the impeding pathogen is no longer present in the patient; (2) reduction in burden of infection, in which the pathogen is present at reduced levels; (3) decreasing or eradicating the signs and symptoms of infection (e.g., diarrhea for CDI, fever for systemic infections); and (4) treatment of asymptomatic sexual partners in the instance of *T. vaginalis* infection. One or more methods for measuring clearance, reduction, decrease or eradication, and treatment of asymptomatic patients are known to those skilled in the art.

In some embodiments, the method is for treating a bacterial infection. Bacterial infections to be treated with metronidazole are well known to the skilled artisan. In some embodiments, the bacterial infection is caused by a gram-positive bacterium. In some embodiments, the bacterial infection is caused by a gram-negative bacterium. In some embodiments, the bacterial infection is caused by an aerobic bacterium. In some embodiments, the bacterial infection is caused by an anaerobic bacterium. In some preferred embodiments, the bacterial infection is an acute anaerobic infection.

A person of ordinary skill in the art is well-positioned to determine groups and/or species of bacteria that may be treated with metronidazole. In some embodiments, the bacterial infection is caused by a *Clostridium* species. In some embodiments, the bacterial infection is caused by a *Eubacterium* species. In some embodiments, the bacterial infection is caused by a Peptococcus species. In some embodiments, the bacterial infection is caused by a *Peptostreptococcus* species. In some embodiments, the bacterial infection is caused by a member of *Bacteroides fragilis* group. In some embodiments, the bacterial infection is caused by a *Fusobacterium* species. In some embodiments, the bacterial infection is caused by a *Prevotella* species. In some embodiments, the bacterial infection is caused by *Clostridium difficile*.

In some embodiments, the method is for treating a fungal infection. Fungal infections to be treated with metronidazole are well known to the skilled artisan. In some preferred embodiments, the fungal infection is an acute infection.

In some embodiments, the method is for treating a protozoan infection. Protozoan infections to be treated with metronidazole are well known to the skilled artisan. In some preferred embodiments, the protozoan infection is an acute infection. In some embodiments, the protozoan infection is caused by *Entamoeba histolytica*. In some embodiments, the protozoan infection is caused by *Trichomonas vaginalis*.

In some embodiments, the method is for treating amebiasis. In some embodiments, the method is for treating pelvic inflammatory disease. In some embodiments, the method is for treating endocarditis. In some embodiments, the method is for treating bacterial vaginosis. In some embodiments, the method is for treating dracunculiasis. In some embodiments, the method is for treating giardiasis. In some embodiments, the method is for treating trichomoniasis.

The pharmaceutical compositions of the present disclosure may be administered to patients via oral administration; various routes of oral administration are well known to the skilled artisan. In some embodiments, the oral pharmaceutical composition is administered to the patient once per day (QD). In some embodiments, the oral pharmaceutical composition is administered to the patient twice per day (BID). In some embodiments, the oral pharmaceutical composition is administered to the patient three times per day (TID). In some embodiments, the oral pharmaceutical composition is administered to the patient four times per day (QID).

The oral pharmaceutical compositions of the present disclosure may be administered to patients in an effective amount. As used herein, the term "effective amount" refers to a therapeutically effective amount such as, for example, the amount of the composition that, upon administration to a patient, is sufficient to achieve the intended purpose (e.g., treatment, inhibition or prophylaxis of an infection). The amount may vary from one patient to another and may depend upon one or more factors, such as, for example, patient gender, age, body weight, patient's health history, and/or the underlying cause of the condition to be prevented, inhibited and/or treated.

The amount of metronidazole used for the methods of the present disclosure may provide an acceptable rate of change and maintains desired response at a beneficial level (e.g., a level sufficient to clear the infection, reduce the burden of infection, decrease or eradicate signs and symptoms of infection or sufficient to treat asymptomatic sexual partners in the instance of *T. vaginalis* infection). An effective amount of the oral pharmaceutical compositions used in the methods of the present disclosure may be readily ascertained by one of ordinary skill in the art using publicly available materials and procedures. In some embodiments, the effective amount of metronidazole to be administered may be quantified by determining milligrams of metronidazole per kilogram of patient body weight. In some embodiments, the effective amount of metronidazole to be administered may be quantified by determining milligrams of metronidazole in a "single dose" and/or according to the "total daily dose" to be administered to the patient.

In some embodiments, the effective amount of the oral pharmaceutical composition is between 250 mg and 4000 mg of metronidazole per day as a total daily dose. In some embodiments, the effective amount of the oral pharmaceutical composition is between 500 mg and 4000 mg of metronidazole per day as a total daily dose. In some embodiments, the effective amount of the oral pharmaceutical composition is between 1000 mg and 4000 mg of metronidazole per day as a total daily dose. In some embodiments, the effective amount of the oral pharmaceutical composition is between 1500 mg and 4000 mg of metronidazole per day as a total daily dose. In some embodiments, the effective amount of the oral pharmaceutical composition is between 2000 mg and 4000 mg of metronidazole per day as a total daily dose.

In some embodiments, the effective amount of the oral pharmaceutical composition is between 200 mg and 2000 mg of metronidazole as a single daily dose. In some embodiments, the effective amount of the oral pharmaceutical composition is between 250 mg and 2000 mg of metronidazole as a single daily dose. In some embodiments, the effective amount of the oral pharmaceutical composition is between 500 mg and 2000 mg of metronidazole as a single daily dose. In some embodiments, the effective amount of the oral pharmaceutical composition is between 750 mg and 2000 mg of metronidazole as a single daily dose. In some embodiments, the effective amount of the oral pharmaceutical composition is between 1000 mg and 2000 mg of metronidazole as a single daily dose. In some embodiments, the effective amount of the oral pharmaceutical composition is between 1250 mg and 2000 mg of metronidazole as a single daily dose. In some embodiments, the effective amount of the oral pharmaceutical composition is between 1500 mg and 2000 mg of metronidazole as a single daily dose.

In some embodiments, the effective amount of the oral pharmaceutical composition is administered 3 or 4 times daily. In some embodiments, the effective amount of the oral pharmaceutical composition is between 5 mg/kg of metronidazole and 10 mg/kg of metronidazole administered every 6 or 8 hours to the patient. In some embodiments, the effective amount of the oral pharmaceutical composition is about 5 mg/kg of metronidazole administered every 6 or 8 hours to the patient. In some embodiments, the effective amount of the oral pharmaceutical composition is about 7.5 mg/kg of metronidazole administered every 6 or 8 hours to the patient. In some embodiments, the effective amount of the oral pharmaceutical composition is about 10 mg/kg of metronidazole administered every 6 or 8 hours to the patient.

In some embodiments, the effective amount of the oral pharmaceutical composition is between 20 mg/kg of metronidazole and 50 mg/kg of metronidazole administered daily to the patient. In some embodiments, the effective amount of the oral pharmaceutical composition is about 20 mg/kg of metronidazole administered daily to the patient. In some embodiments, the effective amount of the oral pharmaceutical composition is about 25 mg/kg of metronidazole administered daily to the patient. In some embodiments, the effective amount of the oral pharmaceutical composition is about 30 mg/kg of metronidazole administered daily to the patient. In some embodiments, the effective amount of the oral pharmaceutical composition is about 35 mg/kg of metronidazole administered daily to the patient. In some embodiments, the effective amount of the oral pharmaceutical composition is about 40 mg/kg of metronidazole administered daily to the patient.

In some embodiments, the oral pharmaceutical composition provided herein is for veterinary usage. For example, metronidazole is currently used to treat giardiasis in cats and dogs. In some embodiments, the composition provided herein may be used to treat giardiasis in cats and/or dogs.

It is contemplated herein that the composition provided herein may be used to treat a veterinary patient (such as a non-human mammal) in need of treatment for one or more of the following: intestinal amebiasis; intestinal balantidiasis intestinal trichomoniasis (e.g., in cats or dogs); inflammatory bowel disease (e.g., in cats or dogs); antibiotic-associated colitis; clostridial colitis (e.g., in horses); hepatic encephalopathy (e.g., in cats and dogs); endometritis (e.g., in horses); or *Helicobacter* species infections (e.g., in cats or dogs); periodontal infections (e.g., in cats or dogs).

It is contemplated herein that the composition provided herein may be used to treat a veterinary patient (such as a non-human mammal) in need of treatment or prophylaxis for one or more of the following bacterial infections: bone and/joint infections (treatment); central nervous system infections (treatment); intra-abdominal infections (treatment); colorectal perioperative infections (prophylaxis); lower respiratory tract infections (treatment); bacterial septicemia (treatment); and skin and/or soft tissue infections (treatment).

In some embodiments of the disclosed methods, the patient is a geriatric patient. As used herein, the term "geriatric" refers generally to an adult individual who has reached old age, such as, for example, ages 60, 65, 70, 80, 85, 90, 95, 100 or older or any age there between. As a skilled person will appreciate, a geriatric patient may, in some cases, be younger than 60. The taste masking aspects of the compositions of metronidazole provided in the present disclosure are desirable to patients, physicians, and caregivers for the geriatric patient population. A person of ordinary skill in the art can readily ascertain the geriatric patients that may benefit from administration of the oral pharmaceutical compositions of the present disclosure.

In some embodiments of the disclosed methods, the patient is a pediatric patient, such as, for example a patient who is age 25, 20, 15, 10, 5 or younger or any age there between. As used herein, the term "pediatric" refers generally to children under the age of twenty-two years old, in particular children under the age of eighteen years old. The taste masking aspects of the compositions of metronidazole provided in the present disclosure are desirable to patients, physicians, and caregivers for the treatment of the pediatric patient population. A person of ordinary skill in the art may readily ascertain the pediatric patients that would benefit from administration of the oral pharmaceutical compositions of the present disclosure.

In some embodiments, the effective amount of the oral pharmaceutical composition is between 15 mg/kg of metronidazole and 50 mg/kg of metronidazole administered every 6 or 8 hours to the pediatric patient. In some embodiments, the effective amount of the oral pharmaceutical composition is between 25 mg/kg of metronidazole and 40 mg/kg of metronidazole administered every 6 or 8 hours to the pediatric patient. In some embodiments, the effective amount of the oral pharmaceutical composition is about 30 mg/kg of metronidazole administered to the pediatric patient. In some embodiments, the effective amount of the oral pharmaceutical composition is no more than 2000 mg administered to the pediatric patient per day.

One or more of the taste masking properties of the compositions provided herein may be measured relative to other compositions of metronidazole known in the art. For example, the taste-masking of the disclosed composition may be measured relative to a composition of metronidazole that does not comprise a flavoring agent. For example, the taste-masking of the disclosed composition may be measured relative to a composition of metronidazole comprising crushed metronidazole tablets. For example, the taste-masking of the disclosed composition may be measured relative to a composition of metronidazole comprising a chocolate flavoring agent or crushed into a food, such as apple sauce.

The following examples and figures are included to demonstrate preferred embodiments of the invention. It should be appreciated by those of skill in the art that the details disclosed in the examples and/or figures represents details discovered by the inventors that function well in the practice of the invention, and thus may be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Manufacture of Metronidazole Formulations

Two strategies were used to manufacture a metronidazole formulation comprising MgAlSi, methyl paraben, propyl paraben, microcrystalline cellulose, sucrose, sucralose, sodium phosphate monobasic, sodium phosphate dibasic, metronidazole, glycerol, alcohol, flavors (strawberry, raspberry and peppermint), and water. The equipment used for manufacture is known in the art and commercially available. As a skilled person will appreciate, further optimization may be required to scale-up production of the formulations provided herein.

The manufacturing strategies involve combining three taste masking steps. These steps are: 1) placing the metronidazole within a semi/pseudo syrup; 2) suspending the metronidazole-containing semi/pseudo syrup in the MgAlSi to trap the metronidazole in-between the MgAlSi clay platelets; and 3) adding various sweeteners and/or flavors. When manufacturing a metronidazole formulation that does not contain any flavoring agents, the step of adding the flavoring agents is omitted.

Figure 3:
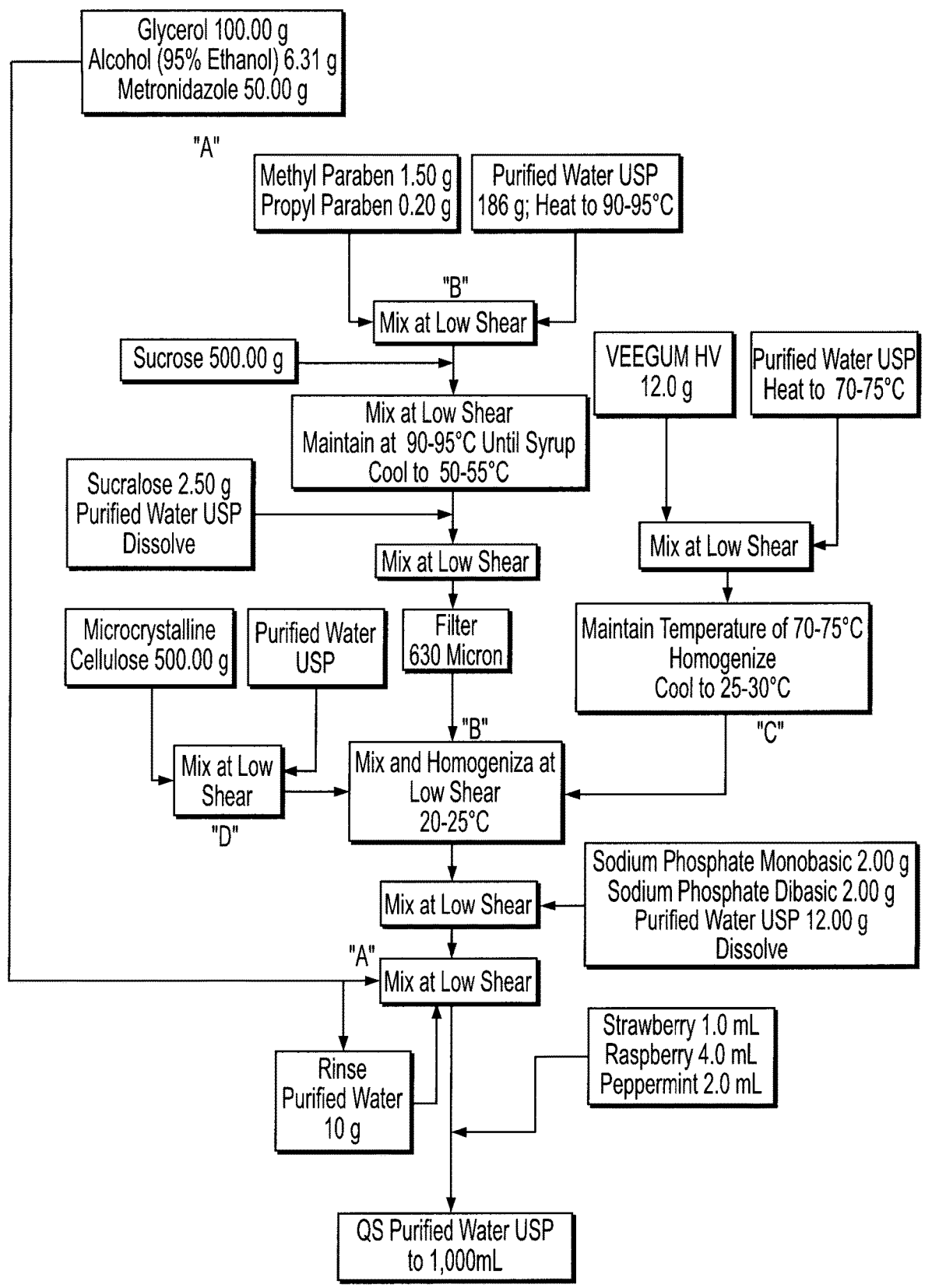
FIG. 3 shows a schematic of a process for making a metronidazole pharmaceutical formulation.

Strategy 1: The protocol for strategy 1 is provided below and illustrated in FIG. 3.

Step 1: In a stainless steel vessel equipped with a low shear mixer, disperse Metronidazole into Glycerol and Alcohol (95% Ethanol). Mix to create uniform slurry or a pseudo syrup (i.e., in a syrup-like phase). Mix continuously until the addition to main vessel. (See Part A, FIG. 3).

| | |
|---|---|
| Glycerol | 100.00 g |
| Alcohol (95% Ethanol) | 6.31 g |
| Metronidazole | 50.00 g |

Step 2: In a jacketed stainless steel vessel equipped with a low shear mixer, add 186 g Purified Water USP. Heat Purified Water to 90-95° C. Dissolve methyl paraben and propyl paraben using low shear mixing. (See Part B, FIG. 3).

| | |
|---|---|
| Methyl Paraben | 1.50 g |
| Propyl Paraben | 0.20 g |

Step 3: Add and dissolve sucrose into Part B using low shear mixing while maintaining temperature of 90-95° C.

| | |
|---|---|
| Sucrose | 500.00 g |

Step 4: Cool Part B to 50-55° C.

Step 5: In a stainless steel vessel, sucralose in 4 g of Purified Water USP. Add to Part B using low shear mixing.

| | |
|---|---|
| Sucralose | 2.50 g |

Step 6: Filter Part B through a 630 micron filter and collect in a stainless steel vessel.

Step 7: In a jacketed stainless steel vessel equipped with a low shear mixer and homogenizer, add 420 g of Purified Water USP. Heat purified water to 70-75° C. With low shear mixing disperse magnesium aluminum silicate Type IC (VEEGUM HV) for 30 minutes. (See Part C, FIG. 3).

| | |
|---|---|
| Purified Water USP | 420.00 g |
| VEEGUM HV | 12.00 g |

Step 8: Maintain temperature of 70-75° C., low shear mix between 15-20 rpm, homogenize at high speed, vacuum 0.4-0.6 bar for 10 minutes.

Step 9: Cool Part C to 25-30° C.

Step 10: In a stainless steel vessel equipped with low shear mixer, disperse Microcrystalline Cellulose in 120 g Purified Water USP. Mix for 30 minutes. (See Part D, FIG. 3).

| | |
|---|---|
| Microcrystalline Cellulose | 6.00 g |

Step 11: Transfer Part B and Part D into the mixer containing Part C. Set mixer to 25-30° C., low shear mixer at 18 rpm, homogenizer high speed, and vacuum 0.4-0.6 bar. Mix and homogenize for 10 minutes.

Step 12: In a separate vessel dissolve Sodium Phosphate Monobasic and Sodium Phosphate Dibasic into 12 g of Purified Water USP. Add to step 11 mixture and mix with low shear mixing set between 15-20 rpm.

| | |
|---|---|
| Sodium Phosphate Monobasic | 2.00 g |
| Sodium Phosphate Dibasic | 2.00 g |
| Purified Water USP | 12.00 g |

Step 13: Add Part A to mixer with low shear mixing set between 15-20 rpm. Vessel may be rinsed with 10 g purified water up to 3 times and added to the mixer with low shear mixing.

Step 14: Add flavoring agents (Raspberry, Strawberry, Peppermint) to the step 13 mixture. Once specific gravity of final formulation is determined, QS to 1,000 mL final volume with purified water USP.

| | |
|---|---|
| Raspberry | 4.0 mL |
| Strawberry | 1.0 mL |
| Peppermint | 2.0 mL |
| Purified Water USP | Up to 1,000 mL |

Step 15: Mix final formulation low shear 15-20 rpm and homogenize for 20 minutes under 0.4-0.6 bar.

Step 16: Transfer suspension into a stainless steel holding tank through a 630 micron filter. Do not store for more than 48 hours without mixing prior to filling.

Figure 4:
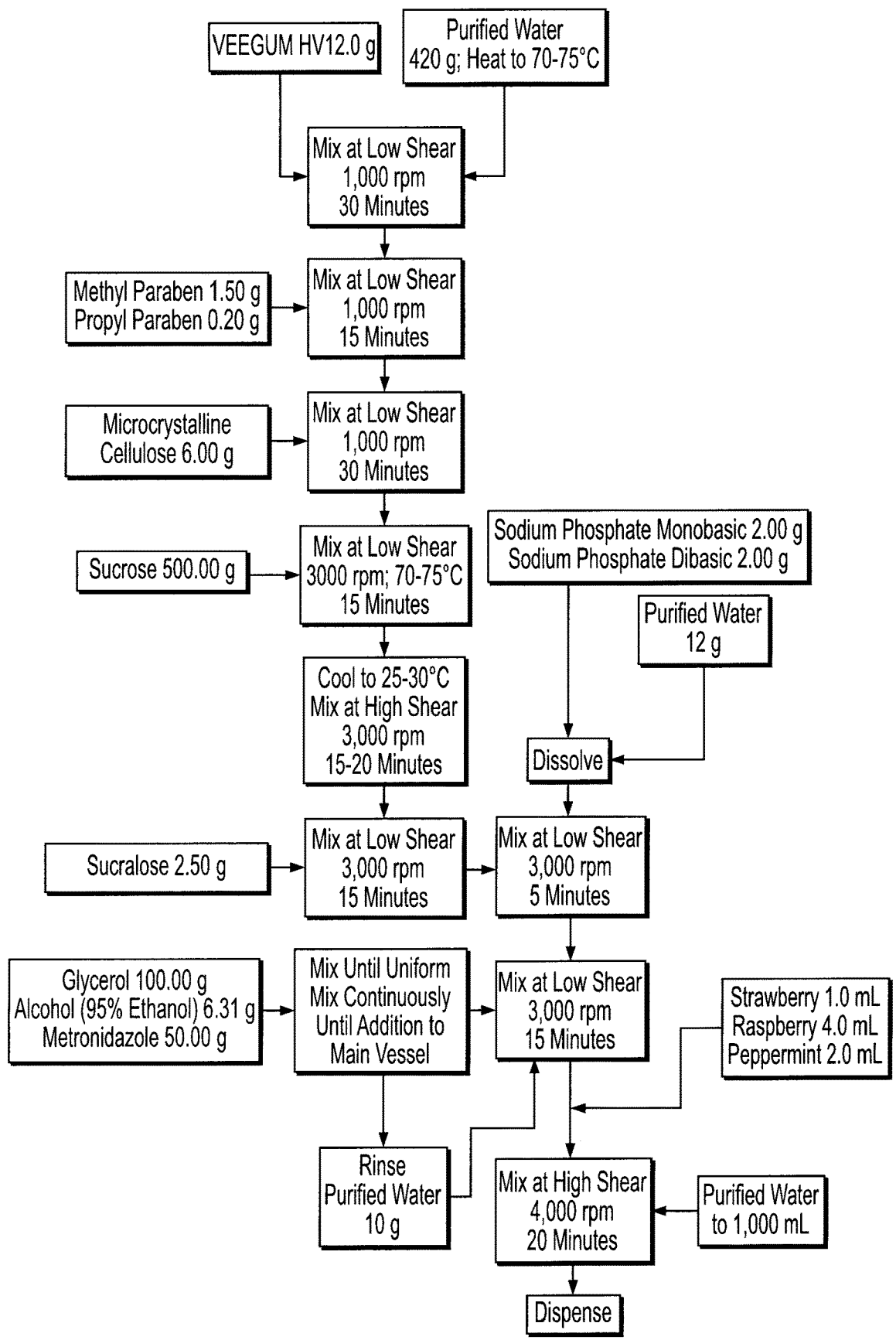
FIG. 4 shows a schematic of a process for making a metronidazole pharmaceutical formulation.

Strategy 2: The protocol for strategy 2 is provided below and illustrated in FIG. 4. In strategy 2, Sylverson Homogenizers were used for high and low shear mixing. To achieve high shear mixing a fine screen was attached to the impeller head of the homogenizer. To achieve low shear mixing the screen was removed.

Step 1: In a stainless steel vessel equipped with a low shear mixer, disperse metronidazole into glycerol and alcohol (95% ethanol). Mix to create uniform slurry. Mix continuously until the addition to main vessel.

| | |
|---|---|
| Glycerol | 100.00 g |
| Alcohol (95% Ethanol) | 6.31 g |
| Metronidazole | 50.00 g |

Step 2: In a second stainless steel vessel equipped with a low shear mixer and homogenizer, add 420 g of purified water USP. Heat purified water to 70-75° C. With low shear mixing (~1,000 rpm) disperse magnesium aluminum silicate Type IC (VEEGUM HV) for 30 minutes.

| | |
|---|---|
| Purified Water USP | 420.00 g |
| VEEGUM HV | 12.00 g |

Step 3: To step 2 mixture, add methyl paraben and propyl paraben and mix at low shear (~1,000 rpm) for 15 minutes to dissolve.

| | |
|---|---|
| Methyl Paraben | 1.50 g |
| Propyl Paraben | 0.20 g |

Step 4: To step 3 mixture, disperse microcrystalline cellulose and mix (~1,000 rpm) for 30 minutes.

| | |
|---|---|
| Microcrystalline Cellulose | 6.00 g |

Step 5: To step 4 mixture, add and dissolve sucrose using low shear mixing (~3000 rpm) for 15 minutes while maintaining temperature of 70-75° C.

| | |
|---|---|
| Sucrose | 500.00 g |

Step 6: Cool step 5 mixture to 25-30° C. Mix and homogenize at high shear (~3,000 rpm) for 15-20 minutes.

Step 7: To step 6 mixture add and dissolve Sucralose using low shear mixing (~3,000 rpm) for 15 minutes.

| | |
|---|---|
| Sucralose | 2.50 g |

Step 8: In a separate vessel dissolve sodium phosphate monobasic and sodium phosphate dibasic into 12 g of purified water USP, mixing with magnetic stir bar. Add to step 7 mixture and mix with low shear mixing (~3,000 rpm) for 5 minutes.

| | |
|---|---|
| Sodium Phosphate Monobasic | 2.00 g |
| Sodium Phosphate Dibasic | 2.00 g |
| Purified Water USP | 12.00 g |

Step 9: Add active phase slurry from step 1 to step 8 slurry. Mix with low shear mixing (~3,000 rpm) for 15 minutes. Vessel may be rinsed with 10 g purified water up to 3 times, with rinsed product added to the Step 8 slurry.

Step 10: Add flavoring agents (raspberry, strawberry, peppermint) to the step 9 mixture. Once specific gravity of final formulation is determined, QS to 1,000 mL final volume with purified water USP. Homogenize (high shear, —4,000 rpm) for a minimum of 20 minutes.

| | |
|---|---|
| Raspberry | 4.0 mL |
| Strawberry | 1.0 mL |
| Peppermint | 2.0 mL |
| Purified Water USP | Up to 1,000 mL |

Step 11: Bottle in suitable container. Do not store for more than 48 hours without mixing prior to filling.

Example 2: Metronidazole Formulations

Seven (7) pharmaceutical formulations of metronidazole were made. The formulations were assigned a Formulation Identifier (number 1-7). Table 1 shows detail for each formulation, including the concentration of key excipients used in each of the formulations.

TABLE 1

Formulations and Key Excipients (all formulae stored at ambient temperature; all formulae described as off-white liquid suspension)

| Formulation Identifier | R&D Number | API | Excipients, sweeteners, and flavoring agents (% w/v unless otherwise indicated) [Function] | Procurement Details: Supplier, Name, Identity [CAS#] |
|---|---|---|---|---|
| ATI-1501-2 (Formulation 2) | 15087 | Metronidazole (250 mg/5 mL) | Methyl Paraben (0.15%) [Preservative] Propyl Paraben (0.02%) [Preservative] Sucrose NF (50.00%) [Sweetener] Saccharin Sodium (0.25%) [Sweetener] Sodium Phosphate Monobasic (0.20%) [Buffer] Sodium Phosphate Dibasic (0.20%) [Buffer] Magnesium Aluminum Silicate Type 1C (VEEGUM HV) (1.20%) [Suspending Agent] Microcrystalline Cellulose (0.60%) [Texture Modifier] Propylene Glycol (13.00%) [Solvent] Primary Flavour: Natural Cherry Flavour (0.20%) [Flavour] Secondary Flavour: Natural Cherry Flavour (0.15%) [Flavour] Alcohol 95% USP (0.80%) [Solvent] Purified Water USP (QS to 1 L) [Solvent] | Gujarat Organics Ltd., Methyl Paraben BP/EP/USP/NF, 99-76-3 Gujarat Organics Ltd., Propyl Paraben BP/EP/USP/NF, 94-13-3 A&C Ltd., Sucrose NF, 57-50-1 A&C Ltd., Sodium Phosphate Monobasic Anhydrous USP, 7558-80-7 ICL Performance Products LP, Disodium Phosphate Anhydrous, 7558-79-4 Vanderbilt Minerals LLC, Mixture of Smectite Clay (<99%), 12199-37-0 and Quartz (0.8%), 14808-60-7 A&C, Cellulose Microcrystalline NF, 9004-34-6 Commercial Alcohols, Ethyl Alcohol 94.9-60.0% USP, 64-17-5 7732-18-5 |
| ATI-1501-5 (Formulation 5) | | Metronidazole (250 mg/5 mL) | Methyl Paraben (0.15%) [Preservative] Propyl Paraben (0.02%) [Preservative] Sucrose NF (50.00%) [Sweetener] Saccharin Sodium (0.25%) [Sweetener] Sodium Phosphate Monobasic (0.20%) [Buffer] Sodium Phosphate Dibasic (0.20%) [Buffer] Magnesium Aluminum Silicate-Type IC | Gujarat Organics Ltd., Methyl Paraben BP/EP/USP/NF, 99-76-3 Gujarat Organics Ltd., Propyl Paraben BP/EP/USP/NF, 94-13-3 A&C Ltd., Sucrose NF, 57-50-1 A&C Ltd., Sodium Phosphate Monobasic Anhydrous USP, 7558-80-7 |

TABLE 1-continued

Formulations and Key Excipients (all formulae stored at ambient temperature; all formulae described as off-white liquid suspension)

| Formulation Identifier | R&D Number | API | Excipients, sweeteners, and flavoring agents (% w/v unless otherwise indicated) [Function] | Procurement Details: Supplier, Name, Identity [CAS#] |
|---|---|---|---|---|
| | | | (VEEGUM HV) (1.20%) [Suspending Agent]<br>Microcrystalline Cellulose (0.60%) [Texture Modifier]<br>Glycerol (10.00%) [Solvent]<br>Raspberry flavour (0.80% v/v) [Flavour]<br>Alcohol 95% USP (0.80% v/v) [Solvent]<br>Purified Water USP (QS to 1 L) [Solvent] | ICL Performance Products LP, Disodium Phosphate Anhydrous, 7558-79-4<br>Vanderbilt Minerals LLC, Mixture of Smectite Clay (<99%), 12199-37-0 and Quartz (0.8%), 14808-60-7<br>A&C, Cellulose Microcrystalline NF, 9004-34-6<br>Dow Chemical Company, OPTIM ™, 56-81-5<br>Commercial Alcohols, Ethyl Alcohol 94.9-60.0% USP, 64-17-5<br>7732-18-5 |
| ATI-1501-7 (Formulation 7) | 16062 | Metronidazole (250 mg/5 mL) | Methyl Paraben (0.15%) [Preservative]<br>Propyl Paraben (0.02%) [Preservative]<br>Sucrose NF (50.00%) [Sweetener]<br>Saccharin Sodium (0.25%) [Sweetener]<br>Sodium Phosphate Monobasic (0.20%) [Buffer]<br>Sodium Phosphate Dibasic (0.20%) [Buffer]<br>Magnesium Aluminum Silicate-Type IC (VEEGUM HV) (1.20%) [Suspending agent]<br>Microcrystalline Cellulose (0.60%) [Texture Modified]<br>Glycerol (10.00%) [Solvent]<br>Strawberry flavour (0.10% v/v) [Flavour]<br>Raspberry Flavour (0.40% v/v) [Flavour]<br>Alcohol 95% USP (0.80% v/v) [Solvent]<br>Purified Water USP (QS to 1 L) [Solvent] | Gujarat Organics Ltd., Methyl Paraben BP/EP/USP/NF, 99-76-3<br>Gujarat Organics Ltd., Propyl Paraben BP/EP/USP/NF, 94-13-3<br>A&C Ltd., Sucrose NF, 57-50-1<br>A&C Ltd., Sodium Phosphate Monobasic Anhydrous USP, 7558-80-7<br>ICL Performance Products LP, Disodium Phosphate Anhydrous, 7558-79-4<br>Vanderbilt Minerals LLC, Mixture of Smectite Clay (<99%), 12199-37-0 and Quartz (0.8%), 14808-60-7<br>A&C, Cellulose Microcrystalline NF, 9004-34-6<br>Dow Chemical Company, OPTIM ™, 56-81-5<br>Commercial Alcohols, Ethyl Alcohol 94.9-60.0% USP, 64-17-5<br>7732-18-5 |
| ATI-1501-3 (Formulation 3) | 16077 | Metronidazole (250 mg/5 mL) | Methyl Paraben (0.15%) [Preservative]<br>Propyl Paraben (0.02%) [Preservative]<br>Sucrose NF (50.00%) [Sweetening Agent]<br>Sucralose (0.25%) [Sweetening Agent]<br>Sodium Phosphate Monobasic (0.20%) [Buffer]<br>Sodium Phosphate Dibasic (0.20%) [Buffer]<br>Magnesium Aluminum Silicate Type 1C (VEEGUM HV) (1.20%) [Suspending Agent]<br>Microcrystalline Cellulose (0.60%) [Texture Modifier]<br>Glycerol (10.00%) [Solvent]<br>Raspberry (0.40% v/v) [Flavour]<br>Strawberry (0.10% v/v) [Flavour]<br>Peppermint (0.01% v/v) [Flavour]<br>Alcohol 95% USP (0.80% v/v) [Solvent]<br>Purified Water USP (QS to 1 L) [Solvent] | Gujarat Organics Ltd., Methyl Paraben BP/EP/USP/NF, 99-76-3<br>Gujarat Organics Ltd., Propyl Paraben BP/EP/USP/NF, 94-13-3<br>A&C Ltd., Sucrose NF, 57-50-1<br>A&C Ltd., Sodium Phosphate Monobasic Anhydrous USP, 7558-80-7<br>ICL Performance Products LP, Disodium Phosphate Anhydrous, 7558-79-4<br>Vanderbilt Minerals LLC, Mixture of Smectite Clay (<99%), 12199-37-0 and Quartz (0.8%), 14808-60-7<br>A&C, Cellulose Microcrystalline NF, 9004-34-6<br>Dow Chemical Company, OPTIM ™, 56-81-5<br>Givaudan, Natural Peppermint Flavor WONF<br>Commercial Alcohols, Ethyl Alcohol 94.9-60.0% USP, 64-17-5<br>7732-18-5 |
| ATI-1501-4 (Formulation 4) | 16077 | Metronidazole (250 mg/5 mL) | Methyl Paraben (0.15%) [Preservative]<br>Propyl Paraben (0.02%) [Preservative]<br>Sucrose NF (50.00%) [Sweetening Agent]<br>Sucralose (0.25%) [Sweetening Agent]<br>Sodium Phosphate Monobasic (0.20%) [Buffer]<br>Sodium Phosphate Dibasic (0.20%) [Buffer]<br>Magnesium Aluminum Silicate Type 1C (VEEGUM HV) (1.20%) [Suspending Agent]<br>Microcrystalline Cellulose (0.60%) [Texture Modifier]<br>Glycerol (10.00%) [Solvent]<br>Alcohol 95% USP (0.80% v/v) [Solvent]<br>Purified Water USP (QS to 1 L) [Solvent] | Gujarat Organics Ltd., Methyl Paraben BP/EP/USP/NF, 99-76-3<br>Gujarat Organics Ltd., Propyl Paraben BP/EP/USP/NF, 94-13-3<br>A&C Ltd., Sucrose NF, 57-50-1<br>A&C Ltd., Sodium Phosphate Monobasic Anhydrous USP, 7558-80-7<br>ICL Performance Products LP, Disodium Phosphate Anhydrous, 7558-79-4<br>Vanderbilt Minerals LLC, Mixture of Smectite Clay (<99%), 12199-37-0 and Quartz (0.8%), 14808-60-7<br>A&C, Cellulose Microcrystalline NF, 9004-34-6<br>Dow Chemical Company, OPTIM ™, 56-81-5<br>Commercial Alcohols, Ethyl Alcohol 94.9-60.0% USP, 64-17-5<br>7732-18-5 |
| ATI-1501-1 (Formulation 1) | 16077 | Metronidazole (250 mg/5 mL) | Methyl Paraben (0.15%) [Preservative]<br>Propyl Paraben (0.02%) [Preservative]<br>Sucrose NF (50.00%) [Sweetening Agent]<br>Sucralose (0.25%) [Sweetening Agent]<br>Sodium Phosphate Monobasic (0.20%) [Buffer]<br>Sodium Phosphate Dibasic (0.20%) [Buffer]<br>Magnesium Aluminum Silicate Type 1C (VEEGUM HV) (1.20%) [Suspending Agent]<br>Microcrystalline Cellulose (0.60%) [Texture Modifier]<br>Glycerol (10.00%) [Solvent]<br>Raspberry (0.40% v/v) [Flavour]<br>Strawberry (0.10% v/v) [Flavour] | Gujarat Organics Ltd., Methyl Paraben BP/EP/USP/NF, 99-76-3<br>Gujarat Organics Ltd., Propyl Paraben BP/EP/USP/NF, 94-13-3<br>A&C Ltd., Sucrose NF, 57-50-1<br>A&C Ltd., Sodium Phosphate Monobasic Anhydrous USP, 7558-80-7<br>ICL Performance Products LP, Disodium Phosphate Anhydrous, 7558-79-4<br>Vanderbilt Minerals LLC, Mixture of Smectite Clay (<99%), 12199-37-0 and Quartz (0.8%), 14808-60-7<br>A&C, Cellulose Microcrystalline NF, 9004-34-6<br>Dow Chemical Company, OPTIM ™, 56-81-5 |

TABLE 1-continued

Formulations and Key Excipients (all formulae stored at ambient temperature; all formulae described as off-white liquid suspension)

| Formulation Identifier | R&D Number | API | Excipients, sweeteners, and flavoring agents (% w/v unless otherwise indicated) [Function] | Procurement Details: Supplier, Name, Identity [CAS#] |
|---|---|---|---|---|
| ATI-1501-6 (Formulation 6) | 16077 | Metronidazole (250 mg/5 mL) | Peppermint (0.20% v/v) [Flavour] <br> Alcohol 95% USP (0.80% v/v) [Solvent] <br> Purified Water USP (QS to 1 L) [Solvent] <br> Methyl Paraben (0.15%) [Preservative] <br> Propyl Paraben (0.02%) [Preservative] <br> Sucrose NF (50.00%) [Sweetening Agent] <br> Sucralose (0.25%) [Sweetening Agent] <br> Sodium Phosphate Monobasic (0.20%) [Buffer] <br> Sodium Phosphate Dibasic (0.20%) [Buffer] <br> Magnesium Aluminum Silicate Type 1C (VEEGUM HV) (1.20%) [Suspending Agent] <br> Microcrystalline Cellulose (0.60%) [Texture Modifier] <br> Glycerol (10.00%) [Solvent] <br> Raspberry (0.80% v/v) [Flavour] <br> Peppermint (0.10% v/v) [Flavour] <br> Alcohol 95% USP (0.80% v/v) [Solvent] <br> Purified Water USP (QS to 1 L) [Solvent] | Givaudan, Natural Peppermint Flavor WONF <br> Commercial Alcohols, Ethyl Alcohol 94.9-60.0% USP, 64-17-5 <br> 7732-18-5 <br> Gujarat Organics Ltd., Methyl Paraben BP/EP/USP/NF, 99-76-3 <br> Gujarat Organics Ltd., Propyl Paraben BP/EP/USP/NF, 94-13-3 <br> A&C Ltd., Sucrose NF, 57-50-1 <br> A&C Ltd., Sodium Phosphate Monobasic Anhydrous USP, 7558-80-7 <br> ICL Performance Products LP, Disodium Phosphate Anhydrous, 7558-79-4 <br> Vanderbilt Minerals LLC, Mixture of Smectite Clay (<99%), 12199-37-0 and Quartz (0.8%), 14808-60-7 <br> A&C, Cellulose Microcrystalline NF, 9004-34-6 <br> Dow Chemical Company, OPTIM ™, 56-81-5 <br> Givaudan, Natural Peppermint Flavor WONF <br> Commercial Alcohols, Ethyl Alcohol 94.9-60.0% USP, 64-17-5 <br> 7732-18-5 |

Example 3: Palatability Study of Various Metronidazole Compositions in Healthy Volunteers The instant example provides a palatability study of the metronidazole pharmaceutical compositions of the present disclosure. Because palatability is comprised of multiple factors, the present study examined the overall taste, the perceived bitterness, and the acceptance of the texture and smell of the pharmaceutical compositions. The study was performed in five (5) healthy adult volunteers by having them rate the palatability (i.e., taste, bitterness, texture, and smell) of each of the formulations using validated subject-reporting methods commonly utilized for taste test studies, specifically, the modified 9-point Hedonic Scale (Peryam 1957, Peryam 1952). The results of the taste test study were analyzed using standard parametric statistics on the scores obtained from the reporting scales (mean, median, and standard deviation), as an indicator of the overall palatability of the metronidazole pharmaceutical compositions of the present disclosure. Because the pungent taste of metronidazole has been reported to linger for several minutes after the initial ingestion of the product, the present study had the subjects rate the palatability (using the parameters outlined above) at 15 seconds and 3 minutes following ingestion, to determine if the formulation had improved both the initial and lingering palatability of metronidazole.

The instant example was a blinded, investigational, taste test study, performed in five (5) healthy adult volunteers to assess the palatability of seven (7) different formulations of metronidazole pharmaceutical compositions of the present disclosure.

The primary objective of the instant example was to assess the palatability of each metronidazole oral suspension formulation using the modified 9-point Hedonic scale. This is a validated measure that is commonly used in the food industry to assess taste preference (Wichchukit 2015).

Subjects were asked to rate their like/dislike of a product, based on the following scale:
1=Dislike Extremely
2=Dislike Very Much
3=Dislike Moderately
4=Dislike Slightly
5=Neither Like nor Dislike
6=Like Slightly
7=Like Moderately
8=Like Very Much
9=Like Extremely Subjects were asked to use the scale to answer the following questions about the formulation at 15 seconds and 3 minutes after oral administration of the formulation:
How much do you like/dislike the overall taste of the formulation?
How much do you like/dislike the overall texture of the formulation?
How much do you like/dislike the formulation overall (taste, smell, texture)?

Subjects were also being asked to rate the degree of bitterness of the formulation based on the following scale:
1=Very bitter
2=Somewhat bitter
3=Not bitter The seven (7) pharmaceutical formulations of metronidazole described in Example 1 were evaluated in the instant example.

Each of the 5 subjects self-administered a single 1.5 mL sample of each formulation, for a total of seven samples over the course of the study. The 7 formulations were supplied in 170 g bottles. Immediately prior to preparation of the individual doses for each formulation, the contents of the bottle were mixed vigorously for 30 seconds (to ensure consistent distribution of the contents), by inverting the bottle back and forth. The dose for each of the 5 subjects was prepared by drawing 1.5 mL of the oral suspension formulation into 5 individual syringes (intended for use in the administration of oral suspensions), such that 1.5 mL of each formulation was drawn and prepared 5 times. This preparation method was repeated for all 7 formulations immediately prior to sampling by the subject. For the purposes of the taste test study, each subject self-administered 1.5 mL of the study agent by oral sampling.

Prior to the start of the study, each individual subject was randomized to receive each formulation in a specific order.

A research assistant assigned each subject a tasting station, where the subject completed the taste test study, and remained at for the duration of the study. Each station contained 7 pre-filled oral medical syringes in the order specified for each subject, and all relevant study materials (package of table water crackers, 250 mL bottle of water, rinse bucket, and score sheet/pencil for evaluation).

Fifteen minutes prior to the start of the taste test study, subjects arrived at their assigned tasting station. Subjects were instructed to sit and wait further instruction. The research assistant provided an overview of the study, by informing each subject that they were to taste a total of seven different formulations of oral suspension, and would be asked to evaluate each formulation under a specific set of parameters. The research assistant went through the score sheet with each subject and advised them on how much time was to be allotted for the taste and evaluation of each formulation, as well as the amount of time allotted between each tasting for palate cleansing. Subjects were instructed on how to cleanse their palate in between taste evaluations. If the subjects had any questions prior to the start of the study, the research assistant made every attempt to provide clarity until the subjects were comfortable with the study design.

The administration of the first formulation was considered time 0. Subjects were instructed by the research assistant to self-administer the oral suspension (via the oral medication syringe). Fifteen (15) seconds after administration of the suspension, subjects were asked to evaluate the taste of the oral suspension based on the following three parameters: the degree that they like the overall taste (score of 1-9), the degree of bitterness (score of 1-3), the degree that they like the texture of the formulation (score of 1-9), and the overall palatability (how much they like/dislike the oral suspension overall [score of 1-9]). The subjects were instructed to refrain from eating or drinking anything until 3 minutes after administration, at which time the research assistant once again asked them to rate the oral suspension (using the same parameters outlined above). Subjects then had 5 minutes to cleanse their palate (e.g., eat crackers, sip water, rinse their mouth), before the next formulation was evaluated. The duration of each evaluation, encompassing oral suspension administration, evaluation and cleansing, was 8 minutes (3 minutes to administer/evaluate the formulation, 5 minutes to wash-out/cleanse the palate). The study procedure outlined above was then repeated for the remaining 6 formulations.

At the end of the final evaluation period, subjects were asked to return their score sheets and pencils and dispose of any unused/unconsumed table water crackers and/or water. The oral medication syringes were disposed of using proper disposal methods by the research assistants.

Parametric statistical tests were performed on the scores provided by each subject including descriptive statistics such as the mean, median and standard deviation for each parameter examined, at both time points. These descriptive statistics were used to extrapolate the degree of palatability of each of the seven formulations. The seven formulations were ranked in terms of overall taste, degree of bitterness, texture, and overall palatability. For the purposes of a control, crushed metronidazole tablets were assigned a universal score of "1" (dislike extremely) and "1" (very bitter).

Subjects self-administered the formulations at set time intervals and evaluated the taste of the oral suspension based on the following three parameters: the degree that they like the overall taste (score of 1-9), the degree that they like the texture of the formulation (score of 1-9), the overall palatability (how much they like/dislike the oral suspension overall [score of 1-9]) and the degree of bitterness (score of 1 [very bitter], 2 [somewhat bitter], or 3 [not bitter]). Subjects performed these evaluations 15 seconds after administration of the formulation, and again at 3 minutes following administration. The evaluation of each formulation therefore produced two sets of scores and each score set was comprised of 4 different rankings based on the parameters outlined above.

Overall, the results produced consistent findings amongst the subjects. Formulations that contained peppermint consistently ranked higher on the "degree of like" scales, and were reported to be less bitter than formulations that did not contain peppermint. There was no apparent preference for flavor as there was no observable difference in ranking between the formulations that contained raspberry or strawberry flavors. However, formulations that did not contain any flavor agents were ranked considerably lower than those that did contain flavors and the formulations, such as Formulation 2 that contained a cherry flavor agent, did not score very high on the palatability or taste scale. All formulations were considered more palatable than crushed metronidazole tablets, even when the crushed metronidazole was re-suspended in food and/or beverage.

Formulation 1 comprised a combination of three flavors: Raspberry (0.4% concentration), Strawberry (0.1% concentration) and Peppermint (0.2% concentration). For Formula 1, the mean response to the first question (How much do you like/dislike the overall taste of the formulation?) was 6.0 at 15 seconds and 6.2 at 3 minutes; the mean response to the question "How much do you like/dislike the overall texture of the formulation?" was 6.0 at 15 seconds, and 6.4 at 3 minutes; the mean response to the question "How much do you like/dislike the formulation overall (taste, smell, texture)?" was 6.0 at both 15 seconds and 3 minutes. This formulation received a mean bitterness score of 2.8 at 15 seconds, and 2.6 at 3 minutes.

Formulation 2 comprised cherry flavor and propylene glycol as the solvent. With respect to taste, this formulation received mean scores of 3.6 and 3.2 at 15 seconds and 3 minutes respectively. When asked how much they liked the texture of this formulation, subjects provided a mean score of 4.8 and 4.4 (15 seconds and 3 minutes respectively). This formulation received a mean score of 3.2 and 3.4 when subjects were asked how much they liked the formulation overall, and the mean bitterness score was 1.6 and 2.2 at 15 seconds and 3 minutes, respectively, for both the overall taste and bitterness scores.

Formulation 3 produced a similar pattern of results to that of Formulation 1. As in Formulation 1, Formulation 3 comprised both Raspberry and Strawberry flavors at concentrations of 0.4% and 0.2% respectively. It also contained Peppermint, however, the concentration was lower (0.01% versus 0.2% in Formulation 1). The mean scores with respect to taste were higher at both 15 seconds and 3 minutes then they were for Formulation 1 (6.4 and 6.2 respectively), and subjects scored this formulation higher with respect to overall palatability as well (6.2 at both 15 seconds and 3 minutes). However, subjects appeared to prefer the texture of Formula 1. When subjects asked how much they liked the overall texture of this Formulation, Formula 3 received a mean score of 5.6 at 15 seconds and 5.8 at 3 minutes. This Formulation received a mean bitterness score of 2.6 and 2.2 at 15 seconds and 3 minutes respectively, suggesting that the bitterness was slightly less noticeable in this Formulation as compared with Formulation 1.

Formulation 4 comprised no flavors—only metronidazole and the non-flavored excipients. Formulation 4 was not well liked and received a mean "overall taste" score of 3.8 at 15 seconds, and 4.2 after 3 minutes. The overall texture was scored as 5.4 at both 15 seconds and 3 minutes, and the overall palatability received a mean score of 4.0 and 4.4 (15 seconds and 3 minutes respectively). The bitterness was scored at a mean of 1.8 at 15 seconds and 2.0 at 3 minutes.

Formulation 5 comprised solely Raspberry flavor (0.8% concentration), and subjects did not score this formulation as high as they did the Formulations that contained a combination of flavors. Specifically, this Formulation was reported to be "very bitter", as it received a mean bitterness score of 1.4 at 15 seconds, although it did improve to a rating of "somewhat bitter" at 3 minutes (mean score was 2.0). Overall, however, these bitterness scores suggest that this formulation was not as successful as the other formulations at masking the bitter aftertaste that is commonly associated with metronidazole. It is also of interest to note that the degree of "liking" the formulation decreased over time. The mean scores provided with respect to texture and overall palatability decreased between the 15 second and 3 minute assessments, although the mean score for taste remained the same between the two time points. Specifically, the mean score for taste was 4.0 at both 15 seconds and 3 minutes respectively, the mean score for texture was 5.6 and 5.2 at the two time points, and overall palatability received a mean score of 4.2 at 15 seconds, and decreased to 3.8 at 3 minutes.

Formulation 6 comprised a high concentration of Raspberry (0.8%) and a medium concentration of peppermint (0.1%). Consistent with the results described above, the mean score for this Formulation was favorable; it produced the highest scores overall, although the differences between the mean scores for it, Formulation 1, and Formulation 3, were marginal. The mean score for overall taste was 6.2 at 15 seconds and 6.4 at 3 minutes; the mean score for texture was 6.4 at both 15 seconds and 3 minutes; the mean score for overall palatability was 6.2 and 6.4 at 15 seconds and 3 minutes respectively, and the degree of bitterness was assessed to be 2.8 at both time points.

Formulation 7 comprised a combination of Strawberry and Raspberry flavors.

Although this Formulation was deemed more palatable than the Formulations that did not contain any flavor, this Formulation did not score as high as the Formulations that contained Peppermint. This Formulation had a mean score of 4.6 and 5.0 for overall taste (15 seconds and 3 minutes respectively). The texture had a mean score of 5.8 at both time points, and the overall palatability was 4.8 at the two time points. The degree of bitterness was assessed as "somewhat bitter" at 5 seconds (mean score was 2.2), although this improved and moved towards "not bitter" at the 3-minute assessment (mean score was 2.8).

To further analyze the results, the formulations tested during this study were examined in greater detail and the key excipients that differed between the formulations analyzed further. From the 7 formulations tested, 4 were chosen to represent the steps taken during the iterative 8-month formulation development to arrive at the most palatable "to be marketed" formulation. For the purposes of this detailed analysis, the following four formulations were examined:

| Formulation Identifier | API | Aluminum magnesium silicate | Flavour | Other |
|---|---|---|---|---|
| 2 | Metronidazole | Magnesium Aluminum Silicate Type 1C (Veegum HV) | Cherry | Methyl Paraben, Propyl Paraben, Sucrose NF, Saccharin Sodium, Sodium Phosphate Monobasic, Sodium Phosphate Dibasic, Microcrystalline Cellulose, Propylene Glycol, Alcohol, Purified Water |
| 5 | Metronidazole | Magnesium Aluminum Silicate Type 1C (Veegum HV) | Raspberry | Methyl Paraben, Propyl Paraben. Sucrose NF, Saccharin Sodium, Sodium Phosphate Monobasic, Sodium Phosphate Dibasic, Microcrystalline Cellulose, Glycerol, Alcohol, Purified Water |
| 4 | Metronidazole | Magnesium Aluminum Silivate Type 1C (Veegum) | No Flavour | Methyl Paraben, Propyl Paraben, Sucrose NF, Sucralose, Sodium Phosphate Monobasic, Sodium Phosphate Dibasic, Microcrystalline Cellulose, Glycerol, Alcohol, Purified Water |
| 1 | Metronidazole | Magnesium Aluminum Silicate Type 1C (Veegum HV) | Raspberry, Strawberry, Peppermint | Methyl Paraben, Propyl Paraben, Sucrose NF, Sucralose, Sodium Phosphate Monobasic, Sodium Phosphate Dibasic, Microcrystalline Cellulose, Glycerol, Alcohol, Purified Water, |

Figure 2:
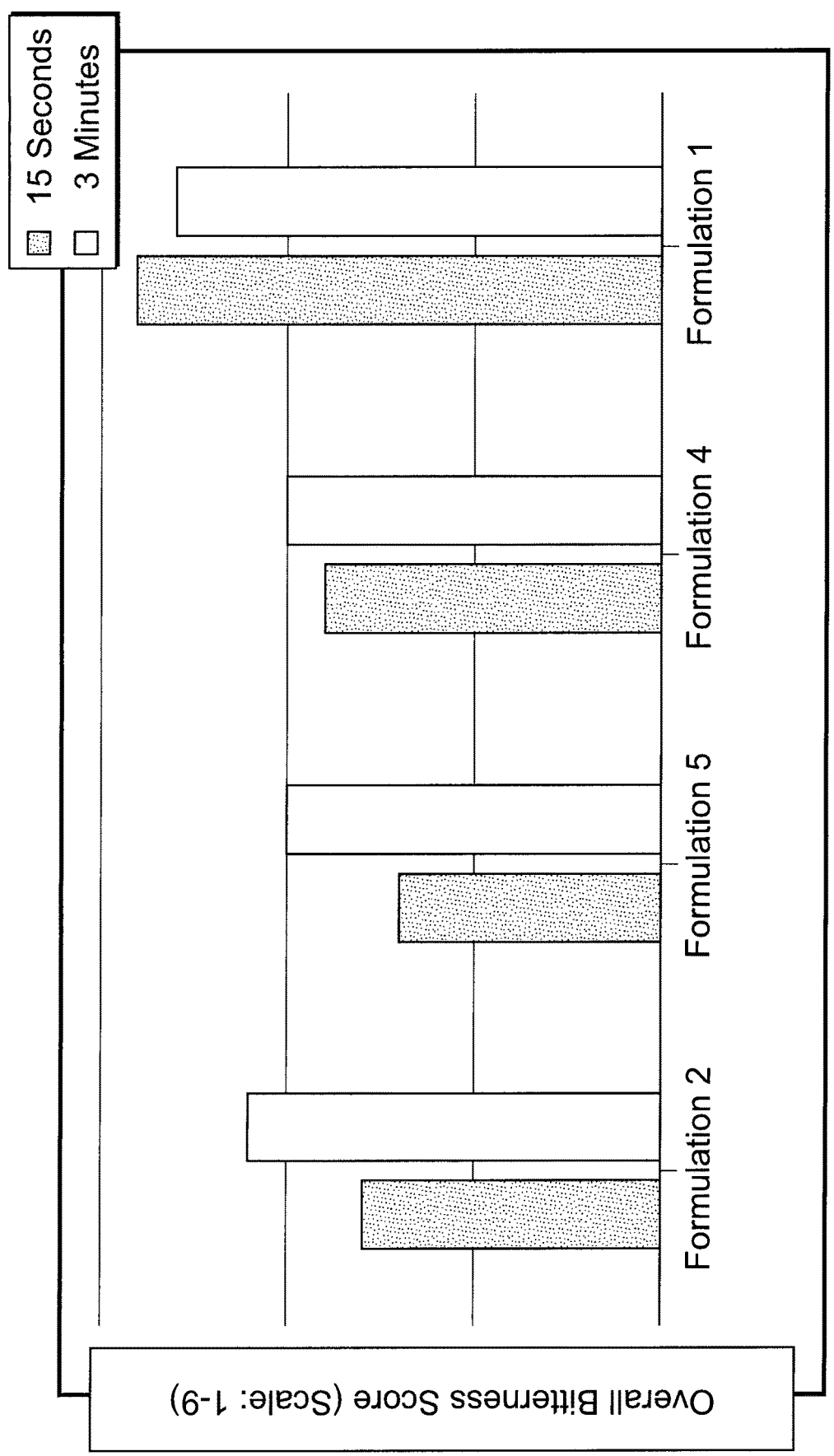
FIG. 2 shows the overall bitterness score of the tested formulations (scored on a scale of 1-9; y axis) at 15 seconds (shaded bar/left bar for the time point; x axis) and 3 minutes (black bar/right bar for the time point; x axis) was directly compared between these four formulations (labeled Formula 2, Formula 5, Formula 4, Formula 1; x axis).

The mean scores for palatability and for bitterness derived from the 5 subjects tested for each of these formulations is shown in FIG. 1 and FIG. 2, respectively. As shown in FIG. 1, when the four formulations were directly compared, Formulation 2 scored the lowest. When overall palatability was scored, this formulation received a mean score of 5.8 at 15 seconds and 6.2 after 3 minutes. Both Formulation 5 and Formulation 4 followed this in the iterative process. Although the overall palatability was improved by replacing propylene glycol with glycerol, and replacement of the cherry flavor with the Raspberry flavor agent to the formulation, the mean score for Formulation 5 was still only 5.2 at 15 seconds and 4.2 at 3 minutes. Formulation 4 had a mean palatability score of 4 at 15 seconds and 4.4 at 3 minutes. This suggested that replacing the saccharin with sucralose improved the palatability from the original formulation, but the removal of flavor agent reduced the palatability overall. The greatest advancement in overall palatability came by combining the flavor agents (strawberry and raspberry) with a third flavor (peppermint). The overall palatability for Formulation 1 scored much higher than the other three formulations; the mean palatability score at 15 seconds was 6.4 and at 3 minutes was 6.0.

As shown in FIG. 2, when the perceived bitterness scores of the four formulations were compared, the data showed the same trend in results. Formulation 2 did not sufficiently mask the bitter after-taste that is commonly associated with metronidazole. The degree of bitterness had a mean score of 1.6 (1=very bitter) at 15 seconds and 2.2 (2=somewhat bitter) at 3 minutes. Although the overall palatability of the formulations appeared to increase with modifications to the excipients, the bitterness score for Formulation 5 did not improve; the mean bitterness score was 1.4 at 15 seconds and 2 at 3 minutes. The mean bitterness score reported for Formulation 4 was comparable to that of Formulation 5; the mean score was 1.8 at 15 seconds and 2 at 3 minutes. The addition of the flavor agents, particularly peppermint, appeared to have the greatest effect on perceived bitterness. The mean bitterness score for Formulation 1 was 2.8 at 15 seconds and 2.6 after 3 minutes (3=not bitter), suggesting that this formulation was superior to the others in masking the bitter after taste.

The results suggest that the formulations of the instant example provide an advantageous and surprising improvement in the overall palatability and the ability to mask the bitter aftertaste associated with metronidazole.

Example 4: Single Dose Comparability Pharmacokinetic Study in Dogs

The instant example evaluates pharmacokinetic parameters in dogs following single dose administration of different formulations of metronidazole. Six male beagle dogs can be administered a single dose of two different oral formulation of metronidazole in a cross-over study design.

The dogs can be divided into two groups for the seven day study. Group 1 can include 3 dogs, and can be orally administered a tablet of metronidazole (i.e., Flagyl) on Day 1. Pharmacokinetic parameters can be obtained at up to 10 time points following administration on Day 1. Thereafter, on Day 7, the Group 1 dogs can be orally administered the metronidazole pharmaceutical compositions of the present disclosure. Pharmacokinetic parameters can be obtained at up to 10 time points following administration on Day 7.

Group 2 can include 3 dogs, and can be orally administered the pharmaceutical compositions of metronidazole of the present disclosure on Day 1. Pharmacokinetic parameters can be obtained at up to 10 time points following administration on Day 1. Thereafter, on Day 7, the Group 2 dogs can be orally administered a tablet of metronidazole (i.e., Flagyl). Pharmacokinetic parameters can be obtained at up to 10 time points following administration on Day 7.

Example 5: Single Dose Taste Test Study in Healthy Volunteers

The instant example provides an investigational, single center, randomized, open label, two period, two treatment, two sequence, crossover, taste test study to assess the palatability of a single 10 mL dose (250 mg/5 mL) of pharmaceutical compositions of metronidazole of the present disclosure relative to a single dose of crushed 500 mg metronidazole (Flagyl®) tablets compounded in a liquid volume of applesauce, in twenty healthy adult male and female subjects (10 per Treatment Sequence group). The palatability of the formulations can be evaluated using the 9-point Hedonic scale.

Twenty (20) adult healthy volunteer subjects can be chosen at random to participate in the study of the instant example. The study can consist of a randomization phase and a two-period treatment phase (with a two-hour washout between each treatment phase):

Sequence A: Subjects randomized to Sequence A can receive pharmaceutical compositions of metronidazole of the present disclosure at 500 mg (10 mL of 250 mg/5 mL) in Taste Test Study Treatment Period 1, followed by crushed metronidazole (Flagyl®) tablets 500 mg (1 tablet) compounded in 10 mL of applesauce in Taste Test Study Treatment Period 2.

Sequence B: Subjects randomized to Sequence B can receive crushed metronidazole (Flagyl®) tablets 500 mg (1 tablet) compounded in 10 mL of applesauce in Taste Test Study Treatment Period 1, followed pharmaceutical compositions of metronidazole of the present disclosure at 500 mg (10 mL of 250 mg/5 mL) in Taste Test Study Treatment Period 2.

After randomization, subjects can undergo two Treatment Periods separated by a washout period (two hours between the two treatment periods). During each treatment period, subjects can receive a single dose of study drug according to the randomized treatment sequence. Palatability of the administered formulations can be assessed using the 9-point hedonic scale (categories: Like extremely, Like very much, Like moderately, Like slightly, Neither like nor dislike, Dislike slightly, Dislike moderately, Dislike very much, Dislike extremely) at 15 seconds and 3 minutes after administration of the dose in each of the three Investigational Study Treatment Periods.

In Taste Test Study Treatment Period 1, subjects randomized to Sequence A can receive a single dose of a pharmaceutical composition of metronidazole of the present disclosure at 500 mg (10 mL of 250 mg/5 mL), and subjects randomized to Sequence B can receive crushed metronidazole (Flagyl®) 500 mg (1 tablet) compounded in applesauce. Dosing can occur at 08:00 hours in the morning of Day 1 (designated as "0 hours"), followed by palatability assessments and safety assessments post-dose. For the palatability assessments, subjects can be asked to evaluate the study drug (crushed metronidazole tablets and the liquid oral suspension) by assessing the degree that they liked/disliked the taste of the study drug, the degree that they liked/disliked the texture of the study drug, and the degree that they liked/disliked the palatability of the study drug overall (taste, texture, smell) at t=15 seconds and t=3 minutes after dosing occurs, using the 9-point hedonic scale. The subjects can also be asked to rate the degree of bitterness of the study drug on a 3-point scale (1=very bitter, 2=somewhat bitter, 3=not bitter) at t=15 seconds and t=3 minutes after dosing occurs. The subjects can also be asked to rate their likelihood of compliance with a dosing regimen of the composition (e.g., 1=unlikely to comply with a dosing regimen, 2=somewhat likely to comply with a dosing regimen, 3=very likely to comply with a dosing regimen).

Taste Test Study Treatment Period 1 can be followed by a washout period of two hours. Subjects can be required to remain at the Phase 1 unit during the washout period.

In Taste Test Study Treatment Period 2, subjects randomized to Sequence A can receive crushed metronidazole (Flagyl®) 500 mg (1 tablet) compounded in 10 mL of applesauce, subjects randomized to Sequence B will receive a single dose of a pharmaceutical composition of metronidazole of the present disclosure at 500 mg (10 mL of 250 mg/5 mL). Dosing can occur at 10:00 hours in the morning of Day 1, followed by palatability assessments and safety assessments post-dose.

Taste Test Study Period 2 can be followed by a washout period of two hours. Subjects can be required to remain at the Phase 1 unit during the washout period.

The responses of all subjects who provided at least one palatability rating (ranked on the 9-point hedonic scale), for at least one formulation, can be analyzed in such a way that each response will be treated as a point on a continuum, to allow descriptive statistics, such as mean, median, range, and standard error of the mean, to be employed to determine the relative palatability of each formulation and how they rate with respect to each other.

Example 6: Single Dose Bioavailability and Palatability Study in Healthy Volunteers The instant example provides a randomized, open label, two treatment, two period, two sequence, crossover, relative bioavailability study to investigate the pharmacokinetics of a single 10 mL dose (250 mg/5 mL) of a pharmaceutical composition of metronidazole of the present disclosure relative to a single dose (500 mg) of metronidazole (Flagyl®) tablets administered under fasting and fed conditions, in 40 healthy adult male and female subjects. The palatability of the pharmaceutical composition of metronidazole of the present disclosure can also be evaluated in a subset of subjects using the 9-point Hedonic scale.

The instant example can consist of screening, two treatment phases (an initial two-period treatment phase under fasting conditions [with a one-week washout in between], a second two-period treatment phase under fed conditions [with a one-week washout in between]), an Investigational Taste Test Study, and a post-treatment follow-up period.

Eligible subjects can be randomized to one of two treatment sequences (Sequence A and Sequence B). After randomization, subjects will undergo two Treatments (Treatment 1 under fasting conditions and Treatment 2 under fed conditions). The two Treatments can be separated by a washout period. Each Treatment can have two periods and each period will also be separated by a washout period (one week between the two dosing days). During each treatment period, subjects can receive a single dose of study drug according to the randomized treatment sequence:

Sequence A: Subjects randomized to Sequence A can receive 500 mg of a metronidazole pharmaceutical composition of the present disclosure (10 mL at 250 mg/5 mL) in Period 1, followed by metronidazole (Flagyl®) 500 mg (1 tablet) in Period 2.

Sequence B: Subjects randomized to Sequence B can receive metronidazole (Flagyl®) 500 mg (1 tablet) in Period 1, followed by 500 mg of a metronidazole pharmaceutical composition of the present disclosure (10 mL at 250 mg/5 mL) in Period 2.

In Treatment 1 (fasting condition), Period 1, eligible subjects can be admitted to the Phase 1 unit between the hours of 19:00 and 21:00 hours on the evening of Day −1 and can remain admitted through the morning of Day 3 (48 hours after dosing). Subjects can be required to fast for at least 10 hours prior to dosing. Subjects randomized to Sequence A can receive a single dose of 500 mg of a metronidazole pharmaceutical composition of the present disclosure (10 mL at 250 mg/5 mL), and subjects randomized to Sequence B can receive a single dose of metronidazole (Flagyl®) 500 mg (1 tablet). Dosing can occur at 08:00 hours in the morning of Day 1 (designated as "0 hours"), followed by safety and PK assessments at set time points over 48 hours post-dose, as detailed in the Schedule of Assessments. Pharmacokinetic sampling can start on Day 1: plasma samples will be taken pre-dose and 0.5, 1, 2, 3, 4, 5, 6, 8, 9, 12, 24, and 48 hours post-dose.

Treatment 1, Period 1 can be followed by a washout (one week between the two dosing days in Treatment 1, Period 1 and Treatment 1, Period 2, which is longer than 5 times the elimination half-life of metronidazole). Subjects are not required to remain at the Phase 1 unit during the washout period.

In Treatment 1 (fasting condition), Period 2, subjects can be admitted to the Phase 1 unit between the evening of Day 7 through the morning of Day 10, (48 hours after dosing). Subjects can be required to fast for at least 10 hours prior to dosing. Subjects randomized to Sequence A can receive a single dose of metronidazole (Flagyl®) 500 mg (1 tablet), and subjects randomized to Sequence B can receive a single dose of 500 mg of a metronidazole pharmaceutical composition of the present disclosure (10 mL at 250 mg/5 mL). Dosing can occur at 08:00 hours in the morning of on Day 8 (designated as "0 hours"), followed by safety and PK assessments at set time points over 48 hours post-dose, as detailed in the Schedule of Assessments. Pharmacokinetic sampling can start on Day 1: plasma samples will be taken pre-dose and 0.5, 1, 2, 3, 4, 5, 6, 8, 9, 12, 24, and 48 hours post-dose.

Treatment 1, Period 2 can be followed by a washout (one week between the two dosing days in Treatment 1, Period 2 and Treatment 2, Period 1, which is longer than 5 times the elimination half-life of metronidazole). Subjects are not required to remain at the Phase 1 unit during the washout period.

In Treatment 2 (fed condition), Period 1, eligible subjects can be admitted to the Phase 1 unit between the hours of 19:00 and 21:00 hours on the evening of Day 14 and can remain admitted through the morning of Day 17 (48 hours after dosing). Subjects can consume a standard meal 30 minutes prior to dosing on the morning of Day 15. Subjects randomized to Sequence A can receive a single dose of 500 mg of a metronidazole pharmaceutical composition of the present disclosure (10 mL at 250 mg/5 mL), and subjects randomized to Sequence B can receive a single dose of metronidazole (Flagyl®) 500 mg (1 tablet). Dosing can occur at 08:00 hours in the morning of Day 15 (designated as "0 hours"), followed by safety and PK assessments at set time points over 48 hours post-dose, as detailed in the Schedule of Assessments. Pharmacokinetic sampling can start on Day 15: plasma samples will be taken pre-dose and 0.5, 1, 2, 3, 4, 5, 6, 8, 9, 12, 24, and 48 hours post-dose.

Treatment 2, Period 1 can be followed by a washout (one week between the two dosing days in Treatment 2, Period 1 and Treatment 2, Period 2, which is longer than 5 times the elimination half-life of metronidazole). Subjects are not required to remain at the Phase 1 unit during the washout period.

In Treatment 2 (fed condition), Period 2, subjects can be admitted to the Phase 1 unit between the evening of Day 21 through the morning of Day 24, (48 hours after dosing). Subjects can consume a standard meal 30 minutes prior to dosing on the morning of Day 21. Subjects randomized to Sequence A can receive a single dose of metronidazole (Flagyl®) 500 mg (1 tablet), and subjects randomized to Sequence B can receive a single dose of 500 mg of a metronidazole pharmaceutical composition of the present disclosure (10 mL at 250 mg/5 mL). Dosing can occur at 08:00 hours in the morning of on Day 22 (designated as "0 hours"), followed by safety and PK assessments at set time points over 48 hours post-dose, as detailed in the Schedule of Assessments. Pharmacokinetic sampling can start on Day 22: plasma samples can be taken pre-dose and 0.5, 1, 2, 3, 4, 5, 6, 8, 9, 12, 24, and 48 hours post-dose.

End of Study Follow-Up: Subjects can return to the clinic six days after the study drug administration in Treatment 2, Period 2 for an end-of-study (EOS) safety follow-up.

Example 7: Safety, and Efficacy Study in Pediatric Subjects with CDI

The instant example provides a study of safety and efficacy parameters of patients with a primary episode or first relapse mild or moderate *C. difficile* infection (CDI) who are administered a metronidazole pharmaceutical composition of the present disclosure. For this example, CDI can be defined as i) ≥3 diarrheal (liquid or unformed) stools/day and a positive *C. difficile* toxin result by enzyme immunoassay (EIA) or cell cytotoxicity assay. Patients must have ≤24 hours of treatment with metronidazole, vancomycin or other antibacterial therapy specific for CDI. Each subject's participation will be approximately 6-7 weeks (≤7 days screening/baseline, 10 days of treatment, and 28±2 days of post-treatment follow-up for safety and recurrence).

The primary objectives of the instant example are to confirm safety of a metronidazole pharmaceutical composition of the present disclosure in pediatric patients with CDI. A secondary objective can be to confirm the efficacy of a metronidazole pharmaceutical composition of the present disclosure to metronidazole (Flagyl®) in the treatment of primary episode or first relapse mild or moderate CDI.

The primary endpoint of the instant example can be the frequency of treatment-emergent adverse events (TEAEs), treatment-related adverse events (AEs), serious adverse events (SAEs), and withdrawals due to AEs.

Secondary endpoints of the instant example can include one or more of i) Clinical cure rate (defined as a marked reduction in the number of unformed bowel movements, [frequency of unformed stools of 3 or fewer for two consecutive days], resolution of abdominal discomfort [with maintenance of resolution for the duration of the 10-day treatment period], and no further requirement for CDI therapy as of the end of treatment [EOT; as assessed the day after the last dose of study drug]); ii) Total relief of symptoms of CDI (defined for example as resolution to ≤3 bowel movements per day (whether solid, semi-formed, or liquid as recorded on the patient diary) without other associated signs or symptoms, such as fever (≥37.7° C.), abdominal pain, and elevated WBC by day 10 of the study); iii) Time to resolution of diarrhea (time to ≤2 semi-formed or formed stools/day and maintained until Day 10; based on patient daily diary); iv) Global cure (defined as the resolution of diarrhea without recurrence during the 28-day post-treatment follow-up period); and v) Recurrence rate (defined as ≥3 unformed (loose or watery) stools and a positive stool result for *C. difficile* toxin A or B) within the 28-day post-treatment follow-up period vi) palatability of the metronidazole pharmaceutical composition of the present disclosure.

Example 8: Randomized, Open-Label, Single Dose, Two Sequence, Crossover, Relative Bioavailability and Taste Test Study of ATI-1501 in Healthy Adult Volunteers 1. List of Abbreviations and Overall Study Design and Plan: Description List of Abbreviations and Definition of Terms AE Adverse event
AUC Area under the plasma concentration-time curve
$AUC_{0-inf}$ Area under the plasma concentration-time curve from time zero to infinity
$AUC_{0-t}$ Area under the plasma concentration-time curve from time zero to last quantifiable concentration
BMI Body mass index
CI Confidence interval
$CL_{total}/F$ Apparent total body clearance
$C_{max}$ Maximum plasma concentration
CRU Clinical research unit
ECG Electrocardiogram
FSH Follicle-stimulating hormone
HIV Human immunodeficiency virus
IRB Institutional Review Board
ITT Intention-to-treat
MedDRA Medical Dictionary for Regulatory Activities
NF National Formulary
PK Pharmacokinetic(s)
$Q_1$ First quartile
$Q_3$ Third quartile
SAE Serious adverse event
SD Standard deviation
SOC System organ class
SOP Standard operating procedure
TEAE Treatment-emergent adverse event
$T_{max}$ Time to maximum plasma concentration
$T_{1/2}$ Terminal half-life
US United States
USP United States Pharmacopeia
$V_d/F$ Apparent volume of distribution
WBC White blood cell
λz Terminal elimination rate constant This was a Phase 1, single-center, randomized, open-label, single dose, 2-sequence, 2-treatment, crossover, relative bioavailability study of ATI-1501 under fasted and fed conditions in healthy adult subjects. The study evaluated the relative bioavailability of 500 mg ATI-1501 oral suspension (10 mL of ATI-1501 at 250 mg metronidazole/5 mL concentration) against the reference listed drug, a 500 mg metronidazole tablet (Flagyl®). Approximately 20 consenting subjects were planned to be randomized into each of the 2 treatment sequences, for a total of 40 subjects required for evaluation and study completion. Subjects randomized to treatment sequence 1 received a single dose of ATI-1501 during treatment period 1 and treatment period 3, and a single dose of Flagyl® during treatment period 2 and treatment period 4. Subjects randomized to treatment sequence 2 received a single dose of Flagyl® during treatment period 1 and treatment period 3, and a single dose of ATI-1501 during treatment period 2 and treatment period 4. In both treatment sequences, the first 2 treatments were administered under fasted condition, and the third and fourth treatments were administered under fed conditions (after a high-fat, high-calorie meal). There was a 7-day washout period between each dosing during the Treatment phase of the study. Subjects were admitted into the clinical research unit (CRU) the day prior to dosing and remained in the CRU until 48 hours post-dose. Safety and PK assessments were conducted over 48 hours post-dosing during each treatment period.

Following completion of the main study, approximately 20 randomly selected subjects were planned to be enrolled in the Taste Test sub-study to evaluate the palatability of ATI-1501 against a single 500 mg tablet of Flagyl® crushed in up to 30 mL of apple sauce. Subjects enrolled in the Taste Test sub-study were to receive, in a random order (based on the treatment sequence they were randomized into), a single dose of ATI-1501 and a single dose of Flagyl®, separated by a 2-hour washout period. They were asked to assess the palatability of the study drugs by rating how much they liked or disliked the taste, texture, and smell of the drug using a 9-point Hedonic scale and a 3-point scale to evaluate the degree of bitterness. Subjects were discharged 2 hours after the last study drug administration during the Taste Test sub-study.

Figure 5:
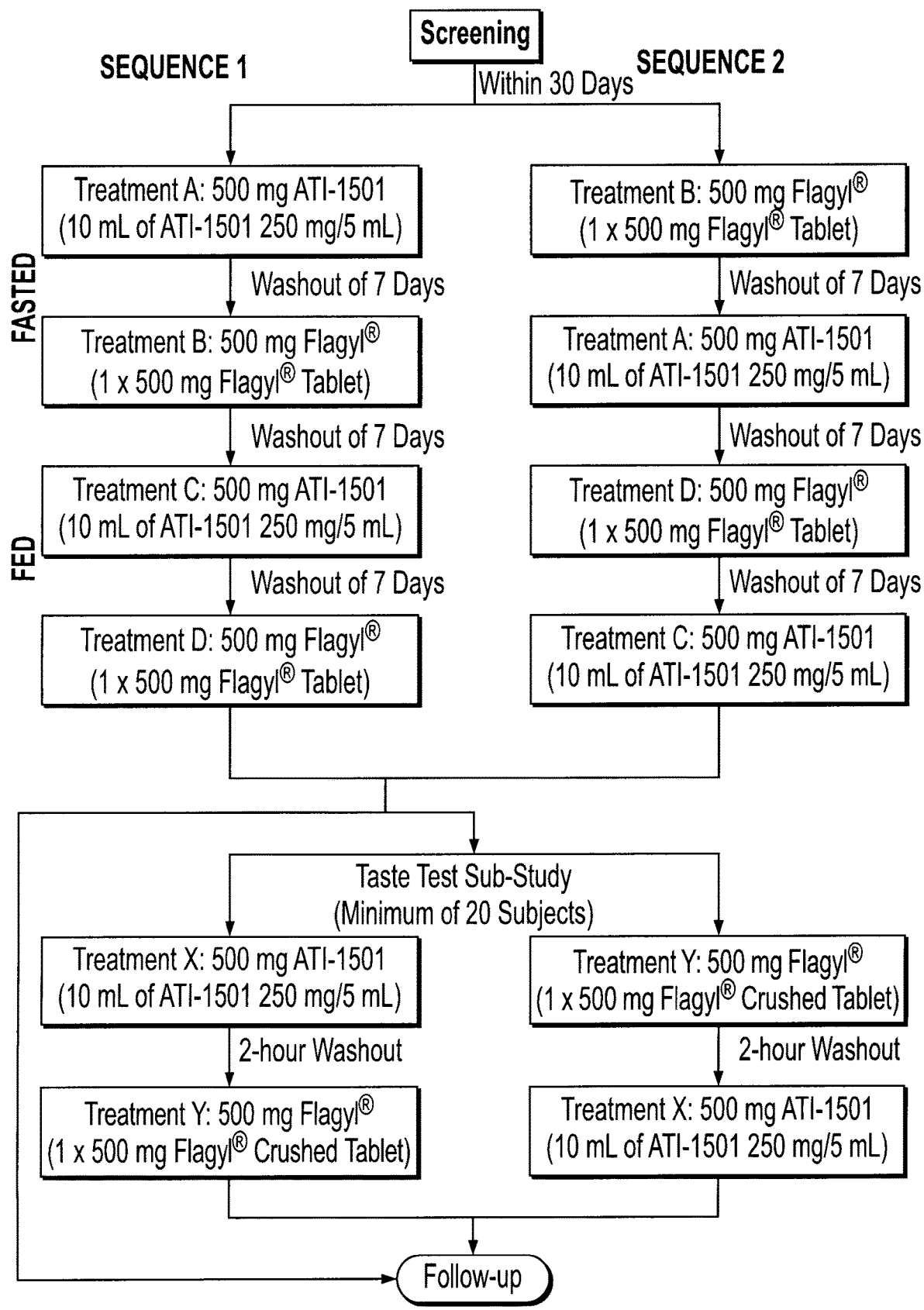
FIG. 5 is a schematic of study design for a Phase 1, randomized, open-label, single dose, two sequence, crossover, relative bioavailability and taste test study of ATI-1501 in healthy adult volunteers.

Further details on the study design are provided below. The overall study design is summarized in FIG. 5.

1.1 Screening Phase

Subjects who provided informed consent underwent a standard medical screen to determine eligibility for the study. Within 30 days of screening, subjects who successfully completed the Screening phase returned to the CRU as inpatients for the Treatment phase of the study.

1.2 Treatment Phase

Eligible subjects were randomized to either treatment sequence 1 or sequence 2 to determine the order in which they received the study drugs. The study drugs and doses were as follows:

Treatment A: 10 mL of ATI-1501 oral suspension at 250 mg metronidazole/5 mL concentration
Treatment B: single 500 mg Flagyl® tablet Treatment C: 10 mL of ATI-1501 oral suspension at 250 mg metronidazole/5 mL concentration Treatment D: single 500 mg Flagyl® tablet The sequence groups for the fasted condition were:

Sequence 1: Treatment A followed by Treatment B (A B)

Sequence 2: Treatment B followed by Treatment A (B A)

The sequence groups for the fed condition were:

Sequence 1: Treatment C followed by Treatment D (C D)

Sequence 2: Treatment D followed by Treatment C (D C)

Subjects were admitted into the CRU a day prior to dosing and remained in the CRU until 48 hours post-dose. Dosing took place in the morning; safety and PK assessments were conducted over 48 hours post-dosing during each treatment period. All subjects underwent a 7-day washout period following each dosing.

1.2.1 Taste Test Sub-Study

The Taste Test sub-study evaluated the palatability of ATI-1501 oral suspension against a single 500 mg tablet of Flagyl® crushed in up to 30 mL of apple sauce. The Flagyl® tablet was crushed in apple sauce. Briefly, the 500 mg metronidazole tablet was crushed with a glass pestle for 30 seconds to break intact tablet into lumps. The broken tablet was ground in the mortar with a glass pestle by applying consistent pressure in a circular motion with the pestle for 2 minutes. The material was examined for appearance prior to the transfer of crushed powders onto a small pharmacy wax paper. The powder was added to a measuring cup containing the 30 mL pre-measured applesauce while mixing with an appropriate sized clean spatula. The admixture was gently mixed for approximately 30 seconds to ensure the powder was well blended. Twenty-five subjects who completed the main study were planned to be randomly chosen to participate in the sub-study and were randomized to 1 of 2 treatment sequences.

The study drugs and doses were as follows:

Treatment X: 10 mL of ATI-1501 oral suspension at 250 mg metronidazole/5 mL concentration Treatment Y: single 500 mg Flagyl® tablet crushed in up to 30 mL of apple sauce The randomized treatment sequences for the Taste Test sub-study were as follows:

Sequence 1: Treatment X followed by Treatment Y (X Y)

Sequence 2: Treatment Y followed by Treatment X (Y X)

Each subject underwent 2 Taste Test periods, separated by a 2-hour washout period during which subjects remained in the CRU. Subjects were to receive their respective dose on the morning of Day 24 (ie, day of discharge of the last treatment period of the main study). Once subjects consumed their respective drugs, they were asked to assess the palatability of the study drug by rating how much they liked or disliked the taste, texture, and smell of the drug using a 9-point Hedonic scale and a 3-point scale to evaluate the degree of bitterness. After Taste Test period 2, subjects provided their overall preference by selecting the study drug they preferred the most, and rated how much they preferred the treatment they selected. The assessment of palatability and overall preference was completed following each study drug administration.

Subjects remained in the CRU for 2 hours post-dose after the last study drug administration for safety assessments and discharged thereafter. Subjects were monitored throughout the treatment periods for adverse events (AEs).

1.3 Follow-up Phase

Subjects returned to the CRU 6 days after the last dose of study drug administration for a Follow-up visit to assess safety and determine if any AEs had occurred since their last study visit. Subjects were also asked to complete the Follow-up visit procedures in the event of early discontinuation.

2. Discussion of Study Design

The purpose of the main study was to determine the relative bioavailability of ATI-1501 oral suspension compared to Flagyl®. The purpose of the Taste Test sub-study was to assess the palatability of ATI-1501 against Flagyl® tablets crushed in up to 30 mL of apple sauce using a 9-point Hedonic scale and a 3-point bitterness scale. The main study also aimed to evaluate the safety and characterize the PK profile of ATI-1501 oral suspension in healthy adults. The PK of ATI-1501 oral suspension in a population of subjects with no concomitant illnesses was recorded and analyzed. Blood samples were collected at pre-described time intervals throughout the study to determine the bioavailability of ATI-1501 oral suspension and characterize its overall PK profile. Subjects were randomized to 1 of 2 treatment sequences and each group of subjects underwent 4 periods of treatment. Each subject received each treatment regimen in a crossover study design and served as his or her own control. The crossover design was best suited for this study because it removed any bias associated with the order in which the 2 study drugs were administered. The study drugs were administered under fasted and fed conditions to evaluate the effects of food on the absorption of metronidazole, administered in the form of ATI-1501 oral suspension. The washout period lasted 7 days to ensure that the drug had left the system before another dosing took place.

The Taste Test sub-study was rigorously designed to compare the palatability of ATI-1501 and Flagyl® that had been crushed in apple sauce. Preparation and presentation of both formulations were standardized. The Flagyl® tablet was crushed in up to 30 mL of apple sauce. The most widely used scale for measuring food acceptability (the 9-point Hedonic scale) (Lim 2011) was used to rate the taste, texture, and smell, and a 3-point scale was used to evaluate the degree of bitterness of the 2 study drugs. Consideration was given to include an adequate washout period between administrations of each of the study drugs; the 2-hour time period between the administrations of the 2 study drugs was included to allow sufficient time for the removal of the metronidazole from taste receptors, while still retaining subject engagement in the study. Assessments of palatability were made at 15 seconds and 3 minutes post-dose to capture both the initial taste and after-taste.

3. Study Population

Healthy male and female subjects 18 to 65 years of age, inclusive, were selected to participate in this study. Subjects were recruited at one center in Canada (INC Research Toronto, Inc.) Subjects were selected to participate in the study based on satisfying pre-set inclusion and exclusion criteria. Subjects who voluntarily withdrew consent or were discontinued from the study prior to completion were considered as withdrawn from the study.

4. Treatments 4.1 Treatments Administered

In this study, the term "study drug" was used to describe the investigational product (ATI-1501) and the reference product (Flagyl® tablet).

Both study drugs were administered orally under fasted and fed conditions. The order of study drug administration under each condition was dictated by the treatment sequence the subject was randomized into as detailed in Table 2.

Each single dose of ATI-1501 oral suspension (250 mg metronidazole/5 mL) contained 10 mL of the investigational product, delivering 500 mg of metronidazole. Each single dose of the reference drug contained one 500 mg Flagyl® tablet.

TABLE 2

| | Fasted | | Fed | |
|---|---|---|---|---|
| Sequence | Treatment Period 1 | Treatment Period 2 | Treatment Period 3 | Treatment Period 4 |
| 1 | A<br>10 mL of ATI-1501<br>at 250 mg/5 mL | B<br>1 × 500 mg<br>Flagyl ® tablet | C<br>10 mL of ATI-1501<br>at 250 mg/5 mL | D<br>1 × 500 mg<br>Flagyl ® tablet |
| 2 | B<br>1 × 500 mg<br>Flagyl ® tablet | A<br>10 mL of ATI-1501<br>at 250 mg/5 mL | D<br>1 × 500 mg<br>Flagyl ® tablet | C<br>10 mL of ATI-1501<br>at 250 mg/5 mL |

Subjects were given tepid water to drink with consumption of the study drugs. Additional water was provided if required to complete dosing. Subjects were not permitted to break or chew the Flagyl® tablets and were expected to swallow the tablets whole.

4.1.1 Taste-Test Sub-Study

During the Taste Test sub-study, subjects received ATI-1501 and Flagyl®. The order of administration was dictated by the randomized treatment sequence as described in Table 3.

TABLE 3

Dosing Regimen for Taste Test Sub-Study

| Sequence | Taste Test Period 1 | Taste Test Period 2 |
|---|---|---|
| 1 | X<br>10 mL of ATI-1501 at 250 mg/5 mL | Y<br>1 × 500 mg Flagyl ® crushed tablet<br>in apple sauce |
| 2 | Y<br>1 × 500 mg Flagyl ® crushed tablet<br>in apple sauce | X<br>10 mL of ATI-1501 at 250 mg/5 mL |

Subjects were given tepid water to drink after the 3-minute post-dose palatability and taste assessments were completed.

4.2 Identity of Study Drugs

ATI-1501 is a metronidazole oral suspension, containing 250 mg metronidazole/5 mL. ATI-1501 has the chemical name: Metronidazole, 2-methyl-5-nitro-1H-imidazole-1-ethanol. The chemical structure of ATI-1501 is:

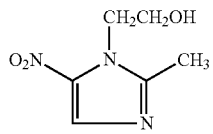

The molecular formula of ATI-1501 is: $C_6H_9N_3O_3$; and its molecular weight is 171.15 grams (g)/mol.

4.2.1 ATI-1501 Composition

ATI-1501 is an oral suspension formulation of metronidazole at 250 milligrams (mg)/5 milliliters (mL) (50 mg/mL). It contains ten non-medicinal substances including: sucrose, glycerin, purified water, Veegum® (magnesium aluminum silicate), microcrystalline cellulose, sucralose, sodium phosphate (monobasic/dibasic), and preservatives (methyl paraben, propyl paraben). It also contains two flavoring agents (strawberry and peppermint). Table 4 provides the CAS #, Function, and Percentage of each excipient contained within the ATI-1501 formulation.

TABLE 4

| ATI-1501 (Metronidazole Oral Suspension) Excipients | | | |
|---|---|---|---|
| Component | CAS# | Function | Percentage (%)<br>w/v |
| Sucrose NF | 57-50-1 | Sweetening Agent | 50.000 |
| Glycerin USP (Synthetic) | 56-81-5 | Solvent | 10.000 |
| Purified Water USP | 7732-18-5 | Solvent | QS |
| Magnesium Aluminum Silicate Type 1C (VEEGUM ® HV) | Mixture of:<br>Smectite clay (<99%): 12199-37-0<br>And<br>Quartz (0.8%): 14808-60-7 | Suspending Agents | 1.200 |

TABLE 4-continued

ATI-1501 (Metronidazole Oral Suspension) Excipients

| Component | CAS# | Function | Percentage (%) w/v |
|---|---|---|---|
| Microcrystalline Cellulose NF (Avicel PH-101) | 9004-34-6 | Texture Modifier | 0.600 |
| Kidazzle ™ Strawberry | | Flavor | 0.400 |
| Sucralose NF | 56038-13-2 | Sweetening Agent | 0.250 |
| Natural Peppermint Flavour Wonf | | Flavor | 0.200 |
| Sodium Phosphate Monobasic | 7558-80-7 | Buffer | 0.200 |
| Sodium Phosphate Dibasic | 7558-79-4 | Buffer | 0.200 |
| Methyl Paraben | 99-76-3 | Preservative | 0.150 |
| Propyl Paraben | 94-12-3 | Preservative | 0.020 |

Abbreviations:
CAS = chemical abstracts service;
NF = National Formulary;
kg = kilogram;
L = liter;
USP = United States Pharmacopeia
Stability and Storage Recommendations:
ATI-1501 is to be stored between 2-25° C., and protected from direct sunlight.

4.4 Selection of Doses in the Study

Consistent with the current standards for evaluating relative bioavailability, a single dose of ATI-1501 oral suspension was compared with the maximum recommended single dose of Flagyl®. The 500 mg single dose was consistent with the dosing recommendations for currently approved oral metronidazole products, including Flagyl® in adults, which is 7.5 mg/kg every 6 hours or approximately 500 mg every 6 hours for a 70 kg adult (DailyMed—Metronidazole). This dose level has also been tested and proven safe in animals and humans.

The same doses of ATI-1501 oral suspension and Flagyl® were utilized in the Taste Test sub-study; however, Flagyl® was crushed in up to 30 mL of apple sauce.

4.5 Selection and Timing of Dose

Subjects were randomly assigned to treatment sequence 1 or sequence 2, which dictated the order in which they received the study drugs under both fasted and fed conditions. Dosing was to occur on the morning of Day 1 for treatment period 1, on the morning of Day 8 for treatment period 2, on the morning of Day 15 for treatment period 3, and on the morning of Day 22 for treatment period 4. Attempts were made to maintain each subject's dosing time between treatment days. Due to reasons explained in further detail below, the washout period following dosing during treatment period 1 was extended by 7 days, therefore, the dosing days for treatment periods 2 to 4 did not fall on Days 8, 15, or 22. The treatment period 2 Day 8 visit occurred on study Day 15, the treatment period 3 Day 15 visit occurred on study Day 22, and the treatment period 4 Day 22 visit occurred on study Day 29. For treatment periods that required study drug administration under fed conditions, subjects were required to abstain from food for at least 10 hours after which they started the test meal. Within 30 minutes of completing the test meal, the study drug was administered. No other food was allowed for at least 4 hours post-dosing. Water was allowed ad libitum except for approximately 1 hour prior to dosing and for approximately 1 hour post-dosing.

4.5.1 Dietary and Other Restrictions

Aside from the inclusion and exclusion criteria, each subject had to agree to abide by certain specified restrictions for the specified time, such restrictions included:

Subjects were required to abstain from alcohol for 2 weeks prior to screening and throughout the study.

Subjects were required to abstain from recreational drug use throughout the study, from screening until the end of the Follow-up visit.

Fasted Conditions: Subjects were required to fast (abstain from food and liquids) for at least 10 hours prior to dosing and for at least 4 hours post-dosing. Water was permitted ad libitum except for approximately 1 hour prior to dosing and for approximately 1 hour post-dosing.

Fed Conditions: Subjects were required to fast (abstain from food and liquids) for at least 8 hours after which they started the test meal 30 minutes prior to the administration of the study drug. Subjects were expected to completely consume their respective meal before dosing. No other food was allowed for at least 4 hours post-dose. Water was allowed as desired except for approximately 1 hour prior to dosing and for approximately 1 hour post-dosing.

The high-fat (approximately 50% of total caloric content of the meal) and high-calorie (approximately 800 to 1000 kilocalories) meal derived approximately 150 kilocalories from protein, 250 kilocalories from carbohydrates, and 500 to 600 kilocalories from fat. An example test meal consisted of 2 eggs fried in butter, 2 strips of bacon, 2 slices of toast with butter, 120 g of hash browns, and 240 mL of whole milk.

4.6 Blinding

This was an open-label study. Since knowledge of the treatment allocations would not have an effect on the primary outcomes measures (ie, PK), no concealment of the treatment allocations was necessary.

4.7 Prior and Concomitant Therapy

Subjects were required to avoid using certain specified medications from the specified time points and throughout the study unless, in the opinion of the investigator or designee, the product would not interfere with the study procedure or data integrity, or compromise the safety of the subject.

Concomitant medications were prohibited in this study unless prescribed by the investigator to treat clinical events or exempted by the investigator on a case-by-case basis because they would be unlikely to affect the study results or subject safety.

5. Safety and Pharmacokinetic Variables 5.1 Safety and Pharmacokinetic Measurements Assessed The safety variables assessed, the laboratory tests conducted, and the PK blood sampling time points throughout the study are summarized in Table 5. Efficacy was not evaluated in this study.

TABLE 5

Schedule of Assessments

| | Screening | Treatment Period: | | | | | | | | | | | | | | | | | Follow-up |
|---|---|---|---|---|---|---|---|---|---|---|---|---|---|---|---|---|---|---|---|
| Study Procedure: | | | | | | | | | | | | | | | | | | | |
| Visit: | — | 1 | | | | 2 | | | | 3 | | | | 4 | | | | | — |
| Day: | 1 | 2 | | | | 3 | | | | 4 | | | | 5 | | | | | 6 |
| | −30 to −2 | −1 | 1 | 2 | 3 | 7 | 8 | 9 | 10 | 14 | 15 | 16 | 17 | 21 | 22 | 23 | 24 | | 28/30 |
| Subject Review | | | | | | | | | | | | | | | | | | | |
| Informed Consent | X | | | | | | | | | | | | | | | | | | |
| Medical History | X | X[a] | | | | X[a] | | | | X[a] | | | | X[a] | | | | | X[a] |
| Medication History | X | | | | | | | | | | | | | | | | | | |
| Inclusion/Exclusion Criteria[b] | X | X | | | | X | | | | X | | | | X | | | | | |
| Study Restrictions Review | | X | | | | X | | | | X | | | | X | | | | | X |
| Demographics | X | | | | | | | | | | | | | | | | | | |
| Safety | | | | | | | | | | | | | | | | | | | |
| Physical Examination[c] | X | X | | | | X | | | | X | | | | X | | | | | X |
| Height, Weight, BMI[d] | X | X | | | | X | | | | X | | | | X | | | | | X |
| Serum Pregnancy | X | | | | | | | | | | | | | | | | | | X |
| Urine Pregnancy[e] | | X | | | | X | | | | X | | | | X | | | | | |
| FSH (post-menopausal women) | | | | | | | | | | | | | | | | | | | |
| HIV, Hepatitis A, Hepatitis B, Hepatitis C and TB tests | X | | | | | | | | | | | | | | | | | | |
| Vital Signs[f] | X | X | X | | | | X | | | | X | | | | X | | | | X |
| Electrocardiogram[g] | X | X | X | | | | X | | | | X | | | | X | | | | X |
| Urine Drug Screen | X | X | | | | X | | | | X | | | | X | | | | | X |
| Breath Alcohol | X | X | | | | X | | | | X | | | | X | | | | | X |
| Urine Cotinine | X | X | | | | X | | | | X | | | | X | | | | | |

[a]The focus was on any changes since the last visit.
[b]Inclusion/exclusion criteria were assessed at each admission for ongoing eligibility review.
[c]Symptom-directed physical examinations were performed at the investigator's discretion during each treatment visit. A full physical examination was performed at Screening and Follow-up.
[d]Height was measured at screening, but it was not measured upon admission into the clinic during each treatment period.
[e]Positive urine pregnancy tests were confirmed by serum pregnancy tests.
[f]Vital signs included blood pressure, pulse rate, respiratory rate, and oral temperature. Vital signs were measured pre-dose and approximately 90 minutes post-dose in each treatment period.
[g]ECGs were performed after 5 minutes of resting. ECGs were taken approximately 90 minutes post-dose in each treatment period.

| | Screening | Treatment Period: | | | | | | | | | | | | | | | | | Follow-up |
|---|---|---|---|---|---|---|---|---|---|---|---|---|---|---|---|---|---|---|---|
| Study Procedure: | | | | | | | | | | | | | | | | | | | |
| Visit: | — | 1 | | | | 2 | | | | 3 | | | | 4 | | | | | — |
| Day: | 1 | 2 | | | | 3 | | | | 4 | | | | 5 | | | | | 6 |
| | −30 to −2 | −1 | 1 | 2 | 3 | 7 | 8 | 9 | 10 | 14 | 15 | 16 | 17 | 21 | 22 | 23 | 24 | | 28/30 |
| Clinical Laboratory Tests | X | X[a] | X | | | | X | | | | X | | | | X | | | | X |
| Concomitant Medications | | X | | | | ← Recorded throughout → | | | | | | | | | | | | | X |
| Adverse Event Monitoring | X | X | | | | ← Recorded throughout → | | | | | | | | | | | | | X |
| Taste Test Sub-Study | | | | | | | | | | | | | | | | | | | |
| 9-Point Hedonic Scale and 3-Point Scale | | | | | | | | | | | | | | | | | | X[b] | |
| Pharmacokinetics | | | | | | | | | | | | | | | | | | | |
| Blood Sampling[c] | | | X | X | | | X | X | | | X | X | | | X | X | | | |

TABLE 5-continued

Schedule of Assessments

| Study Administration | | | | | | | |
|---|---|---|---|---|---|---|---|
| Admission | | X | X | X | X | | |
| Drug Administration | X | | X | X | X | X | X[d] |
| Discharge | | | X | X | X | X | X |

BMI = body mass index, FSH = follicle-stimulating hormone, HIV = human immunodeficiency virus, TB = tuberculosis

[a]Screening safety laboratory tests which were performed within 3 days prior to dosing did not have to be repeated at pre-dose on Day −1. Safety laboratory testing was performed at approximately 120 minutes post-dose.

[b]The scales were administered at 15 seconds and 3 minutes post-dose. The two scales were completed simultaneously or one after the other.

[c]PK samples were taken at pre-dose, 0.5, 1, 2, 3, 4, 5, 6, 8, 9, 12, 24, and 48 hours post-dose. Acceptable windows of PK sampling were approximately 5 minutes at each time point between 1 and 12 hours post-dose and approximately 10 minutes at 24 hours post-dose.

[d]Study drug was only administered to the 25 subjects who were randomized into the Taste Test sub-study.

5.2 Pharmacokinetic Variables and Drug Concentration Measurements

The PK variables included the following:
- maximum observed plasma concentration ($C_{max}$)
- time to maximum plasma concentration ($T_{max}$)
- area under the plasma concentration-time curve from time zero to last quantifiable concentration ($AUC_{0-t}$)
- area under the plasma concentration-time curve from time zero to infinity ($AUC_{0-inf}$)
- terminal elimination half-life ($T_{1/2}$)
- volume of distribution ($V_d/F$)
- total body clearance ($CL_{total}/F$)

Venous blood samples were collected to determine the plasma concentrations of ATI-1501. A high-fat meal was administered prior to dosing during the fed condition and food was withheld for at least 10 hours prior to dosing during the fasting condition to observe the effects of food on the PK of ATI-1501. In each treatment period, venous blood samples were collected by venipuncture or optional indwelling catheter at pre-dose, 0.5, 1, 2, 3, 4, 5, 6, 8, 9, 12, 24, and 48 hours post-dose. Samples were collected, processed, and shipped according to the site's SOPs and instructions from the sponsor and/or bioanalytical laboratory.

5.3 Safety Variables

The safety variables included the following:
- Incidence, frequency, and severity of AEs, either self-reported or solicited by non-directive questioning of the subject
- Vital signs (blood pressure, respiratory rate, pulse rate, and oral temperature)
- ECG parameters and abnormalities
- Clinical laboratory test results (clinical chemistry, hematology, urinalysis)
- Physical examination findings 5.4 Palatability Variables The palatability of ATI-1501 and Flagyl® was assessed using a universally recognized 9-point Hedonic scale (Lim 20111 to assess the taste, texture, and smell of the 2 study drugs. The scale included the following categories: Dislike Extremely (1), Dislike very Much (2), Dislike Moderately (3), Dislike Slightly (4), Neither Like nor Dislike (5), Like Slightly (6), Like Moderately (7), Like Very Much (8), and Like Extremely (9).

A 3-point scale was used to evaluate the degree of bitterness of the 2 study drugs. The scale included the following categories: Very Bitter (1), Bitter (2), and Not Bitter (3).

7. Statistical Methods and Determination of Sample Size 7.5 Analysis of Pharmacokinetics The following PK parameters for metronidazole were assessed under both fasting and fed conditions using WinNonlin™:

$C_{max}$, $T_{max}$, $AUC_{0-t}$, $AUC_{0-inf}$, $V_d/F$, and $CL_{total}/F$.

$C_{max}$ was determined by visual inspection of the observed concentration-vs-time curve for each subject. AUC was calculated using the trapezoidal rule with extrapolation to infinity. The plasma $T_{1/2}$ of metronidazole was calculated using the data points up to 48 hours after dosing. Log-linear regression of the terminal slope was used to estimate the elimination rate constant ($\lambda_z$).

$AUC_{0-inf}$ was calculated as follows: $AUC_{0-inf} = AUC_{0-t} + Ca$, where Ct is the last measurable drug concentration and $\lambda_z$ is the terminal or elimination rate constant calculated according to an appropriate method. $CL_{total}$ was calculated by dividing the dose with the AUC for the given dosing interval.

Pharmacokinetic parameters were evaluated at pre-specified, set time points over 48 hours following a single oral dose of either product under fasting and fed conditions, as described above.

Pharmacokinetic parameters were presented with means, SD, median, and range (minimum, maximum) values and in subject listings.

The relative bioavailability of metronidazole from ATI-1501 compared to Flagyl® was evaluated using standard bioequivalence approach involving ANOVA and 90% confidence intervals (CIs) for primary PK parameters $C_{max}$, $AUC_{0-t}$, and $AUC_{0-inf}$.

7.6 Analysis of Taste Test Measures

Analyses were performed for the Taste Test in the Sub-Study Population.

Individual by-time point data and paired differences of ATI-1501 vs Flagyl® for taste, texture, smell (from 9-point Hedonic Scale) and degree of bitterness (from 3-point scale) were listed with descriptive statistics. Median, first quartile ($Q_1$), third quartile ($Q_3$), and the P value of the paired difference from the sign test were presented. Box plots of taste, texture, smell, and degree of bitterness by treatment were also provided.

The 9-point Hedonic scale is a balanced bipolar scale around neutral at the center with 4 positive and 4 negative categories on each side. The categories are labeled with phrases representing various degrees of affect and those labels are arranged successively to suggest a single continuum of likes and dislikes. The descriptors were intended not only to help subjects respond accordingly, but also help experimenters interpret the mean value of responses in terms of degree of liking or disliking. The scale is the most widely recognized and used scale to measure taste preference and selection in the food industry (Lim 2011; Lawless 2010).

Subjects were asked to rate the taste, texture, and smell of the 2 study drugs using a 9-point Hedonic scale with the following categories: 1=Dislike Extremely, 2=Dislike Very Much, 3=Dislike Moderately, 4=Dislike Slightly, 5=Neither Like nor Dislike, 6=Like Slightly, 7=Like Moderately, 8=Like Very Much, and 9=Like Extremely.

An abbreviated 3-point scale was used to rate the degree of bitterness of the 2 study drugs. The 3-point scale had the following categories: 1=Very Bitter, 2=Somewhat Bitter, and 3=Not Bitter.

For the Overall Preference, subjects were asked if they preferred the liquid form of study drug (ATI-1501) or the crushed study drug tablet in apple sauce (Flagyl® tablet). Based on the indicated preferred study drug form, subjects rated their preferences using the following 5-point scale: 1=Very much prefer the liquid form over the crushed tablet in applesauce, 2=Slightly prefer the liquid form over the crushed tablet in apple sauce, 3=No preference, 4=Slightly prefer the crushed tablet in apple sauce over the liquid form, 5=Very much prefer the crushed tablet in apple sauce over the liquid form.

7.7 Determination of Sample Size

The sample size was selected without performing a power calculation to provide descriptive information on the bioavailability, safety, and tolerability following oral administration of ATI-1501. The sample size of 40 completers for the main study was chosen to obtain reasonable evidence of safety without exposing an undue number of subjects to the investigational product during this Phase 1 study.

A minimum of 20 subjects were randomized to the Taste Test sub-study. The sample size selected for the sub-study was consistent with recent studies evaluating the palatability of various oral pharmaceutical products in randomized crossover studies (Bai (2017); Bastiaans (2017)).

8 Study Subjects 8.1 Disposition of Subjects

A total of 93 subjects were screened for inclusion in the study. Of these, 67 subjects were considered eligible to proceed to the Treatment phase of the study and 26 subjects were deemed ineligible. The most common reason for ineligibility at screening was having clinically significant laboratory values and/or out-of-range vital signs (46%, 12 of the 26 subjects). Although 67 subjects were considered eligible at screening, only 48 subjects were randomized and treated in the study based on their screening number.

A total of 48 subjects were randomly assigned to 1 of the 2 treatment sequences in the main study. All 48 subjects completed the first treatment period (fasted condition) of the study. Of the 48 subjects, a total of 46 subjects completed 3 treatment periods (2 under fasted condition and 1 under fed condition). Of the 46 subjects, a total of 44 subjects completed all 4 treatment periods (2 under fasted condition and 2 under fed condition).

Of the 44 subjects who completed the main study, 25 subjects were randomized to 1 of the 2 treatment sequences and completed the Taste Test sub-study.

8.2 Data Sets Analyzed

All 48 subjects randomized in the main study were included in the Randomized/ITT Population, Safety Population, and PK Population.

All 25 subjects randomized to the sub-study comprised the Sub-Study Population.

8.3 Demographics and Other Baseline Characteristics

Table 6 summarizes the demographic characteristics at baseline for the main study and sub-study. Most subjects in the Randomized/ITT, Safety, and PK Populations were male (72.9%), white (62.5%), and not Hispanic or Latino (79.2%). Mean age was 42.6 years (range 18-63 years), and mean BMI was 25.39 kg/m2 (range 20.2-29.6 kg/m2).

Most subjects in the Sub-Study Population were male (72%), white (72%), and not Hispanic or Latino (64%). Mean age was 43.4 years (range 18-63 years), and mean BMI was 25.33 kg/m$^2$ (range 20.5-29.6 kg/m$^2$).

TABLE 6

Subject Demographics and Selected Baseline Characteristics - Randomized, Safety, Pharmacokinetic, and Sub-Study Populations

| Characteristic | Randomized/ITT, Safety, and PK Populations (N = 48) | Sub-Study (Taste Test) Population (N = 25) |
|---|---|---|
| Age (years) | | |
| Mean (SD) | 42.6 (10.56) | 43.4 (11.32) |
| Range | 18 to 63 | 18 to 63 |
| Age Group, n (%) | | |
| 18-30 | 6 (12.5) | 3 (12) |
| 31-50 | 31 (64.6) | 15 (60) |
| 51-65 | 11 (22.9) | 7 (28) |
| Gender, n (%) | | |
| Male | 35 (72.9) | 18 (72.0) |
| Female | 13 (27.1) | 7 (28.0) |
| Females of child-bearing potential | 10 (20.8) | 5 (20.0) |
| Race, n (%) | | |
| White | 30 (62.5) | 18 (72.0) |
| Black or African American | 11 (22.9) | 4 (16.0) |
| Asian | 4 (8.3) | 0 |
| Other | 3 (6.3) | 3 (12.0) |
| Ethnicity, n (%) | | |
| Not Hispanic or Latino | 38 (79.2) | 16 (64.0) |
| Hispanic or Latino | 10 (20.8) | 9 (36.0) |
| Height (cm) | | |
| Mean (SD) | 170.29 (8.758) | 169.46 (7.691) |
| Range | 151.9 to 188.2 | 157.0 to 185.0 |
| Weight (kg) | | |
| Mean (SD) | 73.87 (11.114) | 72.86 (9.687) |
| Range | 50.8 to 101.0 | 51.9 to 94.1 |
| BMI (kg/m$^2$) | | |
| Mean (SD) | 25.39 (2.716) | 25.33 (2.630) |
| Range | 20.2 to 29.6 | 20.5 to 29.6 |

BMI = body mass index;
ITT = intention-to-treat;
n or N = number of subjects;
PK = pharmacokinetics;
SD = standard deviation
Percentages were calculated based on the number of subjects in the respective population as the denominator.

Baseline medical history data consisted of immune system disorders; infections and infestations; surgical and medical procedures; injury, poisoning, and procedural complication; eye disorders; pregnancy, puerperium, and perinatal conditions; skin and subcutaneous tissue disorders; respiratory, thoracic and mediastinal disorders; and blood and lymphatic system disorders.

Prior and concomitant medications were reported for a total of 16 subjects. The most common concomitant medication was paracetamol that was administered to 10 subjects for the treatment of TEAEs (mainly headaches).

9. Pharmacokinetic, Palatability, and Treatment Preference Assessments 9.1 Pharmacokinetic Results
Pharmacokinetic Results Metronidazole Plasma Concentrations—ATI-1501 vs Flagyl®

Figure 6A:
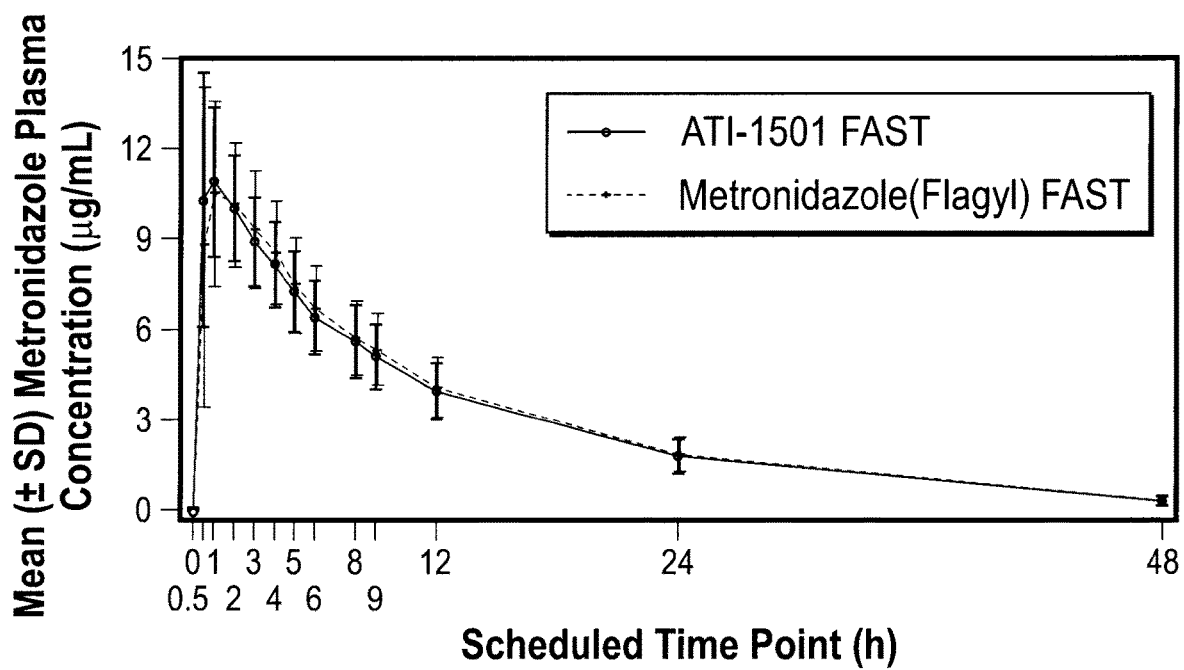
FIG. 6A is a graph of the mean (±standard deviation) concentration-time profile of metronidazole following ATI-1501 (solid line) and Flagyl® (dotted line) treatment under fasted conditions, for the Pharmacokinetic (PK) Population on a linear scale.
Figure 6B:
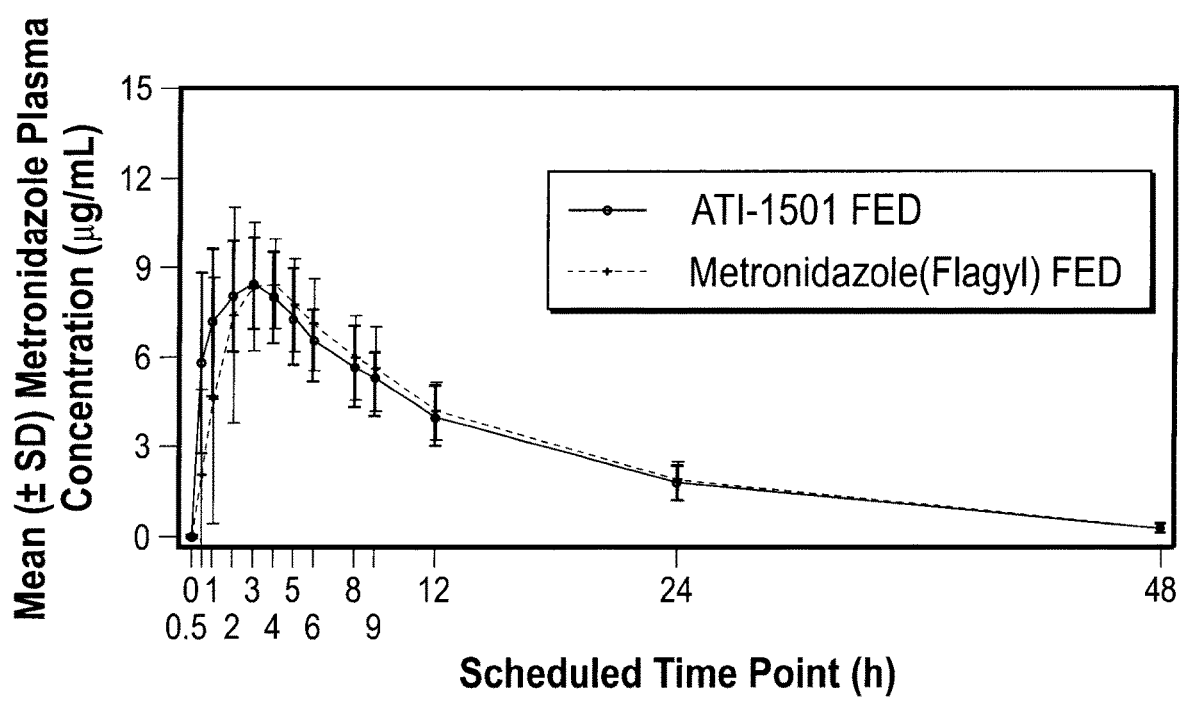
FIG. 6B is a graph of the mean (±standard deviation) concentration-time profile of metronidazole following ATI-1501 (solid line) and Flagyl® (dotted line) treatment under fed conditions, for the Pharmacokinetic (PK) Population on a linear scale.

Mean concentration-time profiles of metronidazole following ATI-1501 and Flagyl® treatments under fasted and fed conditions are presented graphically for the PK Population on linear scales in FIGS. 6A and 6B. Mean plasma concentrations of metronidazole increased rapidly following oral administration of ATI-1501 and Flagyl® with a peak observed around 1 hour post-dose for both treatments under fasted condition, while the maximum mean concentration under fed condition appeared to be delayed at 2 hours post-dose for ATI-1501 and at 3 hours post-dose for Flagyl®. Mean plasma metronidazole concentrations were comparable for ATI-1501 and Flagyl® under both fasted and fed conditions. After reaching the maximum, mean plasma metronidazole concentrations declined at similar rates for both ATI-1501 and Flagyl® under both fasted and fed conditions.

Metronidazole Plasma Concentrations—ATI-1501 Under Fasted and Fed Conditions

Figure 7A:
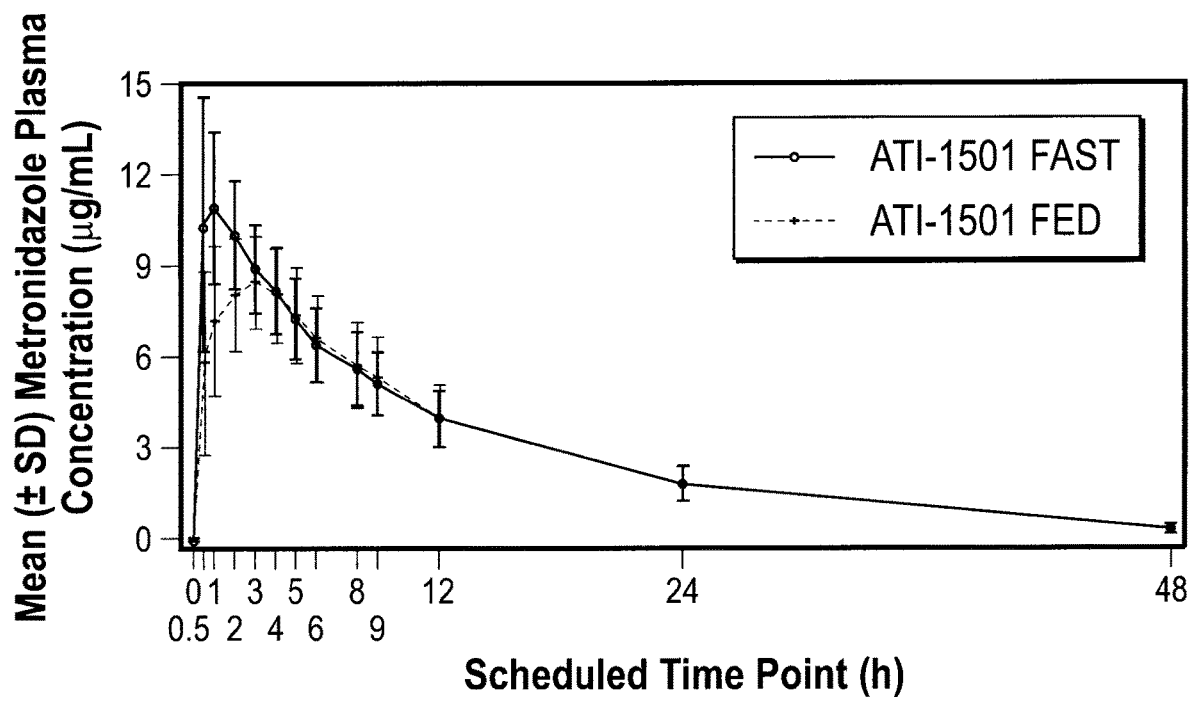
FIG. 7A is a graph of the mean (±standard deviation) concentration-time profile of metronidazole following ATI-1501 administration under fasted (solid line) and fed (dotted line) conditions for the PK Population on a linear scale.
Figure 7B:
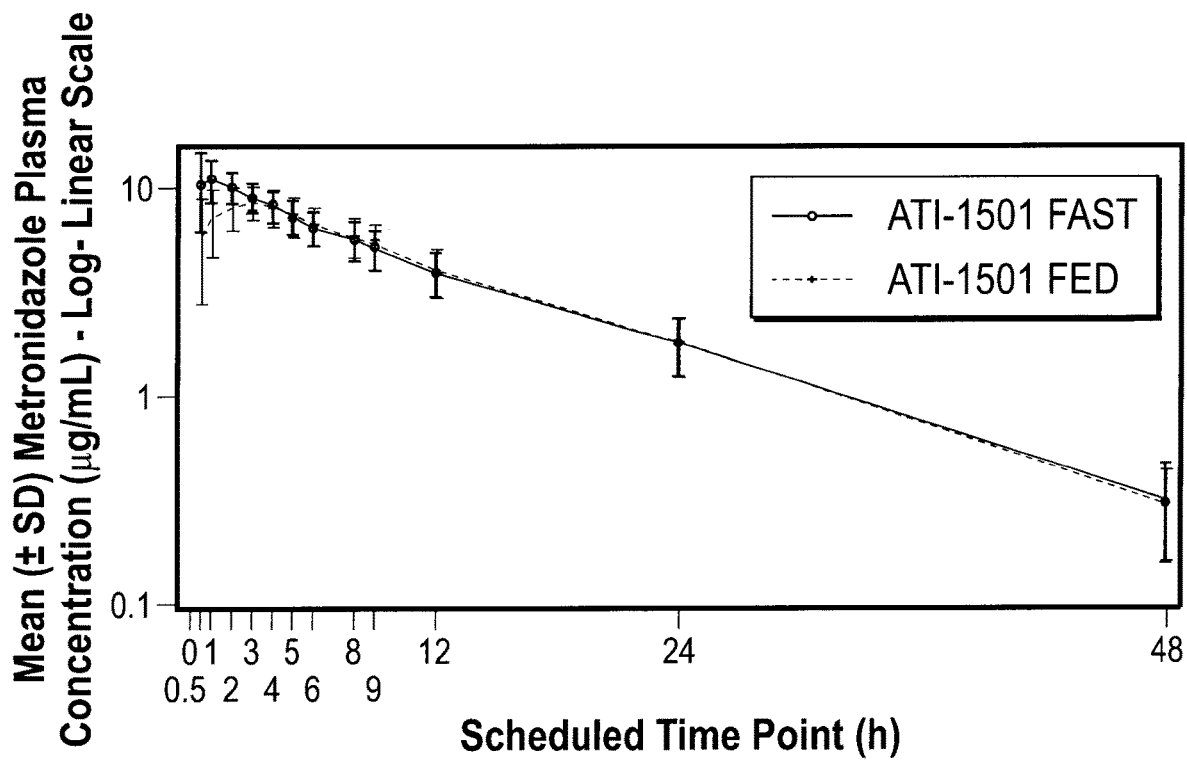
FIG. 7B is a graph of the mean (±standard deviation) concentration-time profile of metronidazole following ATI-1501 administration under fasted (solid line) and fed (dotted line) conditions for the PK Population on a log-linear scale.

Mean concentration-time profiles of metronidazole following ATI-1501 administration under fasted and fed conditions are presented graphically for the PK Population on linear and log-linear scales in FIGS. 7A and 7B. Following ATI-1501 administration, mean peak plasma metronidazole concentrations were higher ($C_{max}$ of approximately 11 μg/mL) and were achieved sooner (at approximately 1 hour post-dose) under fasted condition compared to fed condition ($C_{max}$ of approximately 8 μg/mL was reached at 3 hours post-dose). After reaching the maximum, mean plasma metronidazole concentrations declined at similar rates under fasted and fed conditions, and remained detectable in all subjects at 24 hours post-dose and in majority of subjects at 48 hours post-dose.

Metronidazole Pharmacokinetic Parameters—ATI-1501 and Flagyl® Under Fasted and Fed Conditions Mean PK parameters including $C_{max}$, $AUC_{0-t}$, $AUC_{0-inf}$, $T_{max}$, and other parameters ($\lambda z$, $T_{1/2}$, $V_d/F$, and $CL_{total}/F$) of metronidazole following oral administration of 500 mg ATI-1501 suspension or Flagyl® tablet under both fasted and fed conditions were summarized for the PK Population. As shown in Table 7, the geometric mean $C_{max}$ values for metronidazole were higher under fasted conditions (12.45 μg/mL for ATI-1501 and 12.00 μg/mL for Flagyl®) compared to fed conditions (9.172 μg/mL for ATI-1501 and 9.749 μg/mL for Flagyl®), with no apparent differences between the 2 study drugs. The geometric mean $AUC_{0-t}$ and $AUC_{0-inf}$ values were also slightly higher under fasted conditions (131.6 h*μg/mL and 136.0 h*μg/mL, respectively for ATI-1501; and 134.1 h*μg/mL and 138.6 h*μg/mL, respectively for Flagyl®) compared to the values obtained under fed conditions (124.1 h*μg/mL and 128.1 h*μg/mL, respectively for ATI-1501; 124.9 h*μg/mL and 129.5 h*μg/mL, respectively for Flagyl®). Median $T_{max}$ was 1 hour after administration of both study drugs under fasted conditions, whereas $C_{max}$ was delayed under fed conditions (median $T_{max}$ was 2 hours for ATI-1501 and 3 hours for Flagyl®).

TABLE 7

Pharmacokinetic Parameters for Metronidazole (PK Population)

| Parameter | Summary Statistics | ATI-1501 Fasted | Flagyl ® Fasted | ATI-1501 Fed | Flagyl ® Fed |
|---|---|---|---|---|---|
| $C_{max}$ (μg/mL) | n | 46 | 48 | 45 | 45 |
| | Mean (SD) | 12.66 (2.3250) | 12.33 (2.8958) | 9.289 (1.4856) | 9.940 (1.9974) |
| | CV % | 18.4 | 23.5 | 16.0 | 20.1 |
| | Median | 12.60 | 12.29 | 9.294 | 9.692 |
| | Range | 8.56, 17.8 | 7.43, 21.4 | 6.46, 12.2 | 6.52, 14.4 |
| | GeoMean (GeoCV %) | 12.45 (18.7) | 12.00 (23.6) | 9.172 (16.3) | 9.749 (20.1) |
| $AUC_{0-t}$ (h*μg/mL) | n | 46 | 48 | 45 | 45 |
| | Mean (SD) | 134.6 (28.379) | 137.4 (30.277) | 127.2 (28.927) | 128.1 (29.330) |
| | CV % | 21.1 | 22.0 | 22.7 | 22.9 |
| | Median | 134.5 | 130.6 | 118.6 | 123.3 |
| | Range | 80.4, 188 | 86.2, 195 | 85.9, 189 | 80.5, 1 table |
| | GeoMean (GeoCV %) | 131.6 (22.1) | 134.1 (22.4) | 124.1 (22.7) | 124.9 (23.1) |
| $AUC_{0-inf}$ (h*μg/mL) | n | 46 | 48 | 45 | 45 |
| | Mean (SD) | 139.3 (30.160) | 142.0 (31.898) | 131.4 (30.470) | 133.0 (31.152) |
| | CV % | 21.7 | 22.5 | 23.2 | 23.4 |
| | Median | 137.9 | 134.4 | 123.1 | 131.8 |
| | Range | 87.6, 202 | 87.3, 206 | 86.9, 197 | 81.3, 211 |
| | GeoMean (GeoCV %) | 136.0 (22.5) | 138.6 (22.7) | 128.1 (23.1) | 129.5 (23.6) |
| $T_{max}$ (h) | n | 46 | 48 | 45 | 45 |
| | Median | 1.000 | 1.000 | 2.017 | 3.000 |
| | Range | 0.500, 2.00 | 0.500, 4.00 | 0.500, 4.00 | 0.500, 5.00 |

$AUC_{0-inf}$ = area under the plasma concentration-time curve from zero to infinity,
$AUC_{0-t}$ = area under the plasma concentration-time curve from zero to the last measurable concentration,
$C_{max}$ = maximum plasma concentration,
CV = coefficient of variation,
Geo = geometric,
n = number of subjects with data,
PK = pharmacokinetic,
SD = standard deviation,
$T_{max}$ = time to maximum plasma concentration Metronidazole Pharmacokinetic Parameters—Comparison of Metronidazole Pharmacokinetic Parameters Between ATI-1501 and Flagyl®

Statistical evaluation of $C_{max}$, $AUC_{0-t}$, and $AUC_{0-inf}$ for metronidazole was performed using an ANOVA mixed-effects model with treatment, period, and treatment sequences as fixed effects and subject nested within sequence as a random effect. The results of the treatment comparisons between ATI-1501 and Flagyl® are summarized in Table 8.

TABLE 8

Treatment Comparison of Pharmacokinetics for Metronidazole - ANOVA Model

| Parameter | LS Mean Difference (SE) | F | P Value | Geo Mean Ratio (Investigational/Reference) (%) | 90% CI (Lower, Upper) |
|---|---|---|---|---|---|
| Fasted Condition | | | | | |
| $C_{max}$ (ng/mL) | 0.031 (0.0332) | 0.89 | 0.351 | 103.180 | 97.580, 109.102 |
| $AUC_{0-t}$ (h*ng/mL) | −0.024 (0.0169) | 2.00 | 0.165 | 97.645 | 94.918, 100.451 |
| $AUC_{0-inf}$ (h*ng/mL) | −0.024 (0.0169) | 1.95 | 0.170 | 97.675 | 94.946, 100.481 |
| Fed Condition | | | | | |
| $C_{max}$ (ng/mL) | −0.059 (0.0270) | 4.74 | 0.035 | 94.285 | 90.095, 98.669 |
| $AUC_{0-t}$ (h*ng/mL) | −0.009 (0.0136) | 0.44 | 0.513 | 99.104 | 96.856, 101.403 |
| $AUC_{0-inf}$ (h*ng/mL) | −0.010 (0.0138) | 0.50 | 0.484 | 99.030 | 96.757, 101.356 |

$AUC_{0-inf}$ = area under the plasma concentration-time curve from zero to infinity,
$AUC_{0-t}$ = area under the plasma concentration-time curve from zero to the last measurable concentration,
CI = confidence interval,
$C_{max}$ = maximum plasma concentration,
Geo = geometric,
LS = least square,
SE = standard error The mean $C_{max}$, $AUC_{0-t}$ and $AUC_{0-inf}$ for metronidazole were not statistically different (P>0.05) for ATI-1501 (investigational product) compared to Flagyl® (reference product) regardless of whether the treatment was administered under fasted or fed conditions, except for $C_{max}$ under fed condition, which was lower following ATI-1501 compared to Flagyl® administration (P=0.035). The geometric mean ratios of $C_{max}$, $AUC_{0-t}$, and $AUC_{0-inf}$ for the investigational vs reference treatments were all close to 100% (between 94.285% and 103.180%) under both fasted and fed conditions. The 90% CIs of geometric mean ratios for $C_{max}$, $AUC_{0-t}$, and $AUC_{0-inf}$ were all within the standard limits of 80% to 125% for demonstrating bioequivalence. These results demonstrated that 500 mg ATI-1501 oral suspension is bioequivalent to 500 mg Flagyl® oral tablet when administered under fasted and fed conditions.

Metronidazole Pharmacokinetic Parameters—Evaluation of Food Effect on the Pharmacokinetics of ATI-1501

To evaluate the effects of food intake on the PK of ATI-1501, $C_{max}$, $AUC_{0-t}$, and $AUC_{0-inf}$ values for metronidazole were compared between fasted and fed conditions using an ANOVA mixed-effects model with treatment, period, and treatment sequences as fixed effects and subject nested within sequence as a random effect. The results of these comparisons are summarized in Table 9.

TABLE 9

Food Effect on the Absorption of Orally Administered ATI-1501 - ANOVA Model

| | LS Mean Difference (SE) | F | P Value | Geo Mean Ratio (Fed/Fasted) (%) | 90% CI (Lower, Upper) |
|---|---|---|---|---|---|
| $C_{max}$ (μg/mL) | −0.305 (0.0303) | 101.09 | <0.0001 | 73.722 | 70.062, 77.574 |
| $AUC_{0-t}$ (h*μg/mL) | −0.055 (0.0141) | 15.45 | <0.001 | 94.622 | 92.412, 96.884 |
| $AUC_{0-inf}$ (h*μg/mL) | −0.056 (0.0146) | 15.05 | <0.001 | 94.507 | 92.223, 96.848 |

$AUC_{0-inf}$ = area under the plasma concentration-time curve from zero to infinity,
$AUC_{0-t}$ = area under the plasma concentration-time curve from zero to the last measurable concentration,
CI = confidence interval,
$C_{max}$ = maximum plasma concentration,
Geo = geometric,
LS = least square,
SE = standard error For the analyses presented in this table, ATI-1501 administered under fasted conditions served as reference for ATI-1501 administered under fed conditions.

The mean $C_{max}$, $AUC_{0-t}$ and $AUC_{0-inf}$ for metronidazole were lower after ATI-1501 was administered under fed compared to fasted conditions (P<0.001 for all comparisons). The geometric mean ratios of $C_{max}$, $AUC_{0-t}$, and $AUC_{0-inf}$ for the fed vs fasted conditions were 73.722, 94.622, and 94.507, respectively. The 90% CI of geometric mean ratios for $AUC_{0-t}$ (92.412%, 96.884%) and $AUC_{0-inf}$ (92.223%, 96.848%) were within the bioequivalence limits of 80% to 125%. However, the 90% CI of geometric mean ratio for $C_{max}$ (70.062%, 77.574%) was outside the standard bioequivalence limits of 80% to 125%, indicating that a complete absence of food effect on the bioavailability of metronidazole following ATI-1501 administration was not established.

Median differences in $T_{max}$ for metronidazole following ATI-1501 administration were compared between the fed and fasted conditions using the Hodges-Lehmann estimation, with the P value for the median obtained from the Wilcoxon sign-rank test on the within-subject differences. The results of these comparisons are summarized in Table 10. The $T_{max}$ for metronidazole following ATI-1501 administration was statistically significantly longer under fed compared to fasted conditions (median difference 1.250 hours, 90% CI: 1.00, 1.509; P<0.0001), indicating a significant delay in reaching the maximum plasma concentration when ATI-1501 was administered with food. Individual subject $T_{max}$ comparisons using paired t tests for ATI-1501 showed similar results, with P<0.0001 and mean difference of 1.281 hours (90% CI: 0.9627, 1.599).

TABLE 10

Non-Parametric Comparison of $T_{max}$ for ATI-1501

|  | Fed Conditions (N = 45) | Fasted Condition (N = 45) |
|---|---|---|
| Median $T_{max}$ | 2.017 | 1.000 |
| Median Difference[a] | | 1.250 |
| 90% CI | | 1.000, 1.509 |
| P Value[b] | | <0.0001 |

CI = confidence interval,
$T_{max}$ = time to maximum observed plasma concentration
[a]Hodges-Lehmann estimated median difference between treatments
[b]P value for the median was obtained from the Wilcoxon sign-rank test on the within-subject differences; significant difference was defined a priori as P < 0.05.

Metronidazole Pharmacokinetic Parameters—Pharmacokinetic Conclusions

Pharmacokinetic conclusions include:

The geometric mean ratios for metronidazole $C_{max}$, $AUC_{0-t}$, and $AUC_{0-inf}$ between ATI-1501 and Flagyl® were between 94.3% and 103.2%, and the 90% CIs were within the standard bioequivalence limits of 80% to 125% under both fasted and fed conditions. Moreover, the geometric mean ratios for the comparison of extent of metronidazole exposure (AUCs) between ATI-1501 and Flagyl® were close to 100% under both fasted and fed conditions. These results demonstrated that 500 mg ATI-1501 administered as an oral suspension was bioequivalent to 500 mg Flagyl® oral tablet under both fasted and fed conditions.

Following ATI-1501 administration, mean peak plasma metronidazole concentrations were higher ($C_{max}$ of approximately 11 μg/mL) and occurred sooner (at approximately 1 hour post-dose) under fasted condition compared to fed condition ($C_{max}$ of approximately 8 μg/mL was reached at 3 hours post-dose).

The mean $C_{max}$, $AUC_{0-t}$, and $AUC_{0-inf}$ of metronidazole were lower after ATI-1501 was administered after a meal compared to fasted conditions (P<0.001 for all comparisons); the magnitude of the differences was approximately 26.3%, 5.4%, and 5.5%, respectively. The 90% CIs of the geometric mean ratios were well within the bioequivalence limits of 80% to 125% for $AUC_{0-t}$ and $AUC_{0-inf}$, but not for $C_{max}$ (70.1%, 77.6%), indicating that a complete absence of food effect on the bioavailability of metronidazole following ATI-1501 administration was not established.

9.2 Taste Test Sub-Study Results

The Taste Test sub-study was designed to evaluate the palatability of ATI-1501 relative to crushed metronidazole in apple sauce. Subjects received ATI-1501 and crushed metronidazole in apple sauce in a randomized order and were asked a series of questions to assess palatability and treatment preference. To assess palatability, subjects were asked to score the taste, texture, and smell of each drug product on a 9-point Hedonic scale, a scale that is widely used in the determination of taste preference and palatability. On the 9-point scale, higher values were associated with greater subject preference: 1=Dislike Extremely, 2=Dislike Very Much, 3=Dislike Moderately, 4=Dislike Slightly, 5=Neither Like nor Dislike, 6=Like Slightly, 7=Like Moderately, 8=Like Very Much, 9=Like Extremely. A score of 5 was neutral. The bitterness of ATI-1501 and crushed metronidazole in apple sauce were also directly measured on a 3-point scale given the known bitter taste profile of the drug. A higher bitterness score was associated with a less bitter taste. The 3-point scale had the following categories: 1=Very Bitter, 2=Somewhat Bitter, 3=Not Bitter.

Taste Test Sub-Study Results—Palatability

Figure 8A:
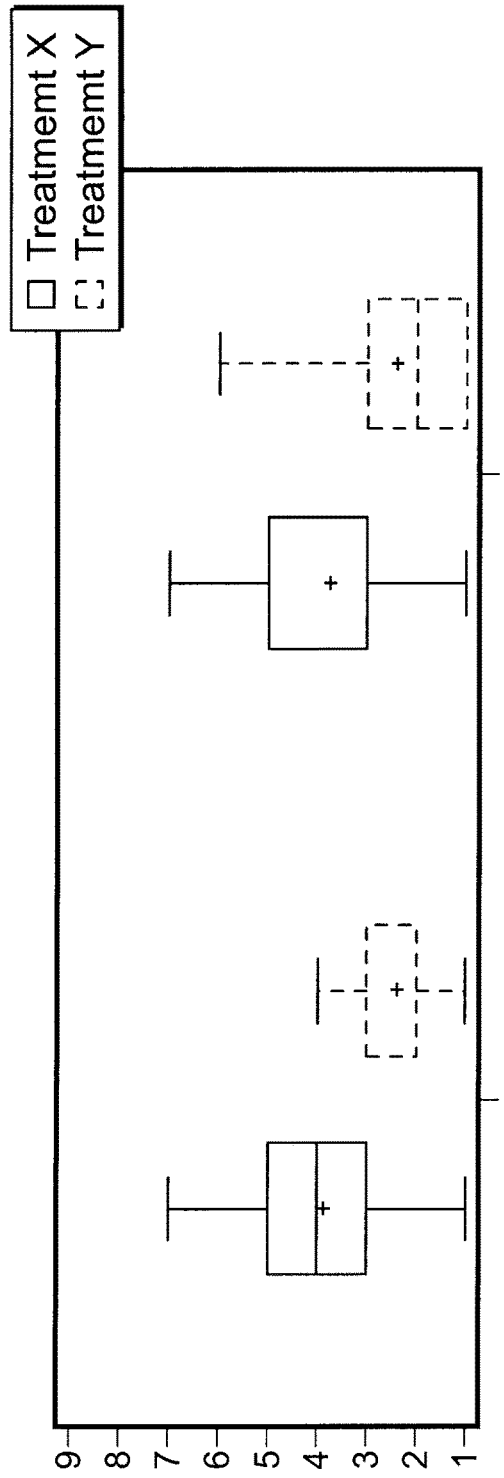
FIG. 8A is graph of the mean (±standard deviation) Hedonic scale scores for taste at 15 seconds and 3 minutes post-dose of ATI-1501 (Treatment X; solid lines/left data for each time point) or Flagyl® (Treatment Y; dotted lines/right data for each time point). Treatment X=10 mL of ATI-1501 oral suspension at 250 mg metronidazole/5 mL; Treatment Y=500 mg Flagyl® tablet crushed in up to 30 mL of apple sauce.
Figure 8B:
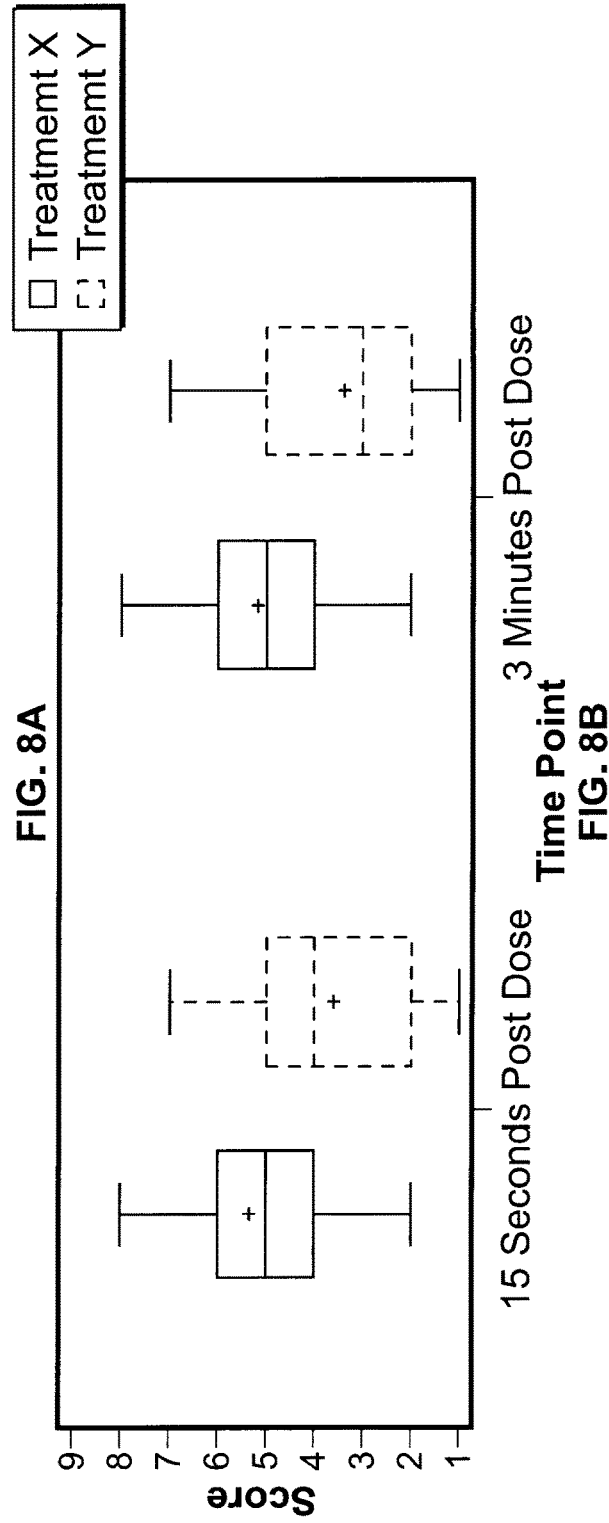
FIG. 8B is graph of the mean (±standard deviation) Hedonic scale scores for texture at 15 seconds and 3 minutes post-dose of ATI-1501 (Treatment X; solid lines/left data for each time point) or Flagyl® (Treatment Y; dotted lines/right data for each time point). Treatment X=10 mL of ATI-1501 oral suspension at 250 mg metronidazole/5 mL; Treatment Y=500 mg Flagyl® tablet crushed in up to 30 mL of apple sauce.

ATI-1501 consistently scored better than crushed metronidazole in apple sauce across all palatability metrics with notable, statistically significant improvements in both taste and bitterness scores (FIGS. 8A-8C and summary statistics and analyses in Table 11 and Table 12). At 15 seconds after dosing, the mean ATI-1501 taste score was 1.5 units higher than crushed metronidazole in apple sauce (3.9 vs 2.4), indicative of a shift towards a more neutral taste profile (FIG. 8A, Table 11). Non-parametric analyses confirmed the shift to be strongly statistically significant (P<0.0001) (Table 12). At the same time point, bitterness scores with ATI-1501 were significantly improved over crushed metronidazole in apple sauce (P<0.001) (Table 12) with a mean score improvement of 0.7 (2.0 vs 1.3) (FIG. 8D, Table 11). Taste and bitterness scores at 3 minutes after dosing were similar to those recorded at 15 seconds.

Scores of texture and smell were also improved with ATI-1501 relative to crushed metronidazole in apple sauce. At 15 seconds post-dose, the mean ATI-1501 texture score was 1.8 units higher than with crushed metronidazole in apple sauce (5.4 vs 3.6) (FIG. 8B, Table 11). Similarly, the mean smell score for ATI-1501 was higher than with crushed metronidazole in apple sauce by 0.7 units (4.8 vs 4.1) (FIG. 8C, Table 12). Differences in smell and texture scores were both shown to be statistically significant by non-parametric analyses (P<0.05) and provided additional evidence of palatability improvements with the ATI-1501 formulation (Table 12). Similar scores were reported at the 3-minute time point.

TABLE 11

Summary of 9-Point Hedonic Scale and
3-Point Scale Values by Time Point

| Time Point | Statistic | Taste | Texture | Smell | Bitterness |
|---|---|---|---|---|---|
| ATI-1501 | | | | | |
| 15 seconds | Mean (SD) | 3.9 (1.72) | 5.4 (1.70) | 4.8 (1.22) | 2.0 (0.73) |
|  | Range | 1, 7 | 2, 8 | 2, 8 | 1, 3 |
| 3 minutes | Mean (SD) | 3.8 (1.83) | 5.2 (1.55) | 4.7 (1.18) | 1.9 (0.78) |
|  | Range | 1, 7 | 2, 8 | 2, 7 | 1, 3 |
| Flagyl ® | | | | | |
| 15 seconds | Mean (SD) | 2.4 (1.08) | 3.6 (1.85) | 4.1 (1.82) | 1.3 (0.54) |
|  | Range | 1, 4 | 1, 7 | 1, 7 | 1, 3 |
| 3 minutes | Mean (SD) | 2.4 (1.35) | 3.4 (1.91) | 3.9 (1.90) | 1.3 (0.61) |
|  | Range | 1, 6 | 1, 7 | 1, 7 | 1, 3 |

SD = Standard deviation

TABLE 12

Non-Parametric Comparison of Categorical
Parameters for Hedonic Scale

| | | ATI-1501 vs Flagyl ® | | |
|---|---|---|---|---|
| Parameter | Time Point | Median Difference | Q1-Q3 | P value |
| Taste | 15 seconds | 1.0 | 1-2 | <0.0001 |
|  | 3 minutes | 1.0 | 1-3 | <0.0001 |
| Texture | 15 seconds | 2.0 | 0-3 | <0.001 |
|  | 3 minutes | 2.0 | 1-3 | <0.0001 |
| Smell | 15 seconds | 1.0 | 0-2 | 0.021 |
|  | 3 minutes | 0.0 | 0-2 | 0.035 |
| Bitterness | 15 seconds | 1.0 | 0-1 | <0.001 |
|  | 3 minutes | 1.0 | 0-1 | <0.001 |

$Q_1$ = first quartile, $Q_3$ = third quartile

Taste Test Sub-Study Results—Treatment Preference

The clinical value of taste improvements lies in their potential to impact subject preference and adherence to treatment. Therefore, the study included an assessment of treatment preference. After palatability assessments were completed and subjects had tasted both ATI-1501 and crushed metronidazole in apple sauce, subjects were asked which drug product they preferred. Subjects were also asked to rank the degree of their preference on a 5-point scale, where lower values indicated a greater preference for ATI-1501. A score of 1 indicated a strong preference for ATI-1501, a score of 5 indicated a strong preference for crushed metronidazole in apple sauce, and a score of 3 indicated no preference.

Subject responses suggested a clear preference for ATI-1501 over crushed metronidazole in apple sauce (Table 13). When asked directly to identify which drug product was preferred, 21 (84%) subjects indicated a preference for ATI-1501 over the crushed metronidazole tablet. The degree of preference data also suggested a clear preference for ATI-1501. The mean degree of preference score was 1.8, equating to a response between "very much prefer ATI-1501" (score=1) and "slightly prefer ATI-1501" (score=2). Only 3 subjects indicated a slight preference for the compounded metronidazole and no subjects indicated a strong preference for the crushed metronidazole tablet (score=5). Conversely, over 50% of subjects (n=13) indicated a strong possible preference for ATI-1501 (score=1).

TABLE 13

Summary of Subject Preference Responses

| Preferred Drug Product (3 minutes Post-Dose) | |
|---|---|
| ATI-1501, n (%) | 21 (84%) |
| Flagyl ®, n (%) | 4 (16%) |
| Degree of Preference (3 minutes Post-Dose) | |
| Mean (SD) | 1.8 (1.04) |
| Range | 1, 4 |

SD = standard deviation
ATI-1501 was administered as an oral suspension and Flagyl ® was crushed in up to 30 mL of apple sauce.

Taste Test Sub-Study Results—Effect of Treatment Sequence

A challenge in the design of palatability studies is that a subject must assess drug products in sequence and assessment of the first drug product is made without knowledge of the comparator product. If a subject scores the first drug product close to one of the boundaries of the scoring scales it may limit the subject's ability to differentiate the 2 products if the second product warrants an even more extreme score.

Given the uncertainty as to how treatment sequence might impact subject responses, subjects in the Taste Test sub-study were randomized such that, approximately half of all subjects received either ATI-1501 or crushed metronidazole in apple sauce first. As described above, pooled subject data demonstrated significant palatability improvements with ATI-1501 independent of treatment sequence. The potential impact of test sequence on responses was evaluated as a supplementary analysis. Descriptive statistics of the 9-point Hedonic scale scores for taste, texture, and smell, and the 3-point scale scores for bitterness are presented by treatment sequence in Table 14.

Analysis of subject responses when grouped by treatment sequence revealed differences in the relative scoring of ATI-1501. When ATI-1501 was administered first, ATI-1501 scores for taste and bitterness were only modestly improved over crushed metronidazole in apple sauce (0.7 units and 0.3 units, respectively). However, when crushed metronidazole in apple sauce was administered first, ATI-1501 scores were markedly higher relative to the crushed tablet. At 15 seconds post-dose, ATI-1501 mean taste scores were 2.3 units higher and mean bitterness scores 1.0 unit higher, demonstrating meaningful improvements over crushed metronidazole in apple sauce. This was not observed for texture and smell data, where differences between ATI-1501 and crushed metronidazole in apple sauce were less pronounced if subjects received crushed metronidazole in apple sauce first. These data suggested that treatment sequence may have had an impact on palatability scores that should be considered when interpreting the results.

TABLE 14

Summary of 9-Point Hedonic Scale and 3-Point Scale Values by Treatment Sequence

| | | Treatment Sequence XY | | | | Treatment Sequence YX | | | |
|---|---|---|---|---|---|---|---|---|---|
| | | \multicolumn{8}{c}{Time Post-Dose} | | | | | | | | |
| | | 15 seconds | | 3 minutes | | 15 seconds | | 3 minutes | |
| Parameter | | X | Y | X | Y | Y | X | Y | X |
| Taste | Mean (SD) | 2.8 (1.24) | 2.1 (1.12) | 2.7 (1.44) | 2.1 (1.50) | 2.8 (0.97) | 5.1 (1.31) | 2.8 (1.14) | 4.9 (1.51) |
| | Range | 1-5 | 1-4 | 1-6 | 1-6 | 1-4 | 3-7 | 1-5 | 3-7 |
| Texture | Mean (SD) | 5.2 (1.69) | 2.9 (1.93) | 5.1 (1.50) | 2.9 (1.98) | 4.3 (1.50) | 5.5 (1.78) | 3.9 (1.78) | 5.3 (1.67) |
| | Range | 2-8 | 1-6 | 2-7 | 1-6 | 2-7 | 3-8 | 2-7 | 3-8 |
| Smell | Mean (SD) | 4.5 (1.27) | 3.7 (1.97) | 4.5 (1.13) | 3.4 (2.10) | 4.5 (1.62) | 5.1 (1.16) | 4.4 (1.56) | 4.9 (1.24) |
| | Range | 2-7 | 1-7 | 2-6 | 1-7 | 2-7 | 3-8 | 2-7 | 3-7 |
| Bitterness | Mean (SD) | 1.5 (0.66) | 1.2 (0.38) | 1.3 (0.48) | 1.2 (0.55) | 1.4 (0.67) | 2.4 (0.51) | 1.4 (0.67) | 2.5 (0.52) |
| | Range | 1-3 | 1-2 | 1-2 | 1-3 | 1-3 | 2-3 | 1-3 | 2-3 |

| | Overall Preference | Overall Preference |
|---|---|---|
| Mean (SD) | 2.0 (1.15) | 1.6 (0.90) |
| Range | 1-4 | 1-4 |

SD = standard deviation, Treatment X = mL of ATI-1501 oral suspension at 250 mg metronidazole/5 mL, Treatment Y = 500 mg Flagyl ® tablet crushed in up to 30 mL of apple sauce.

Taste Test Sub-Study Results—Individual Subject Responses

Table 15, Table 16 and Table 17 summarize individual subject responses provided at 15 seconds post-dose on the taste, texture, and smell dimensions, respectively that could be classified in the "Dislike" (ie, Hedonic scale scores 1-3), "Neutral" (ie, 4-6), and "Like" (ie, 7-9) categories for ATI-1501 and Flagyl®.

On the taste dimension of the Hedonic scale (Table 15), 10 subjects provided responses in the "Dislike" category after the administration of ATI-1501 vs 20 subjects after Flagyl®. A total of 13 subjects provided responses in the "Neutral" category after the administration of ATI-1501 vs 5 subjects after Flagyl®. A total of 2 subjects provided responses in the "Like" category after the administration of ATI-1501 vs no subjects after Flagyl®.

TABLE 15

Individual Subject Responses at 15 Seconds Post-Dose on the Taste Dimension Classified in "Dislike," "Neutral," and "Like" Categories

| | ATI-1501 Oral Suspension | | | Flagyl ® Tablet Crushed in Apple Sauce | | |
|---|---|---|---|---|---|---|
| Category | Score | N (%) | Category | Score | N (%) | |
| Dislike | 1 | 2 (8) | Dislike | 1 | 6 (24) | |
| (n = 10) | 2 | 4 (16) | (n = 20) | 2 | 8 (32) | |
| | 3 | 4 (16) | | 3 | 6 (24) | |
| Neutral | 4 | 7 (28) | Neutral | 4 | 5 (20) | |
| (n = 13) | 5 | 3 (12) | (n = 5) | 5 | 0 (0) | |
| | 6 | 3 (12) | | 6 | 0 (0) | |
| Like | 7 | 2 (8) | Like | 7 | 0 (0) | |
| (n = 2) | 8 | 0 (0) | (n = 0) | 8 | 0 (0) | |
| | 9 | 0 (0) | | 9 | 0 (0) | |

N (%) = number (percentage) of subjects who provided the rating for each of the treatment conditions. N = 25 (number of subjects in the Sub-Study population) was the denominator used to calculate the percentage.

On the texture dimension of the Hedonic Scale (Table 16), 5 subjects provided responses in the "Dislike" category after the administration of ATI-1501 vs 11 subjects after Flagyl®. A total of 14 subjects provided responses in the "Neutral" category after the administration of ATI-1501 vs 13 subjects after Flagyl®. A total of 6 subjects provided responses in the "Like" category after the administration of ATI-1501 vs 1 subject after Flagyl®.

In comparison with the bitter taste profile and strong subject dislike for the crushed metronidazole in apple sauce, palatability data collected for ATI-1501 suggested a shift towards a more neutral and palatable flavor profile.

If subjects were exposed to crushed metronidazole in apple sauce prior to ATI-1501 assessment, taste and bitterness advantages of ATI-1501 over the crushed metronidazole in apple sauce were more pronounced, whereas texture

TABLE 16

Individual Subject Responses at 15 Seconds Post-Dose on the Texture Dimension Classified in "Dislike," "Neutral," and "Like" Categories

| | ATI-1501 Oral Suspension | | | Flagyl ® Tablet Crushed in Apple Sauce | |
| --- | --- | --- | --- | --- | --- |
| Category | Score | N (%) | Category | Score | N (%) |
| Dislike | 1 | 0 (0) | Dislike | 1 | 5 (20) |
| (n = 5) | 2 | 1 (4) | (n = 11) | 2 | 3 (12) |
| | 3 | 4 (16) | | 3 | 3 (12) |
| Neutral | 4 | 3 (12) | Neutral | 4 | 5 (20) |
| (n = 14) | 5 | 6 (24) | (n = 13) | 5 | 5 (20) |
| | 6 | 5 (20) | | 6 | 3 (12) |
| Like | 7 | 2 (8) | Like | 7 | 1 (4) |
| (n = 6) | 8 | 4 (16) | (n = 1) | 8 | 0 (0) |
| | 9 | 0 (0) | | 9 | 0 (0) |

N (%) = number (percentage) of subjects who provided the rating for each of the treatment conditions. N = 25 (number of subjects in the Sub-Study population) was the denominator used to calculate the percentage.

On the smell dimension of the Hedonic scale (Table 17), 3 subjects provided responses in the "Dislike" category after the administration of ATI-1501 vs 8 subjects after Flagyl®. A total of 20 subjects provided responses in the "Neutral" category after administration of ATI-1501 vs 14 subjects after Flagyl®. A total of 2 subject provided responses in the "Like" category after the administration of ATI-1501 vs 3 subjects after Flagyl®.

and smell advantages were less pronounced. As a result, pooled data that included subjects receiving ATI-1501 before crushed metronidazole in apple sauce may be masking the overall magnitude of ATI-1501's taste and bitterness advantages. Regardless, statistically significant improvements in taste and bitterness were recorded for ATI-1501 in the pooled population.

TABLE 17

Individual Subject Responses at 15 Seconds Post-Dose on the Smell Dimension Classified into "Dislike," "Neutral," and "Like" Categories

| | ATI-1501 Oral Suspension | | | Flagyl ® Tablet Crushed in Apple Sauce | |
| --- | --- | --- | --- | --- | --- |
| Category | Score | N (%) | Category | Score | N (%) |
| Dislike | 1 | 0 (0) | Dislike | 1 | 3 (12) |
| (n = 3) | 2 | 1 (4) | (n = 8) | 2 | 3 (12) |
| | 3 | 2 (8) | | 3 | 2 (8) |
| Neutral | 4 | 5 (20) | Neutral | 4 | 5 (20) |
| (n = 20) | 5 | 13 (52) | (n = 14) | 5 | 8 (32) |
| | 6 | 2 (8) | | 6 | 1 (4) |
| Like | 7 | 1 (4) | Like | 7 | 3 (12) |
| (n = 2) | 8 | 1 (4) | (n = 3) | 8 | 0 (0) |
| | 9 | 0 (0) | | 9 | 0 (0) |

N (%) = number (percentage) of subjects who provided the rating for each of the treatment conditions. N = 25 (number of subjects in the Sub-Study population) was the denominator used to calculate the percentage.

Taste Test Sub-Study Results—Taste Test Sub-Study Conclusions

Data collected from the Taste Test sub-study provide initial indications of improved palatability and subject preference for ATI-1501 over the crushed metronidazole tablets in apple sauce, with clear and statistically significant improvements across all palatability measures. These palatability improvements were associated with a subject preference for ATI-1501. When asked directly, 84% of subjects indicated a preference for ATI-1501 over crushed metronidazole in apple sauce, and when asked to rate the degree of preference, over 50% of all subjects indicated that they "very much prefer" ATI-1501 over the crushed metronidazole tablets in apple sauce.

10. Safety Evaluation 10.1 Adverse Events

No deaths or other serious TEAEs were reported in both the main and sub-study. No subject was discontinued due to a TEAE.

A summary of TEAEs by MedDRA SOC and preferred term is provided for the Taste Test sub-study in Table 18. Three (12%) of the 25 subjects experienced a total of 6 TEAEs during the Taste Test sub-study, and all 6 events were assessed as mild in intensity. The most commonly reported TEAE was nausea, reported by 3 subjects (12%) enrolled in the sub-study.

Two subjects (8%) experienced a total of 4 possibly related TEAEs during the sub-study. All 4 events occurred within 1 hour after administration of ATI-1501. All TEAEs were mild in intensity and resolved within 3 hours without medical intervention.

TABLE 18

Summary of Treatment-Emergent Adverse Events for the Taste Test Sub-Study (Sub-Study Population)

| MedDRA System Organ Class Preferred Term | ATI-1501 (N = 25) | Flagyl ® (N = 25) |
|---|---|---|
| Any TEAE | 3 (12.0) | 0 |
| Gastrointestinal disorders | 3 (12.0) | 0 |
| Nausea | 3 (12.0) | 0 |
| Abdominal pain | 3 (12.0) | 0 |
| Gastrointestinal hypermotility | 1 (4.0) | 0 |
| Nervous System disorders | 1 (4.0) | 0 |
| Dizziness | 1 (4.0) | 0 |
| Psychiatric disorders | 1 (4.0) | 0 |
| Anxiety | 1 (4.0) | 0 |

MedDRA = Medical Dictionary for Regulatory Activities,
TEAE = treatment-emergent adverse event
Percentage was calculated based on the number of subjects in the Sub-Study Population as the denominator [% = (n/N) * 100].

10.3 Safety Conclusions

Safety conclusions included:

Single 500 mg doses of ATI-1501 and Flagyl® were well tolerated under both fasted and fed conditions.

Overall, the incidence of TEAEs was higher under fed compared to fasted conditions for both ATI-1501 and Flagyl®.

No deaths, other SAEs, or severe TEAEs were reported and no withdrawals due to TEAEs occurred in the study.

Almost all (97%) of TEAEs were mild in intensity and the majority (66%) of all TEAEs were assessed as unrelated or unlikely related to the study drug.

All TEAEs resolved within the pre-defined safety Follow-up period.

No safety laboratory and physical examination abnormalities were considered clinically significant.

ECG abnormalities that were reported as TEAEs included 1 case each of a T wave inversion and ventricular extrasystoles.

Vital sign abnormalities that were reported as TEAEs included 1 case of tachycardia.

None of these events required medical intervention and all resolved by the Follow-up visit.

The TEAEs and other safety observations from this study are consistent with the known safety profile of metronidazole.

11. Discussion and Overall Conclusions 11.1 Discussion

This Phase 1 randomized, 2-sequence, 4-period, crossover clinical trial was the first study to evaluate ATI-1501 oral suspension in humans. ATI-1501 is a new taste-masked oral suspension formulation of metronidazole to address the known limitations of the existing oral tablet formulations, including their bitter/metallic taste, a determinant of suboptimal treatment compliance. Further advantage of the oral suspension formulation is that it can be consumed easily by patients who have difficulty swallowing tablets (eg, geriatric patients with dysphagia or pediatric patients).

The primary objective of the ATI-1501-02 study was to determine the relative bioavailability of ATI-1501 oral suspension (10 mL of ATI-1501 at 250 mg metronidazole/5 mL concentration) compared to Flagyl® 500 mg tablets, under fasted and fed conditions. The secondary objectives of the study were to characterize the PK profile of ATI-1501 following a single 10 mL oral dose to investigate the effect of food on the absorption of ATI-1501 and to evaluate the safety of ATI-1501. The study also aimed to assess the palatability of ATI-1501 against Flagyl® tablets crushed in up to 30 mL of apple sauce using a 9-point Hedonic scale for taste, texture, and smell and a 3-point scale for bitterness. Subjects were also asked to indicate which drug product was preferred and to rate the degree of their preference on a 5-point scale.

A total of 48 subjects were randomized to 1 of 2 treatment sequences in the main study, and included in the Randomized/ITT, Safety, and PK Populations. Each single dose administration (first 2 under fasted and the third and fourth under fed conditions) was separated by at least 7 days (14 days between treatment period 1 and treatment period 2). Of the 44 subjects who completed the main study, 25 subjects were randomized to the Taste Test sub-study and were included in the Sub-Study Population. All 25 subjects completed the Taste Test sub-study.

The evaluation of relative bioavailability between ATI-1501 and Flagyl® under both fasted and fed conditions was carried out by the statistical evaluation of $C_{max}$, $AUC_{0-t}$, and $AUC_{0-inf}$ for metronidazole using an ANOVA mixed-effects model and standard bioequivalence approach with 90% CIs. The geometric mean ratios of $C_{max}$, $AUC_{0-t}$, and $AUC_{0-inf}$ for the test vs reference treatments were all close to 100% (range 94.285% to 103.180%). It was shown that 90% CI of geometric mean ratios for $C_{max}$, $AUC_{0-t}$, and $AUC_{0-inf}$ were all within the bioequivalent limits of 80% to 125%. These results demonstrated that 500 mg ATI-1501 was bioequivalent to 500 mg Flagyl® under fasted condition or fed condition.

Mean plasma concentrations of metronidazole increased rapidly following oral administration of ATI-1501 under fasted condition with a peak observed around 1 hour post-dose, while the maximum mean concentration under fed condition appeared to be delayed at 3 hours post-dose. Mean plasma metronidazole concentrations were higher for ATI-1501 under fasted condition (peak at approximately 11 μg/mL) compared to fed condition (peak at approximately 8 μg/mL).

There was a mild food effect on the PK of 500 mg ATI-1501 (reduced $C_{max}$ by around 26% and delayed $T_{max}$ by 1.5 hours) when administered following a high-fat, high-calorie meal.

Palatability and treatment preference assessments (ATI-1501 oral suspension compared to Flagyl® tablet crushed in up to 30 mL of apple sauce) were completed in a subset of 25 subjects randomized in the Taste Test sub-study. Subjects indicated statistically significant improvements with ATI-1501 compared to crushed Flagyl® tablets across all independent palatability metrics assessed.

Consistent with its improved palatability, a subject preference for ATI-1501 was observed. When asked directly, the majority of subjects (84%) indicated preference for ATI-1501 over crushed metronidazole in apple sauce. When preference was split out by degree of preference, over half of all sub-study subjects (n=13, 52%) indicated preference for ATI-1501.

Single 500 mg doses of both ATI-1501 and Flagyl® were well tolerated. No deaths, other SAEs, or withdrawals due to AEs occurred during the study. Almost all (97%) of TEAEs were mild in intensity and the majority (66%) of all TEAEs were assessed as unrelated or unlikely related to the study drug. All TEAEs resolved within the pre-defined safety Follow-up period.

Overall, the incidence of TEAEs was higher under fed compared to fasted conditions for both ATI-1501 (28.9% vs 19.6%, respectively) and Flagyl® (24.4% vs 18.8%, respectively). Combined with the PK findings, these observations indicated that the higher exposure to metronidazole following oral administration of ATI-1501 under fasted condition (peak plasma concentration of approximately 11 µg/mL reached within around 1 hour post-dose; median $AUC_{0-t}$ of 134.5 h*µg/mL) compared to fed conditions (peak plasma concentration of approximately 8 µg/mL reached within around 3 hour post-dose; median $AUC_{0-t}$ of 118.6 h*µg/mL) was not associated with an increased incidence of adverse experiences.

The incidence and types of TEAEs reported in the current study were consistent with the known safety profile of metronidazole. Warnings associated with the use of metronidazole include central nervous system effects and peripheral nervous system effects (primarily peripheral and optic neuropathy) (Pfizer 2015). The most common gastrointestinal adverse reactions previously reported by patients receiving metronidazole include nausea, sometimes accompanied by headache, anorexia, and occasionally vomiting; diarrhea; epigastric distress; and abdominal cramping and constipation (Pfizer 2015). In the current study, the most frequently reported TEAEs by SOC were gastrointestinal disorders (18.8%), followed by general disorders and administration site conditions (14.6%), and nervous system disorders (14.6%). The most common TEAEs by preferred term were headache (14.6%) and nausea (12.5%). The frequency of headaches was higher when either of the study drugs was administered under fed vs fasted conditions (approximately 9% vs. 2%, respectively); no other apparent differences in the TEAE occurrences were observed between the 2 treatment conditions. The higher frequency of general disorders and administration site conditions was primarily driven by local events, associated with the study procedures (venipunctures).

Consistent with the known cardiac safety profile of metronidazole, no effect of the study drug on cardiac repolarization (QT or QTc values) or on cardiac conduction (PR interval) was detected during the study. Flattening of the T wave in ECG tracings has been previously reported with metronidazole (Pfizer 2015). In the current study, T wave inversion was detected in 1 subject; however, the event was not associated with other clinical symptoms or a laboratory abnormality, resolved during the safety Follow-up period, and was assessed by the investigator as unrelated to the study drug.

Overall, the current Phase 1 study has not identified any new safety findings or risks associated with metronidazole and supports further clinical assessment of ATI-1501 oral solution in the target indications.

Overall Conclusions

Overall conclusions include:
  500 mg ATI-1501 administered as an oral suspension was bioequivalent to 500 mg Flagyl® oral tablet under either fasted or fed condition.
  When 500 mg ATI-1501 oral suspension was administered with a high-fat, high-calorie meal, $C_{max}$ was reduced by around 26% and delayed by approximately 1.5 hours, indicating that a complete absence of food effect on the bioavailability of the drug was not established.
  Statistically significant palatability improvements with ATI-1501 relative to crushed metronidazole tablets in apple sauce were detected across all 4 palatability tests: taste, texture, smell, and bitterness.
  Subject preference for ATI-1501, with 84% of subjects preferring ATI-1501 over crushed metronidazole in apple sauce.
  Over half of all subjects indicated the strongest possible preference for ATI-1501 on a 5-point preference scale.
  The mean overall preference score (1.8) indicated an overall preference for ATI-1501 over Flagyl® tablet crushed in apple sauce. The apparent consistency between the treatment preference and palatability data underscore the rigor of the study design and highlight the potential benefits of ATI-1501 over the existing oral formulation in terms of an anticipated improved acceptance and adherence to the prescribed treatment regimen.
  Single 500 mg doses of ATI-1501 oral suspension and of Flagyl® tablets were well tolerated under both fasted and fed conditions.
  Overall incidence of TEAEs was higher under fed compared to fasted conditions for both ATI-1501 and Flagyl®.
  No deaths, other SAEs, or severe TEAEs were reported and no withdrawals due to TEAEs occurred in this study.
  Almost all (97%) of TEAEs were mild in intensity and the majority (66%) of all TEAEs were assessed as unrelated or unlikely related to the study drug.
  No safety laboratory and physical examination abnormalities were considered clinically significant.
  The TEAEs and other safety observations from this study are consistent with the known safety profile of metronidazole.
  Taken together, the results of the main study demonstrated that ATI-1501 oral suspension was bioequivalent to and equally as safe and well tolerated as an equivalent dose of Flagyl® oral tablet under either fasted or fed conditions. This was coupled with the findings from the Taste Test sub-study, which demonstrated improved palatability and treatment preference in favour of ATI-1501. The results indicate that ATI-1501 is a successfully taste-masked oral suspension reformulation of metronidazole that is a therapeutically equivalent alternative to Flagyl® tablets.

Example 9: Alternative Manufacture of Metronidazole Formulations

Figure 9:
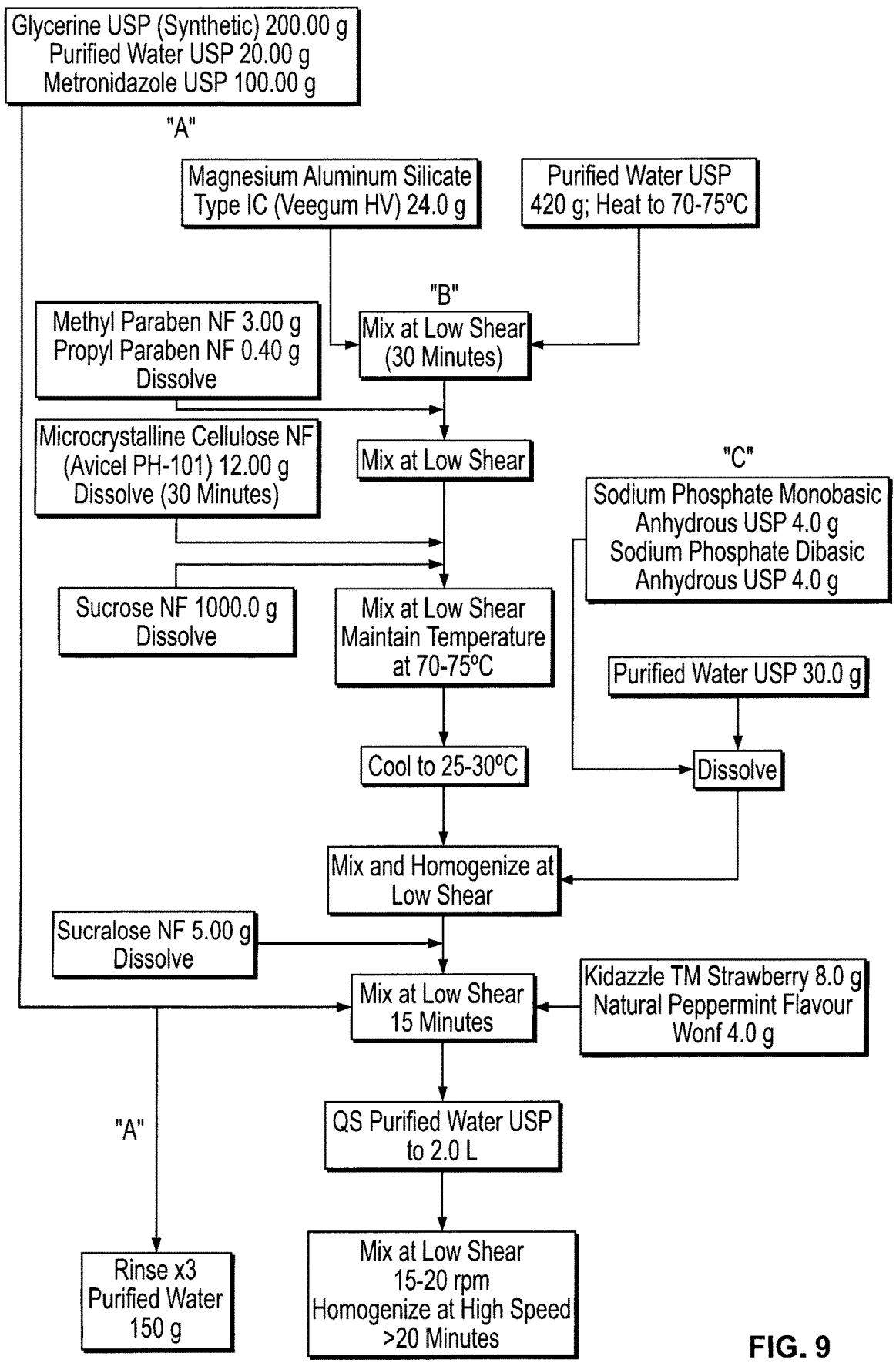
FIG. 9 shows a schematic of an alternate process for making a metronidazole pharmaceutical formulation.

An alternative strategy for manufacturing a metronidazole formulation is described below and shown in FIG. 9. The equipment used for manufacture is known in the art and commercially available. As a skilled person will appreciate, further optimization may be required to scale-up production of the formulations provided herein.

The manufacturing strategies involve combining three taste masking steps. These steps are: 1) placing the metronidazole within a semi/pseudo syrup; 2) suspending the metronidazole-containing semi/pseudo syrup in the MgAlSi to trap the metronidazole in-between the MgAlSi clay platelets; and 3) adding various sweeteners and/or flavors.

When manufacturing a metronidazole formulation that does not contain any flavoring agents, the step of adding the flavoring agents is omitted.

Step 1: In a stainless steel vessel equipped with a low shear mixer, disperse Metronidazole USP into Glycerine USP (synthetic) and Purified water USP. Mix to create uniform and smooth slurry. Mix continuously until the addition to main vessel. Part A.

| | |
|---|---|
| Metronidazole USP | 100.00 g |
| Glycerine USP (Synthetic) | 200.00 g |
| Purified Water USP | 20.00 g |

Step 2: In the main stainless steel vessel equipped with a low shear mixer and homogenizer, add 420 g of Purified Water USP. Heat Purified Water to 70-75° C. With low shear mixing disperse Magnesium Aluminum Silicate Type IC (Veegum HV). Mix for 30 (thirty) minutes

| | |
|---|---|
| Purified Water USP | 433.60 g |
| Magnesium Aluminum Silicate Type IC (Veegum HV) | 24.00 g |

Step 3: In the main stainless steel vessel, add Methyl Paraben and Propyl Paraben using low shear mixer and dissolve

| | |
|---|---|
| Methyl Paraben NF | 3.00 g |
| Propyl Paraben NF | 0.40 g |

Step 4: In the main stainless steel vessel using a low shear mixer, disperse Microcrystalline Cellulose NF (Avicel PH-101). Mix for 30 minutes

| | |
|---|---|
| Microcrystalline Cellulose NF (Avicel PH-101) | 12.00 g. |

Step 5: In the main stainless steel vessel, add and dissolve Sucrose NF using low shear mixing while maintaining temperature at 70-75° C.

| | |
|---|---|
| Sucrose | 1000.00 g |

Step 6: Cool the mixture to 25-30° C.

Step 7: Mix and homogenize at high sheer for 15-20 minutes.

Step 8: In the main stainless steel vessel, add and dissolve Sucralose NF using low shear mixing

| | |
|---|---|
| Sucralose NF | 5.00 g |

Step 9: In a separate vessel dissolve Sodium Phosphate Monobasic Anhydrous USP and Sodium Phosphate Dibasic Anhydrous USP into 12 g of Purified Water USP. Add this mixture to the main vessel. Mix with low shear mixing.

| | |
|---|---|
| Sodium Phosphate Monobasic Anhydrous USP | 4.00 g |
| Sodium Phosphate Dibasic Anhydrous USP | 4.00 g |
| Purified Water USP | 30.00 g |

Step 10: Add active phase from step 1 to the main vessel. Mix with low shear mixing set between for minimum 15 minutes.

Rinse the vessel containing the active phase three (3) times with the portions of 50 mL of Purified Water USP.

| | |
|---|---|
| Purified Water USP | 150.00 g |

Step 11: Add the Kidazzle Strawberry and the Natural Peppermint Flavour Wonf to the main vessel mixture and QS with Purified Water USP to final volume

| | |
|---|---|
| Kidazzle ™ Strawberry | 8.00 g |
| Natural Peppermint Flavour Wonf | 4.00 g |
| Purified Water USP | QS |

Step 12: Mix Final formulation at low shear 15-20 rpm and homogenize at high speed for not less than twenty (20) minutes.

Step 13: Fill into HDPE bottles immediately.

REFERENCES CITED

The references cited below, and all other references cited herein, are each incorporated herein by reference as if set forth in its entirety:

Aguzzi C, Cerezo P, Viseras C, Caramella C. Use of clays as drug delivery systems: possibilities and limitations. Appl Clay Sci. 2007; 36:22-36.

Bai S, Dormer N, Shoults C, Meyer A, Pierce C D, Neville K A, Kearns G L. Palatability of a novel oral formulation of prednisone in healthy young adults. J Pharm Pharmacol. 2017 April; 69(4):489-496.

Bastiaans D E T, Immohr L I, Zeinstra G G, Strik-Albers R, Pein-Hackelbusch M, van der Flier M, de Haan A F J, Boelens J J, Lankester A C, Burger D M, Warris A. In vivo and in vitro palatability testing of a new paediatric formulation of valaciclovir. Br J Clin Pharmacol. 2017 December; 83(12):2789-2797. Bempong D K, Manning R G, Mirza T, Bhattacharyya L. A stability-indicating HPLC assay for metronidazole benzoate. J Pharm Biomed Anal. 2005; 38:776-780.

Bempong D K, Manning R G, Mirza T, Bhattacharyya L. A stability-indicating HPLC assay for metronidazole benzoate. Journal of Pharmaceutical and Biomedical Analysis 38 (2005) 776-780

Bhattacharjee S, Majumdar S, Guha N, Dutta G. Approaches taken for masking of bitter taste in pharmaceutical products. World Journal of Pharmacy and Pharmaceutical Sciences. 2016; 5(8):1752-64.

Ciullo P A. Rheological properties of magnesium aluminum silicate/xantham gum dispersions. J Soc Cosmet Chem. 1981; 32:275-278.

DailyMed—METRONIDAZOLE (metronidazole) tablet. US National Library of Medicine. https://dailymed.nlm-.nih.gov/dailymed/drugInfo.cfm?setid=a66abf44-9ae9-4342-b69a-ebaa1f967d78. Accessed Jul. 25, 2017.

D'Hondt M, Wynendaele E, Vandercruyssen K, Bauters T, Vandenbroucke J, Mullens S, et al. Investigation of active pharmaceutical ingredient loss in pharmaceutical compounding of capsules. J Pharm Biomed Anal. 2014; 96:68-76.

Duro R, Souto C, Gomez-Amoza L, Martinez-Pacheco R, Conheiro A. Interfacial adsorption of polymers and surfactants: implications for the properties of disperse systems of pharmaceutical interest. Drug Dev Ind Pharm. 1999; 25(7):817-829.

Elder D P, Crowley P J. Antimicrobial preservatives part two: choosing a preservative. American Pharmaceutical Review [Internet]. 2012 January [cited 2017 Jan. 12]. CompareNetworks Inc. Available from: http://www.americanpharmaceuticalreview.com/Featured-Articles/38885-Antimicrobial-Preservatives-Part-Two-Choosing-a-Preservative/.

Gee S C, Hagemann™. Palatability of liquid anti-infectives: clinician and student perceptions and practice outcomes. J Pediatr Pharmacol Ther. 2007; 12:216-223.

Healy D P, Dansereau R J, Dunn A B, Clendening C E, Mounts A W, Deepe G S Jr. Reduced tetracycline bioavailability caused by magnesium aluminum silicate in liquid formulations of bismuth subsalicyclate. Ann Pharmacother. 1997; 31:1460-1464.

Houghton G W, Hundt H K L, Muller F O, Templeton R. A comparison of the pharmacokinetics of metronidazole in man after oral administration of single doses of benzoyl-metronidazole and metronidazole. Br J Clin Pharmacol. 1982; 14:201-206.

Ishizaka T, Okada S, Takemoto E, Tokuyama E, Tsuji E, Mukai J, et al. The suppression of enhanced bitterness intensity of macrolide dry syrup mixed with an acidic powder. Chem Pharm Bull. 2007; 55:1452-1457.

Kalaskar R, Singh R P. Taste masking: a novel technique for oral drug delivery system. Asian Journal of Pharmaceutical Research and Development. 2014; 2(3):1-14.

Kaushik D, Durej a H. Recent patents and patented technology platforms for pharmaceutical taste masking. Recent Pat Drug Deliv Formul. 2014; 8:37-45.

Lawless H T, Heymann H. Sensory Evaluation of Food: Principles and Practice. January 2010. Springer Science & Business Media. DOI: 10.1007/978-1-4419-6488-5.

Lim J. Hedonic scaling: A review of methods and theory. Food Quality and Preference. 2011; 22(8):733-747.

Matthew M, Das Gupta V, Bethea C. Stability of metronidazole benzoate in suspensions. J Clin Pharm Ther. 1994; 19:31-34.

Peryam D R, Girardot N F. Advanced taste-test method. Food Eng. 1952; 24:58-61, 194.

Peryam D R, Pilgrim F J. Hedonic scale method of measuring food preferences. Food Technol. 1957; 11:9-14.

Pfizer, 2015. FLAGYL® (metronidazole) tablets—Prescribing Information. LAB-0162-6.2. Revised June 2015.

Ramasamy T, Kandhasami U D S, Ruttala H, Shanmugam S. Formulation and evaluation of xantham gum based aceclofenac tablets for colon targeted drug delivery. Brazilian Journal of Pharmaceutical Sciences. 2011; 47:299-311.

Rowe R C, Sheskey P J, Quinn M E, editors. Handbook of Pharmaceutical Excipients. Sixth Edition. London, UK: The Pharmaceutical Press; 2009. 888 p.

Sana S, Rajani A, Sumedha N, Mahesh B. Formulation and evaluation of taste masked oral suspension of dextromethorphan hydrobromide. Int J Drug Dev Res. 2012; 4:159-172.

Sanofi-Aventis, 2016. FLAGYL® (metronidazole) capsules. Product Monograph. Submission Control No. 197442. s-a Version 7.0. Revised Nov. 3, 2016.

Sharma S, Lewis S. Taste masking technologies: a review. Int J Pharm Sci. 2010; 2(2):6-13.

Sohi H, Sultana Y, Khar R K. Taste masking technologies in oral pharmaceuticals: recent developments and approaches. Drug Dev Ind Pharm. 2004; 30(5):429-448.

Stahl P H, Wermuth C G, editors. Handbook of Pharmaceutical Salts: Properties, Selection, and Use. New Jersey: John Wiley & Sons, Inc; 2008. 388 p.

Tsuji E, Uchida T, Fukui A, Fujii R, Sunada H. Evaluation of bitterness suppression of macrolide dry syrups by jellies. Chem Pharm Bull. 2006; 54:310-314. Wichchukit S, O'Mahony M. The 9-point hedonic scale and hedonic ranking in food science: some reappraisals and alternatives. J Sci Food Agric. 2015; 95:2167-2178.

What is claimed is:

1. An oral pharmaceutical liquid suspension comprising a) metronidazole or a pharmaceutically acceptable salt thereof; and b) magnesium aluminum silicate, wherein the magnesium aluminum silicate is a natural product.

2. An oral pharmaceutical liquid suspension comprising a) metronidazole or a pharmaceutically acceptable salt thereof; b) magnesium aluminum silicate; and c) and at least one flavoring agent, wherein the magnesium aluminum silicate is a natural product.

3. The oral pharmaceutical liquid suspension of claim 1, further comprising at least one sweetener.

4. The oral pharmaceutical liquid suspension of claim 1, wherein the metronidazole or a pharmaceutically acceptable salt thereof is present at a concentration of about 250 mg per 5 ml of the oral pharmaceutical liquid suspension.

5. The oral pharmaceutical liquid suspension of claim 1, wherein the metronidazole or a pharmaceutically acceptable salt thereof is metronidazole base.

6. The oral pharmaceutical liquid suspension of claim 1, wherein the magnesium aluminum silicate is magnesium aluminum silicate Type 1C.

7. The oral pharmaceutical liquid suspension of claim 1, wherein the concentration of magnesium aluminum silicate is between 1% and 10% (w/v) of the oral pharmaceutical.

8. The oral pharmaceutical liquid suspension of claim 3, wherein the sweetener is a natural sweetener selected from the group consisting of sucrose, glucose, fructose, stevia, and mixtures thereof.

9. The oral pharmaceutical liquid suspension of claim 3, wherein the sweetener is an artificial sweetener selected from the group consisting of sucralose, sorbitol, saccharin, aspartame, acesulfame potassium, neotame, advantame, and mixtures thereof.

10. The oral pharmaceutical liquid suspension of claim 2, wherein the at least one flavoring agent is selected from the group consisting of natural flavors, artificial flavors, mint, and mixtures thereof.

11. The oral pharmaceutical liquid suspension of claim 10, wherein the natural flavor is a natural fruit flavor selected from the group consisting of cherry, strawberry, raspberry, and mixtures thereof.

12. The oral pharmaceutical liquid suspension of claim 10, wherein the mint is peppermint.

13. The oral pharmaceutical liquid suspension of claim 10, wherein the at least one flavoring agent comprises cherry, strawberry, raspberry, peppermint, or mixtures thereof.

14. The oral pharmaceutical liquid suspension of claim 1, further comprising one or more excipients, wherein the one or more excipients comprises one or more of a preservative, a buffer, a viscosity agent, and a solvent.

15. The oral pharmaceutical liquid suspension of claim 14, wherein the buffer comprises sodium phosphate monobasic or sodium phosphate dibasic.

16. The oral pharmaceutical liquid suspension of claim 14, wherein the solvent comprises one or more of glycerol, alcohol, propylene glycol, or a combination thereof.

17. An oral pharmaceutical liquid suspension comprising: metronidazole, sucrose, glycerin, purified water, magnesium aluminum silicate, microcrystalline cellulose, sucralose, sodium phosphate, one or more preservatives, strawberry flavoring agent and peppermint flavoring agent, wherein the magnesium aluminum silicate is a natural product.

18. A method of treating an infection in a patient, said method comprising the step of administering to the patient an effective amount of an oral pharmaceutical liquid suspension comprising:
   a) metronidazole or a pharmaceutically acceptable salt thereof and magnesium aluminum silicate; or
   b) metronidazole or a pharmaceutically acceptable salt thereof; magnesium aluminum silicate; and at least one flavoring agent;
   wherein the magnesium aluminum silicate is a natural product.

19. The method of claim 18, wherein the infection is a bacterial infection, a fungal infection, a protozoan infection, amebiasis, pelvic inflammatory disease, endocarditis, bacterial vaginosis, dracunculiasis, giardiasis, or trichomoniasis.

20. The method of claim 19, wherein the bacterial infection is caused by one or more of a gram-positive bacterium, a gram-negative bacterium, an aerobic bacterium and an anaerobic bacterium.

21. The method of claim 18, wherein the patient is a geriatric patient or a pediatric patient.

\* \* \* \* \*